(12) United States Patent
Loudin et al.

(10) Patent No.: US 9,956,397 B2
(45) Date of Patent: May 1, 2018

(54) POLYMER FORMULATIONS FOR NASOLACRIMAL STIMULATION

(71) Applicant: Oculeve, Inc., South San Francisco, CA (US)

(72) Inventors: James Donald Loudin, Alhambra, CA (US); Amitava Gupta, Roanoke, VA (US); Marie Dvorak Christ, Laguna Beach, CA (US); F. Richard Christ, Laguna Beach, CA (US)

(73) Assignee: Oculeve, Inc., Pleasanton, CA (US)

( * ) Notice: Subject to any disclaimer, the term of this patent is extended or adjusted under 35 U.S.C. 154(b) by 0 days. days.

(21) Appl. No.: 15/700,935

(22) Filed: Sep. 11, 2017

(65) Prior Publication Data
US 2017/0368333 A1    Dec. 28, 2017

Related U.S. Application Data

(63) Continuation of application No. 14/630,471, filed on Feb. 24, 2015, now Pat. No. 9,770,583.

(60) Provisional application No. 62/067,350, filed on Oct. 22, 2014, provisional application No. 62/035,221, filed on Aug. 8, 2014, provisional application No.
(Continued)

(51) Int. Cl.
| | |
|---|---|
| *A61N 1/05* | (2006.01) |
| *A61N 1/04* | (2006.01) |
| *C08F 220/54* | (2006.01) |
| *H01B 1/12* | (2006.01) |

(Continued)

(52) U.S. Cl.
CPC ......... *A61N 1/0546* (2013.01); *A61N 1/0456* (2013.01); *C08F 220/54* (2013.01); *C08F 230/08* (2013.01); *H01B 1/125* (2013.01); *A61N 1/0496* (2013.01); *A61N 1/36014* (2013.01); *Y10T 29/49826* (2015.01); *Y10T 29/49885* (2015.01)

(58) Field of Classification Search
CPC ... A61N 1/0456; A61N 1/0546; C08F 220/54; H01B 1/125
See application file for complete search history.

(56) References Cited

U.S. PATENT DOCUMENTS

| | | | |
|---|---|---|---|
| 3,620,219 A | 11/1971 | Barker | |
| 3,709,228 A | 1/1973 | Barker et al. | |

(Continued)

FOREIGN PATENT DOCUMENTS

| | | |
|---|---|---|
| CN | 103467652 A | 12/2013 |
| EM | 2102681-0001 | 10/2012 |

(Continued)

OTHER PUBLICATIONS

Acar, M. et al. (2013). "Ocular surface assessment in patients with obstructive sleep apnea-hypopnea syndrome," Sleep Breath 17(2):583-588.

(Continued)

*Primary Examiner* — William Levicky
(74) *Attorney, Agent, or Firm* — Cooley LLP

(57) ABSTRACT

Described herein are polymer formulations for facilitating electrical stimulation of nasal or sinus tissue. The polymer formulations may be hydrogels that are prepared by a UV cross-linking process. The hydrogels may be included as a component of nasal stimulator devices that electrically stimulate the lacrimal gland to improve tear production and treat dry eye. Additionally, devices and methods for manufacturing the nasal stimulators, including shaping of the hydrogel, are described herein.

9 Claims, 56 Drawing Sheets

Related U.S. Application Data

62/027,139, filed on Jul. 21, 2014, provisional application No. 61/944,340, filed on Feb. 25, 2014.

(51) Int. Cl.
*C08F 230/08* (2006.01)
*A61N 1/36* (2006.01)

(56) References Cited

U.S. PATENT DOCUMENTS

| | | |
|---|---|---|
| 3,885,550 A | 5/1975 | MacLeod |
| D257,495 S | 11/1980 | Bros et al. |
| 4,495,676 A | 1/1985 | Hartmetz |
| 4,520,825 A | 6/1985 | Thompson et al. |
| 4,590,942 A | 5/1986 | Brenman et al. |
| 4,628,933 A | 12/1986 | Michelson |
| 4,681,121 A | 7/1987 | Kobal |
| 4,684,362 A | 8/1987 | Holt |
| 4,706,680 A | 11/1987 | Keusch et al. |
| 4,735,207 A | 4/1988 | Nambu et al. |
| 4,777,954 A | 10/1988 | Keusch et al. |
| 4,780,932 A | 11/1988 | Bowman et al. |
| 4,868,154 A | 9/1989 | Gilbard et al. |
| 4,926,880 A | 5/1990 | Claude et al. |
| 4,957,480 A | 9/1990 | Morenings |
| 4,988,358 A | 1/1991 | Eppley et al. |
| 5,025,807 A | 6/1991 | Zabara |
| 5,072,724 A | 12/1991 | Marcus |
| 5,078,733 A | 1/1992 | Eveleigh et al. |
| 5,090,422 A | 2/1992 | Dahl et al. |
| 5,099,829 A | 3/1992 | Wu |
| 5,147,284 A | 9/1992 | Fedorov et al. |
| 5,324,316 A | 6/1994 | Schulman et al. |
| 5,342,410 A | 8/1994 | Braverman |
| 5,345,948 A | 9/1994 | O'Donnell, Jr. |
| 5,360,438 A | 11/1994 | Fisher |
| 5,498,681 A | 3/1996 | Askari et al. |
| 5,514,131 A | 5/1996 | Edwards et al. |
| 5,533,470 A | 7/1996 | Rose |
| 5,545,617 A | 8/1996 | Dartt et al. |
| 5,571,101 A | 11/1996 | Ellman et al. |
| 5,607,461 A | 3/1997 | Lathrop |
| 5,640,978 A | 6/1997 | Wong |
| 5,683,436 A | 11/1997 | Mendes et al. |
| 5,707,400 A | 1/1998 | Terry et al. |
| 5,713,833 A | 2/1998 | Milligan |
| 5,720,773 A | 2/1998 | Lopez-Claros |
| 5,733,282 A | 3/1998 | Ellman et al. |
| 5,735,817 A | 4/1998 | Shantha |
| 5,792,100 A | 8/1998 | Shantha |
| 5,794,614 A | 8/1998 | Gruenke et al. |
| 5,800,685 A | 9/1998 | Perrault |
| 5,843,140 A | 12/1998 | Strojnik |
| 5,900,407 A | 5/1999 | Yerxa et al. |
| 5,904,658 A | 5/1999 | Niederauer et al. |
| 5,948,006 A | 9/1999 | Mann |
| 6,001,088 A | 12/1999 | Roberts et al. |
| 6,020,445 A | 2/2000 | Vanderlaan et al. |
| 6,035,236 A | 3/2000 | Jarding et al. |
| 6,051,017 A | 4/2000 | Loeb et al. |
| 6,083,251 A | 7/2000 | Shindo |
| 6,102,847 A | 8/2000 | Stielau |
| 6,152,916 A | 11/2000 | Bige |
| 6,205,359 B1 | 3/2001 | Boveja |
| 6,208,902 B1 | 3/2001 | Boveja |
| 6,240,316 B1 | 5/2001 | Richmond et al. |
| 6,246,911 B1 | 6/2001 | Seligman |
| 6,270,796 B1 | 8/2001 | Weinstein |
| 6,272,382 B1 | 8/2001 | Faltys et al. |
| 6,275,737 B1 | 8/2001 | Mann |
| 6,277,855 B1 | 8/2001 | Yerxa |
| 6,284,765 B1 | 9/2001 | Caffrey |
| 6,324,429 B1 | 11/2001 | Shire et al. |
| 6,327,504 B1 | 12/2001 | Dolgin et al. |
| 6,366,814 B1 | 4/2002 | Boveja et al. |
| 6,405,079 B1 | 6/2002 | Ansarinia et al. |
| 6,438,398 B1 | 8/2002 | Pflugfelder et al. |
| 6,458,157 B1 | 10/2002 | Suaning |
| 6,505,077 B1 | 1/2003 | Kast et al. |
| 6,526,318 B1 | 2/2003 | Ansarinia et al. |
| 6,535,766 B1 | 3/2003 | Thompson et al. |
| 6,537,265 B2 | 3/2003 | Thanavala et al. |
| 6,539,253 B2 | 3/2003 | Thompson et al. |
| 6,562,036 B1 | 5/2003 | Ellman et al. |
| 6,564,102 B1 | 5/2003 | Boveja |
| 6,578,579 B2 | 6/2003 | Burnside et al. |
| 6,604,528 B1 | 8/2003 | Duncan |
| 6,641,799 B2 | 11/2003 | Goldberg |
| 6,658,301 B2 | 12/2003 | Loeb et al. |
| 6,662,052 B1 | 12/2003 | Sarwal et al. |
| 6,684,879 B1 | 2/2004 | Coffee et al. |
| 6,701,189 B2 | 3/2004 | Fang et al. |
| 6,748,951 B1 | 6/2004 | Schmidt |
| 6,792,314 B2 | 9/2004 | Byers et al. |
| 6,829,508 B2 | 12/2004 | Schulman et al. |
| 6,853,858 B2 | 2/2005 | Shalev |
| 6,871,099 B1 | 3/2005 | Whitehurst et al. |
| 6,879,859 B1 | 4/2005 | Boveja |
| 6,885,888 B2 | 4/2005 | Rezai |
| 6,895,279 B2 | 5/2005 | Loeb et al. |
| 7,024,241 B1 | 4/2006 | Bornzin et al. |
| 7,067,307 B2 | 6/2006 | Hochleitner et al. |
| 7,069,084 B2 | 6/2006 | Yee |
| 7,117,033 B2 | 10/2006 | Shalev et al. |
| 7,142,909 B2 | 11/2006 | Greenberg et al. |
| 7,146,209 B2 | 12/2006 | Gross et al. |
| 7,169,163 B2 | 1/2007 | Becker |
| 7,190,998 B2 | 3/2007 | Shalev et al. |
| 7,225,032 B2 | 5/2007 | Schmeling et al. |
| 7,228,184 B2 | 6/2007 | Heath |
| 7,247,692 B2 | 7/2007 | Laredo |
| 7,317,947 B2 | 1/2008 | Wahlstrand et al. |
| 7,330,762 B2 | 2/2008 | Boveja et al. |
| 7,346,398 B2 | 3/2008 | Gross et al. |
| 7,369,897 B2 | 5/2008 | Boveja et al. |
| 7,442,191 B2 | 10/2008 | Hovda et al. |
| 7,460,911 B2 | 12/2008 | Cosendai et al. |
| 7,477,947 B2 | 1/2009 | Pines et al. |
| 7,502,652 B2 | 3/2009 | Gaunt et al. |
| 7,547,447 B2 | 6/2009 | Yiu et al. |
| 7,565,204 B2 | 7/2009 | Matei et al. |
| 7,599,737 B2 | 10/2009 | Yomtov et al. |
| 7,636,597 B2 | 12/2009 | Gross et al. |
| 7,650,186 B2 | 1/2010 | Hastings et al. |
| D613,408 S | 4/2010 | Gausmann et al. |
| D614,303 S | 4/2010 | Gausmann et al. |
| D614,774 S | 4/2010 | Gausmann et al. |
| 7,725,176 B2 | 5/2010 | Schuler et al. |
| 7,725,195 B2 | 5/2010 | Lima et al. |
| D617,443 S | 6/2010 | Grenon et al. |
| 7,758,190 B2 | 7/2010 | Korb et al. |
| 7,778,703 B2 | 8/2010 | Gross et al. |
| 7,778,711 B2 | 8/2010 | Ben-David et al. |
| 7,792,591 B2 | 9/2010 | Rooney et al. |
| 7,805,200 B2 | 9/2010 | Kast et al. |
| 7,805,202 B2 | 9/2010 | Kuzma et al. |
| 7,805,203 B2 | 9/2010 | Ben-David et al. |
| 7,809,442 B2 | 10/2010 | Bolea et al. |
| 7,835,794 B2 | 11/2010 | Greenberg et al. |
| 7,846,124 B2 | 12/2010 | Becker |
| 7,860,570 B2 | 12/2010 | Whitehurst et al. |
| 7,873,421 B2 | 1/2011 | Karell |
| D638,128 S | 5/2011 | Prokop et al. |
| 7,981,095 B2 | 7/2011 | Grenon et al. |
| 7,993,381 B2 | 8/2011 | Mac et al. |
| 8,002,783 B2 | 8/2011 | Vercellotti et al. |
| 8,019,419 B1 | 9/2011 | Panescu et al. |
| 8,080,047 B2 | 12/2011 | Yu |
| 8,145,322 B1 | 3/2012 | Yao et al. |
| 8,155,746 B2 | 4/2012 | Maltan et al. |
| 8,165,680 B2 | 4/2012 | Greenberg et al. |
| 8,204,591 B2 | 6/2012 | Ben-David et al. |
| 8,231,218 B2 | 7/2012 | Hong et al. |
| 8,251,983 B2 | 8/2012 | Larson et al. |

(56) References Cited

U.S. PATENT DOCUMENTS

| | | |
|---|---|---|
| 8,295,529 B2 | 10/2012 | Petersen et al. |
| D681,839 S | 5/2013 | Nathanson |
| 8,494,641 B2 | 7/2013 | Boling et al. |
| 8,626,298 B2 | 1/2014 | Simon |
| 8,676,324 B2 | 3/2014 | Simon et al. |
| 8,728,136 B2 | 5/2014 | Feldman |
| 8,918,181 B2 | 12/2014 | Ackermann et al. |
| 8,936,594 B2 | 1/2015 | Wolf et al. |
| 8,986,301 B2 | 3/2015 | Wolf et al. |
| 8,996,137 B2 | 3/2015 | Ackermann et al. |
| 9,079,042 B2 | 7/2015 | Tiedtke et al. |
| 9,095,723 B2 | 8/2015 | Ackermann et al. |
| 9,265,956 B2 | 2/2016 | Ackermann et al. |
| 9,440,065 B2 | 9/2016 | Ackermann et al. |
| 9,687,652 B2 | 6/2017 | Franke et al. |
| 9,737,712 B2 | 8/2017 | Franke et al. |
| 2001/0020177 A1 | 9/2001 | Gruzdowich et al. |
| 2002/0013594 A1 | 1/2002 | Dinger et al. |
| 2002/0035358 A1 | 3/2002 | Wang |
| 2002/0049290 A1 | 4/2002 | Vanderbilt et al. |
| 2002/0188331 A1 | 12/2002 | Fang et al. |
| 2003/0045909 A1 | 3/2003 | Gross et al. |
| 2003/0114899 A1 | 6/2003 | Woods et al. |
| 2003/0120323 A1 | 6/2003 | Meadows et al. |
| 2003/0130809 A1 | 7/2003 | Cohen et al. |
| 2003/0192784 A1 | 10/2003 | Zhou et al. |
| 2003/0233134 A1 | 12/2003 | Greenberg et al. |
| 2003/0233135 A1 | 12/2003 | Yee |
| 2004/0059466 A1 | 3/2004 | Block et al. |
| 2004/0098036 A1 | 5/2004 | Bergersen |
| 2004/0098067 A1 | 5/2004 | Ohta et al. |
| 2004/0138646 A1 | 7/2004 | Walla |
| 2004/0147973 A1 | 7/2004 | Hauser et al. |
| 2004/0151930 A1 | 8/2004 | Rouns et al. |
| 2004/0220644 A1 | 11/2004 | Shalev et al. |
| 2005/0004621 A1 | 1/2005 | Boveja et al. |
| 2005/0010250 A1 | 1/2005 | Schuler et al. |
| 2005/0101994 A1 | 5/2005 | Yamazaki et al. |
| 2005/0137276 A1 | 6/2005 | Yahiaoui et al. |
| 2005/0159790 A1 | 7/2005 | Shalev et al. |
| 2005/0197675 A1 | 9/2005 | David et al. |
| 2005/0251061 A1 | 11/2005 | Schuler et al. |
| 2005/0267542 A1 | 12/2005 | David et al. |
| 2005/0268472 A1 | 12/2005 | Bourilkov et al. |
| 2006/0004423 A1 | 1/2006 | Boveja et al. |
| 2006/0018872 A1 | 1/2006 | Tew et al. |
| 2006/0074450 A1 | 4/2006 | Boveja et al. |
| 2006/0089673 A1 | 4/2006 | Schultheiss et al. |
| 2006/0095077 A1 | 5/2006 | Tronnes et al. |
| 2006/0095108 A1 | 5/2006 | Chowdhury et al. |
| 2006/0100668 A1 | 5/2006 | Ben-David et al. |
| 2006/0107958 A1 | 5/2006 | Sleeper |
| 2006/0142822 A1 | 6/2006 | Tulgar |
| 2006/0161225 A1 | 7/2006 | Sormann et al. |
| 2006/0195169 A1 | 8/2006 | Gross et al. |
| 2006/0206155 A1 | 9/2006 | Ben-David et al. |
| 2006/0216317 A1 | 9/2006 | Reinhard et al. |
| 2006/0239482 A1 | 10/2006 | Hatoum et al. |
| 2006/0259098 A1 | 11/2006 | Erickson |
| 2006/0271024 A1 | 11/2006 | Gertner et al. |
| 2006/0271108 A1 | 11/2006 | Libbus et al. |
| 2007/0038267 A1 | 2/2007 | Shodo et al. |
| 2007/0060815 A1 | 3/2007 | Martin et al. |
| 2007/0060954 A1 | 3/2007 | Cameron et al. |
| 2007/0083245 A1 | 4/2007 | Lamensdorf et al. |
| 2007/0150034 A1 | 6/2007 | Rooney et al. |
| 2007/0219600 A1 | 9/2007 | Gertner et al. |
| 2007/0237797 A1 | 10/2007 | Peyman |
| 2007/0237825 A1 | 10/2007 | Levy et al. |
| 2007/0248930 A1 | 10/2007 | Brawn |
| 2007/0250119 A1 | 10/2007 | Tyler et al. |
| 2007/0250135 A1 | 10/2007 | Bartz-Schmidt et al. |
| 2007/0276314 A1 | 11/2007 | Becker |
| 2007/0276451 A1 | 11/2007 | Rigaux |
| 2007/0295327 A1 | 12/2007 | Bottomley |
| 2007/0299462 A1 | 12/2007 | Becker |
| 2008/0009897 A1 | 1/2008 | Duran Von Arx |
| 2008/0021515 A1 | 1/2008 | Horsager et al. |
| 2008/0082057 A1 | 4/2008 | Korb et al. |
| 2008/0082131 A1 | 4/2008 | Llanos |
| 2008/0109054 A1 | 5/2008 | Hastings et al. |
| 2008/0132933 A1 | 6/2008 | Gerber |
| 2008/0140141 A1 | 6/2008 | Ben-David et al. |
| 2008/0183242 A1 | 7/2008 | Tano et al. |
| 2008/0183243 A1 | 7/2008 | Shodo et al. |
| 2008/0269648 A1 | 10/2008 | Bock |
| 2009/0005835 A1 | 1/2009 | Greenberg et al. |
| 2009/0012573 A1 | 1/2009 | Karell et al. |
| 2009/0018582 A1 | 1/2009 | Ishikawa et al. |
| 2009/0024187 A1 | 1/2009 | Erickson et al. |
| 2009/0024189 A1 | 1/2009 | Lee et al. |
| 2009/0043185 A1 | 2/2009 | McAdams et al. |
| 2009/0056709 A1 | 3/2009 | Worsoff |
| 2009/0099600 A1 | 4/2009 | Moore et al. |
| 2009/0099623 A1 | 4/2009 | Bentwich et al. |
| 2009/0099626 A1 | 4/2009 | de Juan, Jr. et al. |
| 2009/0101139 A1 | 4/2009 | Karell |
| 2009/0124965 A1 | 5/2009 | Greenberg et al. |
| 2009/0138061 A1 | 5/2009 | Stephens et al. |
| 2009/0156581 A1 | 6/2009 | Dillon et al. |
| 2009/0157142 A1 | 6/2009 | Cauller et al. |
| 2009/0157145 A1 | 6/2009 | Cauller |
| 2009/0157147 A1 | 6/2009 | Cauller et al. |
| 2009/0192571 A1 | 7/2009 | Stett et al. |
| 2009/0204142 A1 | 8/2009 | Becker |
| 2009/0241840 A1 | 10/2009 | Mills |
| 2009/0264966 A1 | 10/2009 | Blum et al. |
| 2009/0281594 A1 | 11/2009 | King et al. |
| 2009/0281596 A1 | 11/2009 | King et al. |
| 2009/0299418 A1 | 12/2009 | Shalev et al. |
| 2009/0306738 A1 | 12/2009 | Weiss et al. |
| 2010/0076423 A1 | 3/2010 | Muller |
| 2010/0087896 A1 | 4/2010 | McCreery |
| 2010/0094280 A1 | 4/2010 | Muller |
| 2010/0139002 A1 | 6/2010 | Walker et al. |
| 2010/0152708 A1 | 6/2010 | Li et al. |
| 2010/0161004 A1 | 6/2010 | Najafi et al. |
| 2010/0168513 A1 | 7/2010 | Pless et al. |
| 2010/0179468 A1 | 7/2010 | Becker |
| 2010/0274164 A1 | 10/2010 | Juto |
| 2010/0274224 A1 | 10/2010 | Jain et al. |
| 2010/0274313 A1 | 10/2010 | Boling et al. |
| 2010/0280509 A1 | 11/2010 | Muller et al. |
| 2010/0288275 A1 | 11/2010 | Djupesland et al. |
| 2010/0318159 A1 | 12/2010 | Aghassian et al. |
| 2011/0021975 A1 | 1/2011 | Covello |
| 2011/0077551 A1 | 3/2011 | Videbaek |
| 2011/0093043 A1 | 4/2011 | Torgerson et al. |
| 2011/0151393 A1 | 6/2011 | Frey, II et al. |
| 2011/0152969 A1 | 6/2011 | Zehnder et al. |
| 2011/0202121 A1 | 8/2011 | Wen |
| 2011/0218590 A1 | 9/2011 | Degiorgio et al. |
| 2011/0234971 A1 | 9/2011 | Yeh |
| 2011/0275734 A1 | 11/2011 | Scales et al. |
| 2011/0276107 A1 | 11/2011 | Simon et al. |
| 2011/0282251 A1 | 11/2011 | Baker et al. |
| 2011/0295336 A1 | 12/2011 | Sharma et al. |
| 2011/0313330 A1 | 12/2011 | Loushin et al. |
| 2011/0313481 A1 | 12/2011 | De Vos |
| 2012/0053648 A1 | 3/2012 | Neher et al. |
| 2012/0130398 A1 | 5/2012 | Ackermann et al. |
| 2012/0197338 A1 | 8/2012 | Su et al. |
| 2012/0232615 A1 | 9/2012 | Barolat et al. |
| 2012/0232618 A1 | 9/2012 | Feldman |
| 2012/0234332 A1 | 9/2012 | Shantha |
| 2012/0253249 A1 | 10/2012 | Wilson et al. |
| 2012/0298105 A1 | 11/2012 | Osorio et al. |
| 2012/0315329 A1 | 12/2012 | Ahn et al. |
| 2012/0316557 A1 | 12/2012 | Sartor et al. |
| 2012/0323214 A1 | 12/2012 | Shantha |
| 2012/0323227 A1 | 12/2012 | Wolf et al. |
| 2012/0323232 A1 | 12/2012 | Wolf et al. |
| 2012/0330376 A1 | 12/2012 | Flynn et al. |
| 2013/0006095 A1 | 1/2013 | Jenkins et al. |

(56) References Cited

U.S. PATENT DOCUMENTS

| | | |
|---|---|---|
| 2013/0006326 A1 | 1/2013 | Ackermann et al. |
| 2013/0053733 A1 | 2/2013 | Korb et al. |
| 2013/0053737 A1 | 2/2013 | Scerbo |
| 2013/0065765 A1 | 3/2013 | Selifonov et al. |
| 2013/0158451 A1 | 6/2013 | Juto et al. |
| 2013/0158626 A1 | 6/2013 | DeGiorgio et al. |
| 2013/0172790 A1 | 7/2013 | Badawi |
| 2013/0178937 A1 | 7/2013 | Vassallo et al. |
| 2013/0253387 A1 | 9/2013 | Bonutti et al. |
| 2013/0261706 A1 | 10/2013 | Mirro et al. |
| 2013/0270491 A1 | 10/2013 | Park et al. |
| 2013/0274831 A1 | 10/2013 | Otto et al. |
| 2013/0304154 A1 | 11/2013 | Goodman et al. |
| 2013/0310887 A1 | 11/2013 | Curtis |
| 2014/0012182 A1 | 1/2014 | Shantha et al. |
| 2014/0081353 A1 | 3/2014 | Cook et al. |
| 2014/0088463 A1 | 3/2014 | Wolf et al. |
| 2014/0163580 A1 | 6/2014 | Tischendorf et al. |
| 2014/0214120 A1 | 7/2014 | Simon et al. |
| 2014/0277429 A1 | 9/2014 | Kuzma et al. |
| 2014/0316310 A1 | 10/2014 | Ackermann et al. |
| 2014/0316396 A1 | 10/2014 | Wolf et al. |
| 2014/0316485 A1 | 10/2014 | Ackermann et al. |
| 2014/0362339 A1 | 12/2014 | Imafuku |
| 2014/0371812 A1 | 12/2014 | Ackermann et al. |
| 2015/0088156 A1 | 3/2015 | Ackermann et al. |
| 2015/0238754 A1 | 8/2015 | Loudin et al. |
| 2015/0335900 A1 | 11/2015 | Ackermann et al. |
| 2016/0114163 A1 | 4/2016 | Franke et al. |
| 2016/0158548 A1 | 6/2016 | Ackermann et al. |
| 2016/0367795 A1 | 12/2016 | Ackermann et al. |
| 2016/0367806 A1 | 12/2016 | Kahook |
| 2017/0049619 A1 | 2/2017 | Kahook |
| 2017/0157401 A1 | 6/2017 | Loudin et al. |

FOREIGN PATENT DOCUMENTS

| | | |
|---|---|---|
| EM | 2199000-0001 | 3/2013 |
| EP | 0 109 935 A1 | 5/1984 |
| EP | 1 497 483 | 1/2005 |
| EP | 1 651 307 | 5/2006 |
| EP | 1 919 553 | 5/2008 |
| EP | 1 958 661 A1 | 8/2008 |
| EP | 2 205 193 | 7/2010 |
| EP | 2 205 314 | 7/2010 |
| GB | 2 129 690 B | 3/1987 |
| GB | 2 456 002 A | 7/2009 |
| JP | 2002-325851 A | 11/2002 |
| JP | 2002-539859 A | 11/2002 |
| JP | 2005-052461 A | 3/2005 |
| JP | 2006-515900 A | 6/2006 |
| JP | 2007-044323 A | 2/2007 |
| JP | 2007-528751 A | 10/2007 |
| JP | 2008-183248 A | 8/2008 |
| JP | 2008-541850 A | 11/2008 |
| JP | 2010-505563 A | 2/2010 |
| JP | 2010-051562 A | 3/2010 |
| JP | 2010-537777 A | 12/2010 |
| JP | 2011-030734 A | 2/2011 |
| WO | WO-00/56393 A1 | 9/2000 |
| WO | WO-00/62672 A1 | 10/2000 |
| WO | WO-2003/087433 A1 | 10/2003 |
| WO | WO-2004/043217 A2 | 5/2004 |
| WO | WO-2004/043217 A3 | 5/2004 |
| WO | WO-2005/007234 A2 | 1/2005 |
| WO | WO-2005/007234 A3 | 1/2005 |
| WO | WO-2005/030025 A2 | 4/2005 |
| WO | WO-2005/030025 A3 | 4/2005 |
| WO | WO-2005/060984 A1 | 7/2005 |
| WO | WO-2006/127366 A1 | 11/2006 |
| WO | WO-2008/156501 A2 | 12/2008 |
| WO | WO-2008/156501 A3 | 12/2008 |
| WO | WO-2009/035571 A2 | 3/2009 |
| WO | WO-2009/035571 A3 | 3/2009 |
| WO | WO-2009/070709 A1 | 6/2009 |
| WO | WO-2010/027743 A1 | 3/2010 |
| WO | WO-2010/099818 A1 | 9/2010 |
| WO | WO-2011/011373 A1 | 1/2011 |
| WO | WO-2012/068247 A1 | 5/2012 |
| WO | WO-2012/139063 A2 | 10/2012 |
| WO | WO-2012/139063 A3 | 10/2012 |
| WO | WO-2013/055940 A2 | 4/2013 |
| WO | WO-2013/055940 A3 | 4/2013 |
| WO | WO-2013/157320 A1 | 10/2013 |
| WO | WO-2013/165697 A1 | 11/2013 |
| WO | WO-2013/166353 A1 | 11/2013 |
| WO | WO-2014/172693 A2 | 10/2014 |
| WO | WO-2014/172693 A3 | 10/2014 |
| WO | WO-2015/130707 A2 | 9/2015 |
| WO | WO-2015/130707 A3 | 9/2015 |
| WO | WO-2016/065213 A1 | 4/2016 |

OTHER PUBLICATIONS

Amparo (2013). "Topical Interleukin 1 Receptor Antagonist for Treatment of Dry Eye Disease," JAMA Ophth. 131(6):E1-E9.

Anonymous (2007). "The epidemiology of dry eye disease: report of the Epidemiology Subcommittee of the International Dry Eye WorkShop (2007)," Ocul. Surf. 5(2):93-107.

Bajpai et al. (2012). "Preparation, Characterization and Water Uptake Behavior of Polysaccharide Based Nanoparticles," Prog. Nanotech. Nanomat. 1(1):9-17.

Baraniuk et al. (2007). "Nasonasal Reflexes, the Nasal Cycle, and Sneeze," Curr. Allergy and Asthma Reports 7:105-111.

Baroody FM, Foster KA, Markaryan A, et al. Nasal ocular reflexes and eye symptoms in patients with allergic rhinitis. Ann Allergy Asthma Immunol 2008;100:194-199.

Baroody FM, Shenaq D, DeTineo M, et al. Fluticasone furoate nasal spray reduces the nasal-ocular reflex: a mechanism for the efficacy of topical steroids in controlling allergic eye symptoms. J Allergy Clin Immunol 2000;123:1342-1348.

Boberg-Ans J. (1955). "Experience in clinical examination of corneal sensitivity: corneal sensitivity and the naso-lacrimal reflex after retrobulbar anaesthesia," Br. J. Ophthalmol. 39(12):705-726.

Calonge (2001). "The Treatment of Dry Eye," Survey Ophth. 45(2):S227-S239.

Cipriano et al. (2014). "Superabsorbent Hydrogels That Are Robust and Highly Stretchable," Am. Chem Soc. 47(13):4445-4452.

Corrected Notice of Allowance dated Feb. 23, 2015, for U.S. Appl. No. 14/256,915, filed Apr. 18, 2014, 2 pages.

Corrected Notice of Allowance dated Jun. 9, 2017, for U.S. Appl. No. 14/920,860, filed Oct. 22, 2015, 2 pages.

Corrected Notice of Allowance dated Jul. 17, 2017, for U.S. Appl. No. 15/256,392, filed Sep. 2, 2016, 2 pages.

Dart et al. (2002). "Effects of 25% Propylene Glycol Hydrogel (Solugel) on Second Intention Wound Healing in Horses," Vet. Surg. 31(4):309-313.

Drummond PD. Lacrimation and cutaneous vasodilatation in the face induced by painful stimulation of the nasal ala and upper lip. J Auton Nerv Syst 1995;51:109-16.

Elsby et al. (1967). "Lacrimal Secretion in the Cat," Br. J. Pharm. Chemother. 29(1):1-7.

Extended European Search Report dated Nov. 18, 2016, for EP Application No. 14 785 631.4, filed on Apr. 18, 2014, 7 pages.

Extended European Search Report dated Sep. 19, 2017, for EP Application No. 15 754 827.2, filed on Feb. 24, 2015, 9 pages.

Final Office Action for U.S. Appl. No. 14/256,916, dated Apr. 8, 2015, 16 pages.

Final Office Action for U.S. Appl. No. 14/313,937 dated Apr. 29, 2015, 13 pages.

Final Office Action for U.S. Appl. No. 14/630,471, dated Sep. 26, 2016, 22 pages.

Final Office Action for U.S. Appl. No. 14/256,916, dated Aug. 19, 2016, 19 pages.

Final Office Action dated Sep. 23, 2016, for U.S. Appl. No. 14/809,109, filed Jul. 24, 2015, 10 pages.

Final Office Action dated Feb. 1, 2017, for U.S. Appl. No. 14/920,852, filed Oct. 22, 2015, 20 pages.

(56) References Cited

OTHER PUBLICATIONS

Friedman et al. (2016). "A nonrandomized, open-label study to evaluate the effect of nasal stimulation on tear production in subjects with dry eye disease," Clin. Ophthal. 10:795-804.
Fujisawa et al. (2002). "The Effect of Nasal Mucosal Stimulation on Schirmer Tests in Sjogren's Syndrome and Dry Eye Patients," Lac. Gland Tear Film Dry Eye Syndrome 3 506:1221-1226.
Gupta et al. (1997). "Nasolacrimal Stimulation of Aqueous Tear Production," Cornea 16(6):645-648.
Heigle TJ, Pflugfelder SC. Aqueous tear production in patients with neurotrophic keratitis. Cornea 1996;15:135-8.
Holzer P. Capsaicin: cellular targets, mechanisms of action, and selectivity for thin sensory neurons. Pharmacol Rev 1991;43:143-201.
Ikemura et al. (2008). "UV-VIS Spectra and Photoinitiation Behaviors of Acylphosphine Oxide and Bisacylphosphine Oxide Derivatives in unfilled, Light-Cured Dental Resins," Dent. Mat. J. 27:765-774.
International Search Report and Written Opinion received for PCT Application No. PCT/US2015/042130, dated Oct. 28, 2015.
International Search Report and Written Opinion received for PCT Patent Application No. PCT/US2014/034733, dated Dec. 5, 2014.
International Search Report and Written Opinion received for PCT Patent Application No. PCT/US2015/017379, dated Jul. 24, 2015.
International Search Report and Written Opinion received for PCT Patent Application No. PCT/US2015/057023, dated Mar. 4, 2016.
International Search Report dated Feb. 10, 2016, for PCT Patent Application No. PCT/US2015/57021, filed on Oct. 22, 2015, 4 pages.
International Search Report dated Aug. 7, 2017, for PCT Patent Application No. PCT/US2017/30617, filed on May 2, 2017, 2 pages.
Krupin T, Cross DA, Becker B. Decreased basal tear production associated with general anesthesia. Arch Ophthalmol 1977;95:107-108.
Lora et al. (2009). "Lacrimal Nerve Stimulation by a Neurostimulator for Tear Production," Invest. Ophth. Vis. Science 50(13):172.
Loth S, Bende M. Effect of nasal anaesthesia on lacrimal function after nasal allergen challenge. Clin Exp Allergy 1994;24:375-376.
Meng, I.D. et al. (2013). "The role of corneal afferent neurons in regulating tears under normal and dry eye conditions," Exp. Eye Res. 117:79-87.
Mallepally et al. (2013). "Superabsorbent Alginate Aerogels," J. Supercritical Fluids 79:1-5.
Non-Final Office Action received for U.S. Appl. No. 14/256,915, dated Aug. 13, 2014, 11 pages.
Non-Final Office Action received for U.S. Appl. No. 14/256,916, dated Sep. 12, 2014, 24 pages.
Non-Final Office Action received for U.S. Appl. No. 14/313,937, dated Nov. 19, 2014, 12 pages.
Non-Final Office Action dated Jun. 14, 2016, for U.S. Appl. No. 14/630,471, filed Feb. 24, 2015, 24 pages.
Non-Final Office Action received for U.S. Appl. No. 14/809,109, dated Apr. 8, 2016, 8 pages.
Non-Final Office Action Received for U.S. Appl. No. 14/920,860, dated Aug. 17, 2016, 11 pages.
Non-Final Office Action received for U.S. Appl. No. 14/256,916, dated Nov. 19, 2015, 20 pages.
Non-Final Office Action Received for U.S. Appl. No. 14/313,937, dated Oct. 6, 2015, 7 pages.
Non-Final Office Action Received for U.S. Appl. No. 14/920,852, dated Aug. 1, 2016, 20 pages.
Non-Final Office Action dated Sep. 30, 2016, for U.S. Appl. No. 15/256,392, filed Sep. 2, 2016, 14 pages.
Non-Final Office Action dated Feb. 14, 2017, for U.S. Appl. No. 14/630,471, filed Feb. 24, 2015, 23 pages.
Non-Final Office Action dated Apr. 19, 2017, for U.S. Appl. No. 14/256,916, filed Apr. 18, 2014, 19 pages.
Non-Final Office Action dated Jul. 17, 2017, for U.S. Appl. No. 15/598,063, filed May 17, 2017, 9 pages.
Non-Final Office Action dated Jul. 31, 2017, for U.S. Appl. No. 14/920,852, filed Oct. 22, 2015, 18 pages.
Notice of Allowance received for U.S. Appl. No. 14/256,915, dated Nov. 26, 2014, 7 pages.
Notice of Allowance received for U.S. Appl. No. 14/313,937, dated Feb. 19, 2016, 8 pages.
Notice of Allowance received for U.S. Appl. No. 14/313,937, dated May 2, 2016, 7 pages.
Notice of Allowability dated Dec. 19, 2016, for U.S. Appl. No. 14/809,109, filed Jul. 24, 2015, 8 pages.
Notice of Allowance dated Jan. 19, 2017, for U.S. Appl. No. 14/920,860, filed Oct. 22, 2015, 5 pages.
Notice of Allowance dated Mar. 21, 2017, for U.S. Appl. No. 14/809,109, filed Jul. 24, 2015, 8 pages.
Notice of Allowance dated Apr. 17, 2017, for U.S. Appl. No. 15/256,392, filed Sep. 2, 2016, 10 pages.
Notice of Allowance dated Apr. 20, 2017, for U.S. Appl. No. 14/920,860, filed Oct. 22, 2015, 5 pages.
Notice of Allowance dated May 26, 2017, for U.S. Appl. No. 14/630,471, filed Feb. 24, 2015, 5 pages.
Pasqui et al. (2012). "Polysaccharide-Based Hydrogels: The Key Role of Water in Affecting Mechanical Properties," Polymers 4(3):1517-1534.
Philip G, Baroody FM, Proud D, et al. The human nasal response to capsaicin. J Allergy Clin Immunol 1994;94:1035-1045.
Roessler et al. (2009). "Implantation and Explantation of a Wireless Epiretinal Retina Implant Device: Observations During the EPIRET3 Prospective Clinical Trial," Invest. Ophthal. Visual Science 50(6):3003-3008.
Ruskell (2004). "Distribution of Pterygopalatine Ganglion Efferents to the Lacrimal Gland in Man," Exp. Eye Res. 78(3):329-335.
Sall et al. (2000). "Two Multicenter, Randomized Studies of the Efficacy and Safety of Cyclosporine Ophthalmic Emulsion in Moderate to Severe Dry Eye Disease," Ophth. 107(4):631-639.
Shaari et al. (1995). "Rhinorrhea is decreased in dogs after nasal application of botulinum toxin," Oto. Head Neck Surg. 112(4):566-571.
Stjernschantz et al. (1979). "Electrical Stimulation of the Fifth Cranial Nerve in Rabbits: Effects on Ocular Blood Flow, Extravascular Albumin Content and Intraocular Pressure," Exp. Eye Res. 28(2):229-238.
Stjernschantz et al. (1980). "Vasomotor effects of Facial Nerve Stimulation: Noncholinergic Vasodilation in the eye," Acta Phys. Scand. 109(1):45-50.
Tsubota (1991). "The Importance of the Schirmer Test with Nasal Stimulation," Am. J. Ophth. 111:106-108.
Velikay-Parel et al. (2011). "Perceptual Threshold and Neuronal Excitability as Long-Term Safety Evaluation in Retinal Implants," Invest. Opht. Visual Science E-Abstract 2590, 2 pages.
Written Opinion received for PCT Patent Application No. PCT/US2015/57021, dated Feb. 10, 2016, 5 pages.
Written Opinion of the International Search Authority dated Aug. 7, 2017, for PCT Patent Application No. PCT/US2017/30617, filed on May 2, 2017, 4 pages.
Zilstorff-Pedersen (1965). "Quantitative Measurements of the Nasolacrimal Reflex," Arch. Oto. 81:457-462.
Extended European Search Report dated Jan. 8, 2018, for EP Application No. 15 824 539.9, filed Jul. 24, 2015, 6 pages.
Final Office Action dated Nov. 8, 2017, for U.S. Appl. No. 14/256,916, filed Apr. 18, 2014, 21 pages.
Final Office Action dated Dec. 20, 2017, for U.S. Appl. No. 14/920,852, filed Oct. 22, 2015, 18 pages.
Non-Final Office Action dated Dec. 28, 2017, for U.S. Appl. No. 15/676,910, filed Aug. 14, 2017, 10 pages.

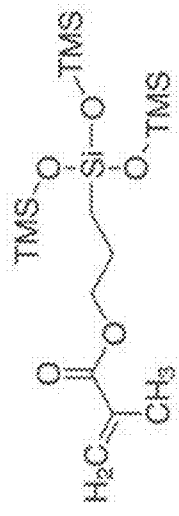
$H_2C=C(CH_3)CO_2CH_2CH_2OSi(CH_3)_3$
2 (trimethylsilyloxy) ethyl methacrylate
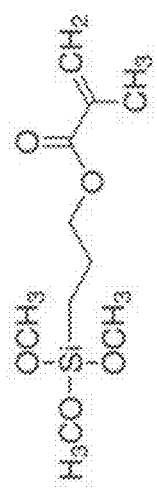
$H_2C=C(CH_3)CO_2(CH_2)_3Si(OSi(CH_3)_3)_3$
TMS = Trimethylsilyl
(3-methacryloyloxypropyl) tris
(trimethylsiloxy)silane
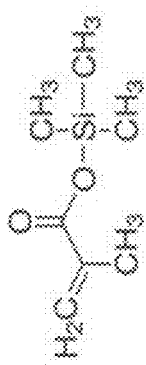
$H_2C=C(CH_3)CO_2Si(CH_3)_3$
Trimethylsilyl methacrylate
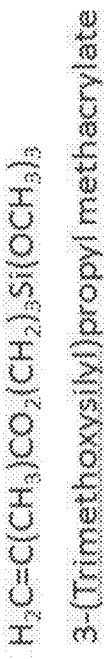
$H_2C=C(CH_3)CO_2(CH_2)_3Si(OCH_3)_3$
3-(Trimethoxysilyl)propyl methacrylate
FIG. 6

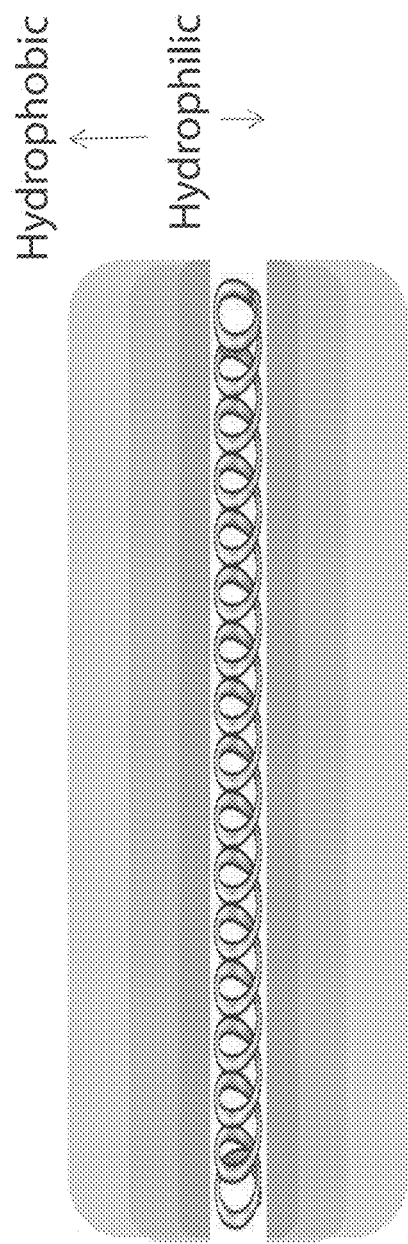

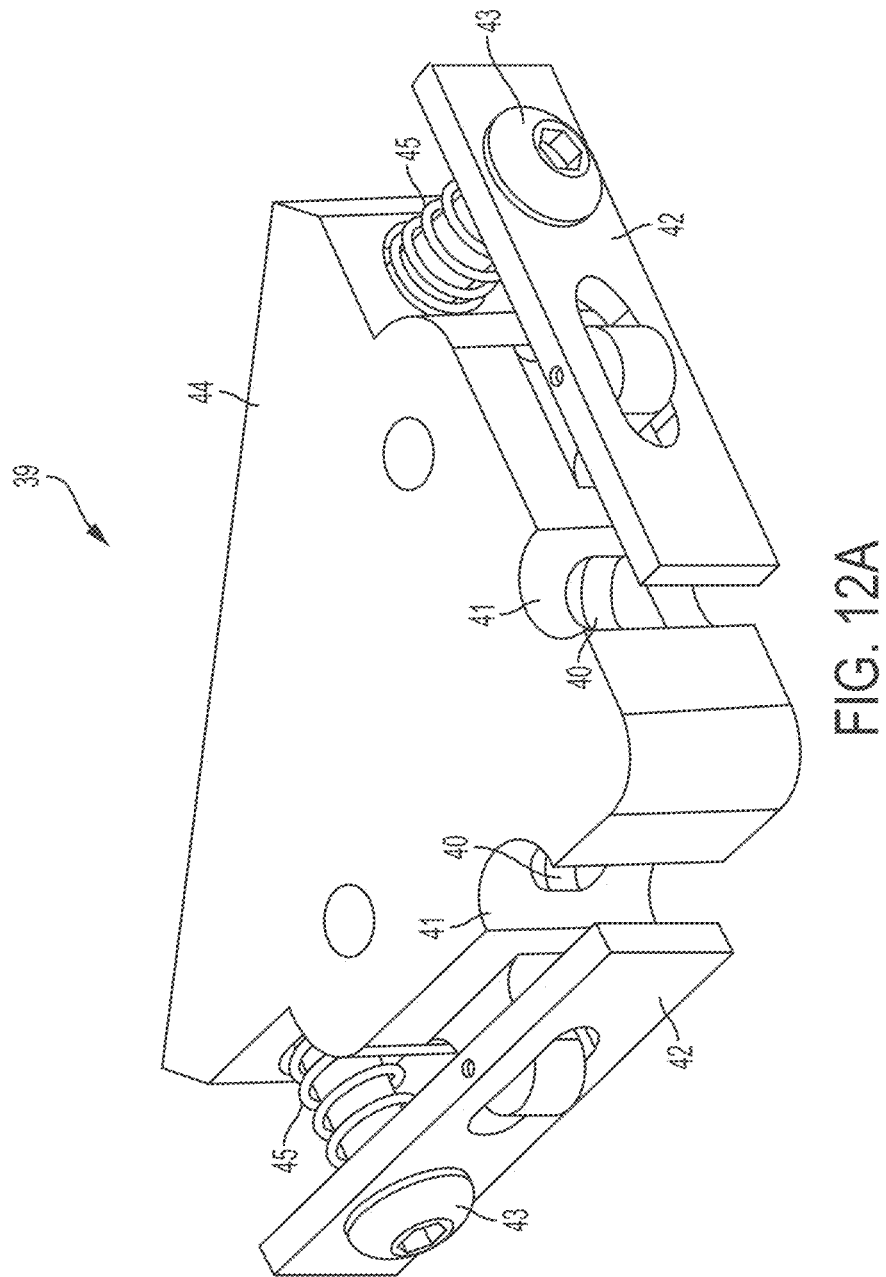

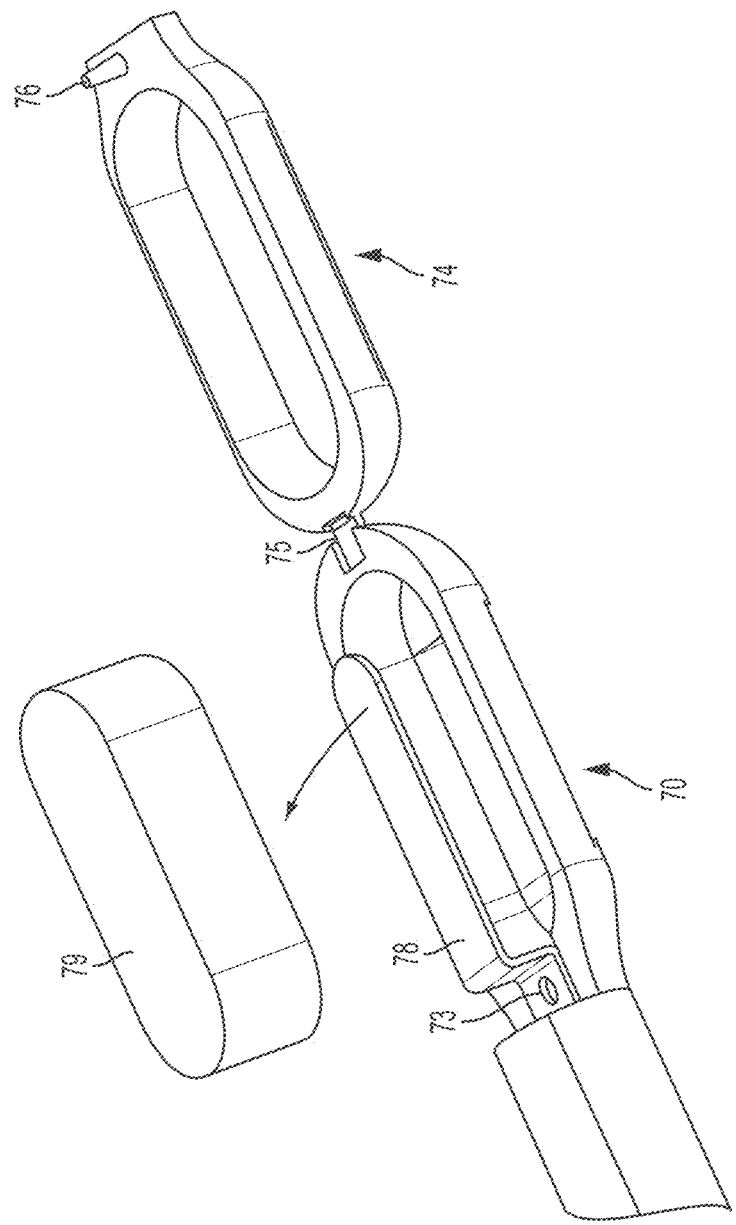

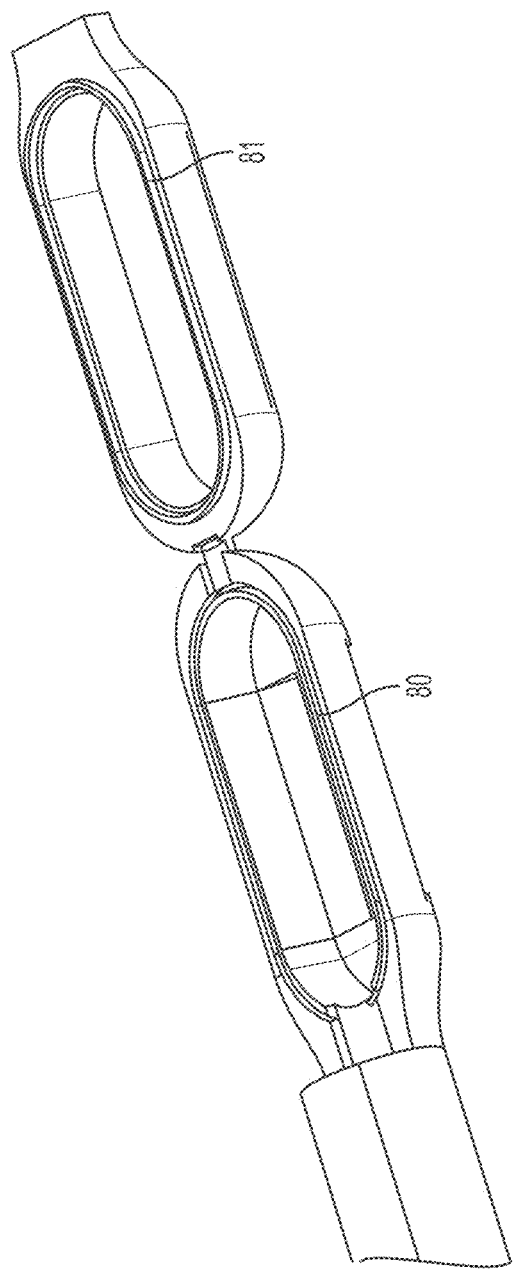

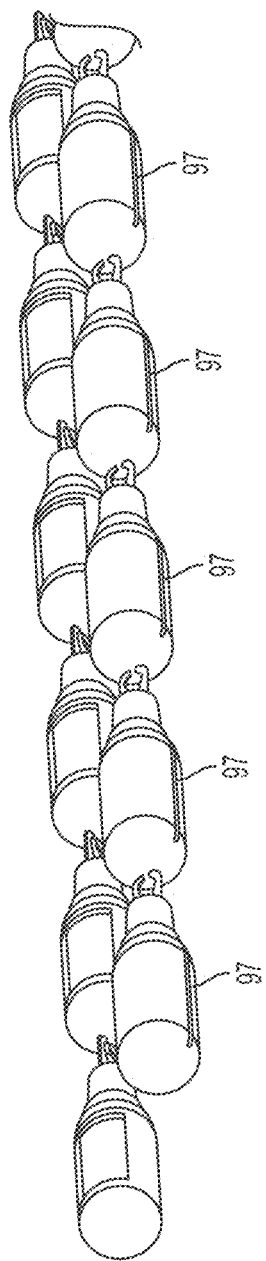

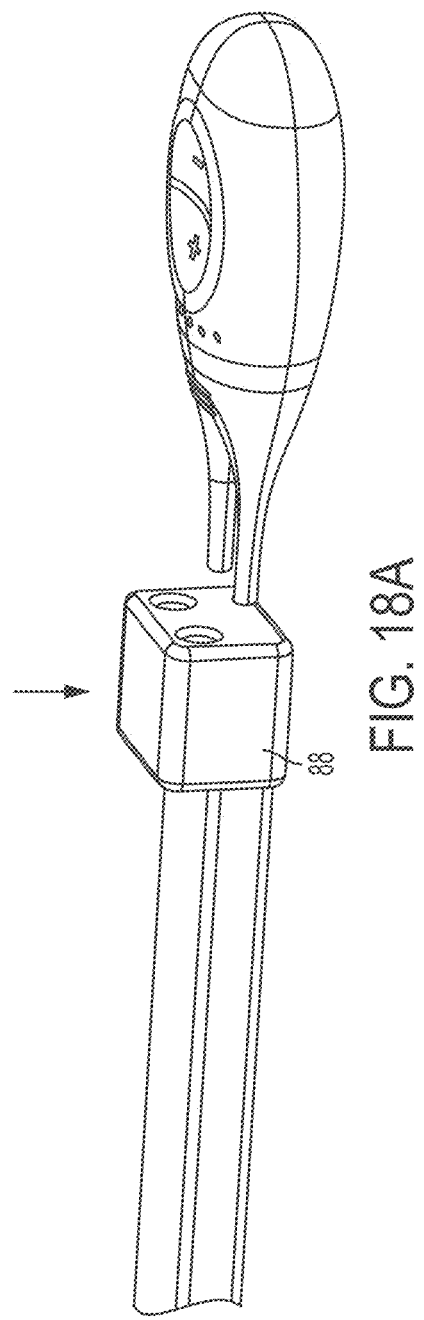

| Hours of Extraction | Sleeve resistance of SB1 ($\times 10^3 \Omega$) | Sleeve resistance of SB2 ($\times 10^3 \Omega$) |
|---|---|---|
| 1 | 175 | 146 |
| 2 | 149.7 | 33.4 |
| 3 | 29.6 | 9.1 |
| 4 | 11.9 | 4.7 |
| 8 | 1.8 | 1.6 |
| 12 | 0.9 | 1.1 |
| 24 | 0.6 | 0.7 |
| 48 | 0.5 | 0.6 |
| 72 | 0.4 | 0.4 |

| Time (Hrs) | 42-01 TARE 0.39843 Total wt | Gel Mass | 42-02 0.39464 Total wt | Gel Mass | 42-03 0.39238 Total wt | Gel Mass | 42-04 0.39318 Total wt | Gel Mass | 42-05 0.39262 Total wt | Gel Mass |
|---|---|---|---|---|---|---|---|---|---|---|
| 0 | 0.44515 | 0.04672 | 0.4464 | 0.05176 | 0.44163 | 0.04925 | 0.44419 | 0.05101 | 0.44007 | 0.04745 |
| 4 | 0.46014 | 0.06171 | 0.46721 | 0.07257 | 0.46015 | 0.06777 | 0.46313 | 0.06995 | 0.46349 | 0.07087 |
| 8 | 0.46184 | 0.06341 | 0.4674 | 0.07276 | 0.46226 | 0.06988 | 0.46478 | 0.0716 | 0.46526 | 0.07264 |
| 12 | 0.46308 | 0.06465 | 0.46792 | 0.07328 | 0.46322 | 0.07084 | 0.46654 | 0.07336 | 0.46675 | 0.07413 |
| 24 | 0.46566 | 0.06723 | 0.47008 | 0.07544 | 0.46573 | 0.07335 | 0.46966 | 0.07648 | 0.46948 | 0.07686 |
| 48 | 0.46681 | 0.06838 | 0.47166 | 0.07702 | 0.46686 | 0.07448 | 0.47008 | 0.0769 | 0.47137 | 0.07875 |
| 72 | 0.46813 | 0.0697 | 0.47163 | 0.07699 | 0.46767 | 0.07529 | 0.47081 | 0.07763 | 0.4712 | 0.07858 |
| 144 | 0.46982 | 0.07139 | 0.50563 | 0.11099 | 0.46972 | 0.07734 | 0.47283 | 0.07965 | 0.47388 | 0.08126 |
| 192 | 0.4682 | 0.06977 | 0.50428 | 0.10964 | 0.46913 | 0.07675 | 0.47096 | 0.07778 | 0.47399 | 0.08137 |
| 240 | 0.46922 | 0.07079 | 0.5047 | 0.11006 | 0.46979 | 0.07741 | 0.47233 | 0.07915 | 0.47457 | 0.08195 |

POLYMER FORMULATIONS FOR NASOLACRIMAL STIMULATION

CROSS-REFERENCE TO RELATED APPLICATIONS

This application is a continuation of U.S. application Ser. No. 14/630,471, filed on Feb. 24, 2015, which issued as U.S. Pat. No. 9,770,583 on Sept. 26, 2017, which claims priority to U.S. Provisional Application No. 61/944,340, filed on Feb. 25, 2014, U.S. Provisional Application No. 62/027,139, filed on Jul. 21, 2014, U.S. Provisional Application No. 62/035,221, filed on Aug. 8, 2014, and U.S. Provisional Application No. 62/067,350, filed on Oct. 22, 2014. Each of the aforementioned disclosures is hereby incorporated by reference in its entirety.

FIELD

Described herein are polymer formulations that provide electrical contact between an electrode and a nasal or sinus tissue. Specifically, hydrogel formulations that are cross-linked using UV radiation are described. Methods of manufacturing the hydrogels and methods of treating dry eye with nasal stimulator devices including the hydrogels are also described.

BACKGROUND

Dry eye disease is a major eye condition throughout the world for which no permanent cure is currently available. For example, it has been estimated that the current average annual cost of treating dry eye disease amounts to $850 per person (Yu, J., Andre, C. V., and Fairchild, C. J. "The economic burden of dry eye disease in the United States: a decision tree analysis." *Cornea* 30 4 (2011): 379-387). Epidemiological estimates of frequency of incidence of dry eye disease vary widely, depending on the symptoms being monitored. For example, Friedman reports that the incidence of dry eye disease ranges from 5% to 35% globally (Friedman, N. "Impact of dry eye disease and impact on quality of life." *Current Opinion in Ophthalmology* 21 (2010): 310-316).

Current treatments include the use of lubricants (e.g., hydroxymethyl and sodium carboxypropyl cellulose, generally known as artificial tears), anti-inflammatory therapies (e.g., corticosteroids and immunomodulators such as cyclosporin), tear retention therapies (e.g., punctal plugs), and treatment of underlying causes such as meibomian gland dysfunction, lid abnormalities, etc. These treatments have been shown to have a mild to moderate improvement in the quality of life of the patient. For example, the Lacrisert® ophthalmic insert (Aton Phama, Lawrenceville, N.J.), a hydroxypropyl cellulose ophthalmic insert placed in the inferior eyelid cul-de-sac, was shown to have a 21% improvement in ocular surface disease index scores by McDonald, et al. (McDonald, M. B., D'Aversa, Perry H. D., et al. "Hydroxypropyl cellulose ophthalmic inserts (Lacrisert) reduce the signs and symptoms of dry eye syndrome." *Trans Am Ophthalmol Soc* 107 (2009): 214-222). However, these treatments often require multiple administrations per day, and typically do not prevent long term damage to the ocular surface, often caused by the chemical being administered. For example, it is known that preservatives (e.g., benzalkonium chloride) can cause damage to the ocular surface and cause irritation.

Accordingly, the development of alternative treatments for dry eye syndrome would be useful. In particular, treatments that do not involve long term administration of drug therapy would be beneficial. Treatments with simplified administration regimens would further be desirable.

SUMMARY

Described herein are polymer formulations for facilitating electrical stimulation of nasal or sinus tissue. The polymer formulations may form hydrogels that are prepared by a cross-linking process using UV or visible light. In some applications the hydrogels may be included as a component of devices (referred to here and throughout as nasal stimulator devices or nasostimulator devices) that electrically stimulate the lacrimal gland via a nasal or sinus afferent nerve in patients suffering from dry eye to improve tear production. The nasal stimulators may be used to treat dry eye of varying etiology. For example, they may be used to treat dry eye due to age, hormonal imbalances, side effects of medication, and medical conditions such as Sjogren's syndrome, lupus, scleroderma, thyroid disorders, etc.

Generally, the polymer formulations may form electrically conductive hydrogels comprised of various monomers. The monomers may be the same or different. The electrically conductive hydrogel formulations may include a first monomer; a second monomer; and a photoinitiator. The use of an acrylate monomer, a silane monomer, an acrylic terminated silane monomer, and/or an acrylic terminated siloxane monomer as the first monomer or sole monomer component of the formulation may be beneficial. The electrically conductive hydrogel will typically have one or more characteristics that adapt it for use with a nasal stimulator device. In some instances, the electrically conductive hydrogel is a hydrogel with high water content, as further described below. As used herein and throughout, the terms "formulation," "polymer formulation," "hydrogel formulation," "electrically conductive hydrogel formulation," "hydrogel," and "electrically conductive hydrogel" can refer to formulations comprising monomers and mixtures of monomers, before or after they have been cured, depending on the context of how the term is used. It is understood that either the uncured or cured formulations comprise monomers or a mixture of monomers.

Processes for producing electrically conductive hydrogels are also described herein. The processes may generally include the steps of mixing a first monomer, a second monomer, and a photoinitiator to prepare a formulation, where the first monomer is an acrylate monomer; and irradiating the formulation with UV radiation to cross-link the formulation. The formulation may be cross-linked by covalent bonds or ionic bonds to form the hydrogel.

Methods for manufacturing the nasal stimulator devices, including shaping of the conductive hydrogel, e.g., to form a bulge that may enhance contact of the hydrogel to nasal mucosa, and attaching the tip assembly with or without the shaped hydrogel to a base unit of the nasal stimulator devices, are also described herein. The methods for shaping the hydrogel are further described below and may comprise dipping the tip assembly into the hydrogel, using the tip assembly to scoop hydrogel therein, molding or casting the hydrogel, or dispensing the hydrogel into the tip assembly through a window disposed therethrough. The tip assemblies comprising the shaped hydrogel may be stored in a dispensing cassette for later attachment to a base unit of the nasal stimulator device, as further described below.

In addition, described herein are methods for stimulating the nasal cavity or the lacrimal gland comprising placing an arm of a nasal stimulator device against a nasal or a sinus tissue, the arm having a distal end and an electrically conductive hydrogel disposed at the distal end; and activating the nasal stimulator device to provide electrical stimulation to the nasal or the sinus tissue. The electrically conductive hydrogel is typically used to facilitate an electrical connection between the nasal stimulator device and the nasal or the sinus tissue. These methods may be used to treat dry eye.

BRIEF DESCRIPTION OF THE DRAWINGS

FIG. 3A shows a perspective view of the stimulator electrode surrounded by an opaque polymeric sleeve. FIG. 3B is a cross-sectional view of the stimulator electrode in FIG. 3A showing an electrically conductive polymer disposed within the tip portion. FIG. 3B depicts a stylized view of the stimulator electrode in FIG. 3A where the conductive polymer forms a shell around the distal end of the polymeric sleeve.

FIG. 6 depicts the chemical structure of exemplary acrylic terminated silane and siloxane monomers.

FIG. 7 depicts the proposed morphology of the SB5 hydrogel formulation cured to form the electrical contact at the tip of a nasal stimulator device.

FIG. 8A depicts a dipping method for hydrogel shaping. FIG. 8B illustrates a scooping method for hydrogel shaping. FIG. 8C shows a hydrogel tip in which part of the tip has been masked during spraying of an insulator to provide a conductive portion.

FIGS. 12A-12D depict an exemplary mold and casting method for shaping the hydrogel.

FIGS. 16A-16D depict exemplary tip assembly structures and methods of use that include a hinge.

FIGS. 17A-17E depict an exemplary dispensing cassette and method for manufacturing the tip assemblies.

FIGS. 18A-18D illustrate an exemplary method of attaching tip assemblies to a base unit using the dispensing cassette of FIGS. 17A-17E.

DETAILED DESCRIPTION

Figure 1:
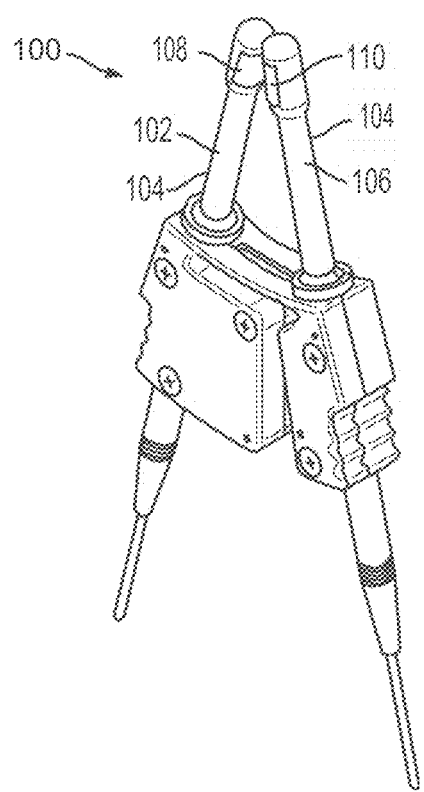
FIG. 1 depicts an exemplary nasal stimulator device having an adjustable pair of stimulator electrodes.

The polymer formulations described herein are generally hydrogels that may be used to facilitate an electrical connection between an electrode of a nasal stimulator device and nasal or sinus tissue, as mentioned above. Accordingly, the hydrogels are biocompatible and formed to be non-irritating and non-abrasive to nasal and sinus tissue. The hydrogels are generally also formed so that they do not break or shatter during insertion or use, and have moderate adhesion to nasal or sinus tissue in order to minimize contact resistance, heating, and heat damage to the tissue it contacts. The hydrogels may be prepared by cross-linking of various monomers using UV or visible light. The nasal stimulator device may include a disposable component and a reusable component. The disposable component may generally include a pair of stimulator electrodes and the electrically conductive hydrogel, and the reusable component a source of electrical energy for the stimulator electrodes. However, in some instances the nasal stimulator device can be made to be completely disposable.

Electrically Conductive Hydrogel Formulations

The electrically conductive hydrogels ("conductive hydrogels") may comprise any monomer that is capable of providing a formulation suitable for use with nasal or sinus tissue, and suitable to facilitate an electrical connection between a nasal stimulator device, e.g., a hand-held nasal stimulator device, and nasal or sinus tissue. The formulation is typically prepared by UV cross-linking of the monomers, as further described below. In some variations, the formulations provide electrically conductive acrylate/methacrylate/vinyl hydrogels. In other variations, the formulations provide electrically conductive silicone-acrylate hydrogels.

In one variation, the conductive hydrogel formulation may include a first monomer; a second monomer; and a photoinitiator, where the first monomer is an acrylate monomer. Here the acrylate monomer may be a monofunctional monomer, a difunctional monomer, a trifunctional monomer, or a precursor or a derivative thereof.

Examples of monofunctional monomers that may be included in the formulations include without limitation, acrylic acid, butyl acrylate, butyl methacrylate, 2-chloro-ethyl vinyl ether, ethyl acrylate, 2-ethylhexyl acrylate, furfuryl acrylate, glycerol monomethacrylate, hydroxyethyl methacrylate, methacrylic acid, methoxy polyethylene glycol dimethacrylate, methoxy polyethylene glycol monoacrylate, and aminoethyl methacrylate.

The difunctional monomers that may be used in the formulations include, but are not limited to, diethylene glycol diacrylate, ethylene glycol dimethacrylate, neopenyl glycol diacrylate, polyethylene glycol diacrylate, polyethylene glycol di-methacrylate, triethylene glycol diacrylate, and N,N' dimethylene bisacrylamide.

With respect to the trifunctional monomer, examples include without limitation, pentaerythritol triacrylate, propxylated glycol triacrylate, trimethylpropane triacrylate, and trimethylol propane trimethacrylate.

The first monomer and the second monomer may or may not be the same type of monomer. Examples of second monomers include, but are not limited to, dimethylacrylamide, glycidyl methacrylate, N-vinylpyrrolidone, and 1,4-butanediol diacrylate.

Silane or siloxane monomers may also be used to form an electrically conductive hydrogel. Suitable siloxane monomers typically comprise a

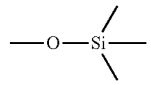

group. In one variation, silane methacrylate monomers are included in the conductive hydrogel formulations as the first and/or second monomer. For example, methacryloxypropyltris (trimethylsiloxy) silane, methacryloxymethyltris (trimethylsiloxy) silane, methacrylodxypropylbis (trimethylsioloxy) silanol, 3-methoxypropylbis(trimethylsiloxy) methyl silane, methacryloxypentamethyldisiloxane, methacryloxypropyltrimethoxy silane, and methacryloxypropyltris (methoxyethoxy) silane monomers may be used. In further variations, acrylic terminated silane and siloxane monomers, e.g., as shown in FIG. 6 may be used. These acrylic terminated silane and siloxane monomers include, but are not limited to, trimethyl silyl methacrylate, 2 (trimethylsilyloxy) ethyl methacrylate, 3-(trimethyoxysilyl)propyl methacrylate, and (3-methacryloyloxypropyl) tris (trimethylsiloxy)silane. In some instances, it may be beneficial to include 3-methacryloxyproplyl tris (trimethyl siloxy) silane in the hydrogels. Vinyl substituted silane monomers may also be used in the hydrogel formulations. Here the silane monomer may be one that comprises a —SiR group, where R may be hydrogen, or a methyl or an alkyl group.

Hydrogels containing siloxane monomers may retain the water they absorb over a longer exposure to air, and thus, retain their electrical conductivity for a longer period of time. The mole fraction of siloxane groups in the silicone hydrogels may range from about 5% to about 20%. When a silane group is employed, the mole fraction of silane groups in the hydrogels may range from about 5% to about 20%.

The conductive hydrogels may be formed by a UV cross-linking process. In this instance, a photoinitiator is generally included in the formulation. Photoinitiators may be any chemical compound that decomposes into free radicals when exposed to light, e.g., UV radiation having a wavelength in the range of about 350 nm to about 450 nm. The free radicals initiate polymerization to form cross-linked hydrogels. In one variation, the photoinitiator initiates ring opening polymerization. In another variation, the photoinitiator initiates cationic polymerization. In a further variation, the photoinitiator initiates polymerization by a thiol-ene reaction.

Any suitable photoinitiator may be employed in the formulations described herein. For example, the photoinitiator may be selected from the group consisting of acylphosphine oxides (APOs), bisacylphosphine oxides (BAPOs), 2,2-dimethoxy-1,2-diphenylethan-1-one (Igracure® photoinitiator), benzoin ethers, benzyl ketals, alpha-dialkoxyacetophenones, alpha-hydroxyalkylphenones, alpha-amino alkylphenones, benzophenones, thioxanthones, and combinations and derivatives thereof. In some instances, it may be useful to include an acylphosphine oxide or bisacylphospine oxide photoinitiator in the formulation.

The acylphosphine oxide photoinitiators that may be used include without limitation, 2,4,6-trimethylbenzoyl-diphenylphospine oxide (TMDPO); benzoyl-diphenylphosphine oxide (BDPO); 2,4,6-trimethylbenzoyl-methoxy-phenyl-phosphine oxide (TMMPO); phthaloyl-bis(diphenylphosphine oxide (PBDPO)); tetrafluoroterephthanoyl-bis(diphenylphosphine oxide) (TFBDPO); 2,6-difluoro benzoyl-diphenylphospine oxide (DFDPO); (1-naphthoyl) diphenylphosphine oxide (NDPO); and combinations thereof. In one variation, 2,4,6-trimethylbenzoyl-diphenyl-phospine oxide (TMDPO) is a useful photoinitiator.

The bisacylphosphine oxide photoinitiators that may be used include without limitation, bis(2,4,6-trimethylbenzoyl)-phenylphosphine oxide (BTMPO); bis(2,6-dimethoxybenzoyl)-2,4,4-trimethyl-pentylphosphine oxide; 1-hydroxy-cyclohexyl-phenyl-ketone; and combinations thereof.

The conductive hydrogels described herein may further include a suitable diluent. Suitable diluents may be glycerin, isopropanol, polyethylene glycol, water, methanol, and combinations thereof. Table 1 shows an exemplary list of monomers, photoinitiators (e.g., UV initiators), and diluents that may be used to make the conductive hydrogels.

TABLE 1

Exemplary list of formulation monomers, diluents, and UV initiators.

| Monofunctional Monomers | Difunctional Monomers | Trifunctional Monomers | Silane and Siloxane Monomers | UV Initiators | Diluents |
|---|---|---|---|---|---|
| Acrylic acid | Ethylene glycol dimethacrylate | Pentaerythritol triacrylate | Trimethyl silyl methacrylate | Irgacure 189 (Ciba/BASF) | Water |
| Methacrylic acid | Polyethylene glycol diacrylate (200-1500) | Trimethyl-propane triacrylate | 2(trimethylsilyloxy) Ethyl methacrylate | Irgacure 819 (Ciba/BASF) | Isopropanol |

TABLE 1-continued

Exemplary list of formulation monomers, diluents, and UV initiators.

| Monofunctional Monomers | Difunctional Monomers | Trifunctional Monomers | Silane and Siloxane Monomers | UV Initiators | Diluents |
|---|---|---|---|---|---|
| Methoxy polyethylene glycol monoacrylate (300-550) | Neopentyl glycol diacrylate | Propoxylated glycol triacrylate | 3(trimethoxysilyl) propyl methacrylate | Irgacure 1173 (Ciba/BASF) | Polyethylene glycol |
| Methoxy polyethylene glycol dimethacylate | Diethylene glycol diacrylate | Trimethylol Propane trimethacrylate | 3(methacryloyloxy propyl) tris (trimethylsiloxy silane) | Lucirin TPO (BASF) | Glycerin |
| Hydroxyethyl methacrylate | Triethylene glycol diacrylate | | | | Methanol |
| Furfuryl Acrylate | N,N' dimethylene bisacrylamide | | | | |
| Glyceryl monomethacrylate | Polyethylene glycol di-methacrylate | | | | |

In some variations, the monofunctional monomers are selected from Table 1 and comprise no more than 80% and no less than 30% moles/mole of the formulation prior to addition of diluents. In other variations, the difunctional monomers are selected from Table 1 and comprise no more than 25% and no less than 5% moles/mole of the formulation prior to the addition of diluents. In further variations, the trifunctional monomers are selected from Table 1 and comprise about 0.0 to about 5.0 moles/100 moles of the formulation prior to the addition of diluents.

The conductive hydrogels will generally be formed to have one or more characteristics that adapt it for use with a nasal stimulator device. For example, characteristics such as electrical resistivity, maximum hydration level, tensile strength (elongation break), Young's modulus, glass transition temperature, and cross-link density, may be adjusted to adapt the conductive hydrogel for use with a nasal stimulator device.

The electrical resistivity of the conductive hydrogel may range from about 50 to about 2,000 Ohm•cm, or from about 150 to about 800 Ohm•cm. In one variation, the electrical resistivity ranges from about 400 to about 800 Ohm•cm. In another variation, the electrical resistivity ranges from about 200 to about 600 Ohm•cm. In a further variation, the electrical resistivity ranges from about 150 to about 500 Ohm•cm. Alternatively, the electrical resistivity may range from about 550 to about 600 Ohm•cm.

With respect to other characteristics of the conductive hydrogel, the maximum hydration level may range from about 35% to about 80% by weight, and the tensile strength (elongation at break) may range from about 35% and 150%, or from about 35% to about 100%, at 30% relative humidity. Here hydration level is defined as $(W_{hydrated\ polymer} - W_{dry\ polymer}) = W_{hydrated\ polymer}$. Young's modulus ranges of the conductive hydrogel may range from about 0.1 to about 1.5 MPa, or from about 0.1 to about 1.0 MPa. The glass transition temperature of the conductive hydrogel may range from about 5 to about 65 degrees Celsius in the dry state. Furthermore, the cross-link density may range from about 0.01 to about 0.10 moles/mole.

The conductive hydrogel formulations may contain fillers to improve one or more of the following: mechanical properties, cosmetic appearance, electrical properties, and cost. Suitable fillers may include without limitation, silica, alumina, titanium dioxide, polyethylene microspheres, carbon black, nanofibers, nanoparticles, and combinations thereof.

The conductive hydrogel formulations may be a homogenous material or they may comprise a multiphase blend or a block copolymer with relatively hydrophobic and relatively hydrophilic domains that have undergone a microphase separation.

Additionally, the conductive hydrogel formulations may contain additives that are either soluble or present in a dispersed form in the polymer material. These additives may include hydrophilic molecules, cage molecular structures, surface modifying agents, or amphiphilic molecules. Exemplary amphiphilic molecules include without limitation, cellulose, dextran, hydroxypropyl cellulose, hydroxymethyl cellulose, hyaluronic acid, sodium hyaluronate, chitin, chitosan, crown ether derivatives, and combinations thereof.

Conductive hydrogel formulations having the following characteristics may be useful in facilitating electrical communication between a nasal stimulator device and nasal or sinus tissue:

Electrical resistivity ranging from 200-800 Ohm•cm, elongation at break greater than 50% in tensile mode, and hydration level in the range of 25-80% (hydration level being expressed as the equilibrium swelling ratio, $W_h/W_G \times 100$, where $W_h$ is the mass of water at equilibrium at a particular temperature, and $W_G$ is the weight of the hydrated gel measured under the same conditions);

Electrical resistivity at the fully hydrated state ranging from 300 to 500 Ohm•cm;

Equilibrium swelling ratio ranging from 35-65%;

Hydration level that does not change by more than approximately 10% (or 5.0 to 30 g if comparing hydrogel weight before and after hydration), over 15 hours of continuous exposure to indoor air at 25 degrees Celsius, with a relative humidity not less than 30%;

Young's modulus ranging from 0.10 to 10 MPa in the fully hydrated state, and a glass transition temperature of the dry gel ranging from 5 to 65 degrees Celsius; or Cross-link density ranging from 0.01 to 0.10 moles/mole.

Some variations of the conductive materials may comprise polyethylene or polypropylene polymers filled with carbon black or metal particles. Other variations may include conducting polymers such as poly-phenylene sulfide, poly-aniline, or poly-pyrrole. Ionically conducting variations such as hydrophilic, cross-linked polymer networks are also contemplated. However, in some instances the conductive hydrogel may be neutral and comprise hydrophobic segments or domains in a hydrophilic network. In yet further variations, the conductive hydrogel may comprise ionic pendant groups, some of which provide ionic or electrostatic cross-linking. A conductive hydrogel that is a biocompatible, hydrophilic, cross-linked network comprising hydrophobic segments, and which has a glass transition temperature in the range 5 to 65 degrees Celsius, and an elongation at break in the range of 50% to 150% may be useful.

In yet further variations, it may be beneficial for the conductive hydrogels to have a high water content, e.g., a water content of 60% or greater, as calculated by the following formula: percent water=$(W_{hydrated\ gel} - W_{dry\ gel})/(W_{hydrated\ gel}) \times 100$, where W is weight. In some variations, the water content may range from about 60% to about 99%, from about 60% to about 95%, from about 60% to about 90%, from about 60% to about 85%, from about 60% to about 80%, from about 60% to about 75%, from about 60% to about 70%, or from about 60% to about 70%. In general, the lower limit is the amount of water needed to be absorbed so that the hydrogel maintains a high water content after several hours of exposure to air at room temperature and moderate levels of relative humidity. The value for the upper limit of water content may be influenced by the need to have mechanical robustness, including a tensile modulus higher than about 0.1 MPa and an elongation break greater than 50%.

Exemplary conductive hydrogels having high water content may comprise cross-linked networks that include monomers such as acrylamide, methacrylamide, dimethylacrylamide, or combinations thereof. In one variation, the high water content hydrogel includes poly-dimethylacrylamide cross-linked by potassium persulfate.

In another variation, the high water content hydrogel may comprise an ionic co-monomer including, but not limited to, sodium acrylate, zinc arylate, calcium acrylate, or combinations thereof. The ionic co-monomer may be used at a concentration ranging from zero to about 20 mole percent. Hydrogels using an ionic co-monomer may have a percent water content of 99% or more.

Hydrogels having a high water content generally have an elastic modulus ranging from about 0.001 to 0.01 MPa. When employed with the nasal stimulator devices referred to herein, the hydrogels may require a higher level of cross-linking so that the minimum elastic modulus is about 0.1 MPa. The additional cross-linking may be provided by adding N,N'diethyl bis-acrylamide co-monomer to the hydrogel formulation. The N,N'diethyl bis-acrylamide co-monomer may be added in an amount ranging from about 0.5% to about 2.0%, or from about 0.5% to about 1.0% by weight of the formulation. Exemplary conductive hydrogel formulations with high water conduct are provided below in Table 2.

TABLE 2

Exemplary Conductive Hydrogel Formulations with High Water Content

| MONOMER | CONCENTRATION | Function |
| --- | --- | --- |
| N,N' Dimethyl acrylamide | 50-90% | Monomer and cross-linker |
| N,N' Dimethyl bisacrylamide | 0.5-2.0% | Cross-linker |
| Sodium Acrylate | 0-10% | Monomer |
| Zinc acrylate | 0-10% | Monomer |
| Polyethylene glycol diacrylate | 0-10% | Cross-linker |
| Cumyl hydroperoxide | 0-1% | Initiator |
| Potassium persulfate | 0-1% | Initiator |

In some variations, it may be useful to include hydrophilic groups into the conductive hydrogels so that the hydrogels form a relatively strong complex with water molecules, thereby increasing the activation energy of the dehydration process in the molecular structure of the hydrogel network and reducing the drying out (or dry out) rate of the hydrogels. For example, polysaccharides may be included in the hydrogels as a hydrophilic additive since they are biocompatible, strongly bind water, and can be chemically immobilized on the hydrogel network. The polysaccharides that may be used include, but are not limited to, dextran sulfate, hyaluronic acid, sodium hyaluronate, hydroxymethyl cellulose, chitosan, sodium alginate, and combinations thereof. When a polysaccharide additive is employed, it may be included in the hydrogels in an amount ranging from about 0.5% to about 20%, from about 0.5% to about 15%, from about 0.5% to about 10%, or from about 0.5% to about 5%, by weight of the formulation. The polysaccharide additive may be added to the monomer formulation or it may be incorporated into the network during hydration.

The drying out rate of the hydrogel can also be substantially reduced by including a hydrating agent or a hydrating medium in the hydrogel formulation. For example, propylene glycol and polymers thereof can be included as a hydrating agent. Additionally, mixtures of propylene glycol and water can be used as a hydrating medium. The inclusion of a propylene glycol and water mixture in the hydrogel formulation may result in less water being present at the hydrogel surface, and thus evaporated from, the hydrogel surface.

Propylene glycol and water can be combined in various amounts or ratios in the hydrating medium. In some variations, the hydrating mixtures can comprise propylene glycol in an amount between about 5 to about 85 percent by volume, between about 5 to about 80 percent by volume, between about 5 to about 75 percent by volume, between about 5 to about 70 percent by volume, between about 5 to about 65 percent by volume, between about 5 to about 60 percent by volume, between about 5 to about 55 percent by volume, between about 5 to about 50 percent by volume, between about 5 to about 45 percent by volume, between about 5 to about 40 percent by volume, between about 5 to about 35 percent by volume, between about 5 to about 30 percent by volume, between about 5 to about 25 percent by volume, between about 5 to about 20 percent by volume, between about 5 to about 15 percent by volume, or between about 5 to about 10 percent by volume. In other variations, the hydrating mixtures can comprise propylene glycol in an amount between about 20 to about 50 percent by volume or between about 20 to about 35 percent by volume. In further variations, the hydrating mixtures can comprise propylene glycol in an amount of about 5 percent by volume, about 10 percent by volume, about 15 percent by volume, about 20 percent by volume, about 25 percent by volume, about 30 percent by volume, about 35 percent by volume, about 40 percent by volume, about 45 percent by volume, about 50 percent by volume, about 55 percent by volume, about 60 percent by volume, about 65 percent by volume, about 70 percent by volume, about 75 percent by volume, about 80 percent by volume, or about 85 percent by volume.

Water may make up the remainder of the hydrating mixtures, or in some instances, other components may be included. The hydrating mixtures can comprise water in an amount between about 15 to about 95 percent by volume. For example, the hydrating mixtures can comprise water in an amount of about 15 percent by volume, about 20 percent by volume, about 25 percent by volume, about 30 percent by volume, about 35 percent by volume, about 40 percent by volume, about 45 percent by volume, about 50 percent by volume, about 55 percent by volume, about 60 percent by volume, about 65 percent by volume, about 70 percent by volume, about 75 percent by volume, about 80 percent by volume, about 85 percent by volume, about 90 percent by volume, or about 95 percent by volume. Instead of water, saline may also be used, and included in the same amounts described as for water.

Exemplary hydrating mixtures may include propylene glycol and water (or saline) in the following amounts: about 5 percent by volume propylene glycol and about 95 percent by volume water; about 10 percent by volume propylene glycol and about 90 percent by volume water; about 15 percent by volume propylene glycol and about 85 percent by volume water; about 20 percent by volume propylene glycol and about 80 percent by volume water; about 25 percent by volume propylene glycol and about 75 percent by volume water; about 30 percent by volume propylene glycol and about 70 percent by volume water; about 35 percent by volume propylene glycol and about 65 percent by volume water; about 40 percent by volume propylene glycol and about 60 percent by volume water; about 45 percent by volume propylene glycol and about 55 percent by volume water; about 50 percent by volume propylene glycol and about 50 percent by volume water; about 55 percent by volume propylene glycol and about 45 percent by volume water; about 60 percent by volume propylene glycol and about 40 percent by volume water; about 65 percent by volume propylene glycol and about 35 percent by volume water; about 70 percent by volume propylene glycol and about 30 percent by volume water; about 75 percent by volume propylene glycol and about 25 percent by volume water; about 80 percent by volume propylene glycol and about 20 percent by volume water; or about 85 percent by volume propylene glycol and about 15 percent by volume water. The exemplary hydrating mediums provided below in Table 3 may be useful in hydrogels that are employed as electrical contacts in nasal stimulator devices.

TABLE 3

Exemplary Hydrating Mediums

| Component/Amount | Hydrating Medium 1 | Hydrating Medium 2 | Hydrating Medium 3 | Hydrating Medium 4 |
|---|---|---|---|---|
| Propylene Glycol (vol %) | 35 | 40 | 45 | 50 |
| Water (vol %) | 65 | 60 | 55 | 50 |

The hydrogels described herein generally have a functional time period and a dry out time period. The functional time period is typically the period of time during which the hydrogels can be used without substantial loss of function (e.g., the impedance of the hydrogel does not rise higher than about 2500 Ohms). The dry out time period is typically the maximum time period of use of the hydrogel, where at the end of the period, function, e.g., stimulative function, of the hydrogel has substantially decreased. It would be beneficial to maximize both the functional time period and dry out time period for the hydrogel tips of the nasal stimulator devices described herein to extend, e.g., their shelf life. Table 4 provides the functional time periods, dry out time periods, and impedances for four exemplary hydrogel tips. All four hydrogels included the SB5 formulation described in Example 15, but further included a propylene glycol hydrating medium having propylene glycol amounts varying from about 35 percent by volume to about 50 percent by volume.

TABLE 4

Exemplary Functional Time Periods, Dry Out Time Periods, and Impedances

| | Hydrogels with Propylene Glycol (PG) Hydrating Medium | | | |
|---|---|---|---|---|
| | 35 vol % PG | 40 vol % PG | 45 vol % PG | 50 vol % PG |
| Functional Time Period (hours) | 14 | 17.1 | 22 | 24.4 |
| Dry Out Time Period (hours) | 17.8 | 22.1 | 27.1 | 31.0 |
| Impedance (ohms) | 1150 | 1300 | 1670 | 1600 |

By varying the amount or ratio of propylene glycol in the hydrating medium, Table 4 shows that lifetime of the hydrogel tip can be tailored to the desired indication. For example, if a nasal stimulator device is intended for single day use, it may be useful to include a 35 percent by volume (vol %) propylene glycol hydrating medium to form the hydrogel tip. The hydrogels, whether they include a hydrating agent or hydrating medium, or whether they do not include a hydrating agent or hydrating medium, can be suitably sized, shaped, molded, etc. to form an electrical contact of a nasal stimulator device. For example, the hydrogels can be included as part of a prong of a nasal stimulator device, generally at the tip of the prong. Although the use of the hydrating mediums in hydrogel tips for nasal or sinus stimulation has been described, it should be understood that they can be used in hydrogels for other applications.

As stated above, the conductive hydrogels can be included in the prongs or tips of nasal stimulator devices and used to facilitate an electrical connection between a nasal stimulator device and nasal or sinus tissue. Some examples of such nasal stimulator device prongs or tips are provided in U.S. application Ser. No. 14/256,915 (U.S. Publication No. 2014/0316485), entitled, "NASAL STIMULATION DEVICES AND METHODS," filed Apr. 18, 2014, the contents of which are hereby incorporated by reference in their entirety (the conductive hydrogels in U.S. application Ser. No. 14/256,915 are referred to as hydrogel electrodes). The nasal stimulator device may be configured to include a disposable component that is removably attached to a reusable component or housing. An exemplary disposable component is shown in FIG. 1. In that figure, the disposable unit (100) consists of a pair of arms or prongs (102, 106) that house electrodes (not shown), which are adjustable in a lateral direction, and which can also be rotated or swung so as to vary the angle between them. Each electrode is provided in the form of a metal rod that is encased in a polymeric sleeve (104). Each sleeve (104) ends in a slot (108, 110), to be filled with an electrically conducting polymer (e.g., hydrogel) that forms an electrical contact between the electrode and nasal or sinus tissue.

Figure 2:
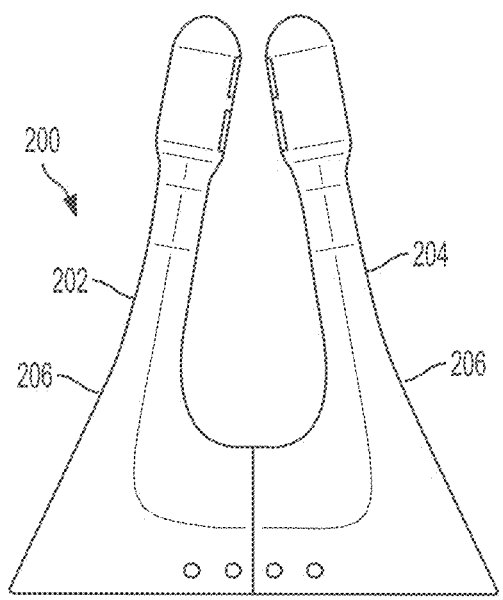
FIG. 2 depicts a top view of the disposable component of another exemplary nasal stimulator device including a pair of spring-like electrodes substantially enclosed by an opaque sleeve.

Alternatively, and as illustrated in FIG. 2, the disposable unit (200) has a pair of arms or prongs (202, 204) that comprise an opaque polymeric sleeve (206) encasing electrodes (not shown). The opaque polymeric sleeve may be configured to completely cover the electrodes or to partially cover the electrodes. In this variation, the sleeve (206) and the electrodes are made flexible and spring like. Their flexibility is designed to accommodate variations in the width of the nose, and the angular orientation preferred by an individual user. Similar to FIG. 1, an electrically conductive hydrogel can be disposed at the tip of the prongs (202, 204) to function as an electrical contact between the electrode and the nasal or sinus tissue.

Figure 3:
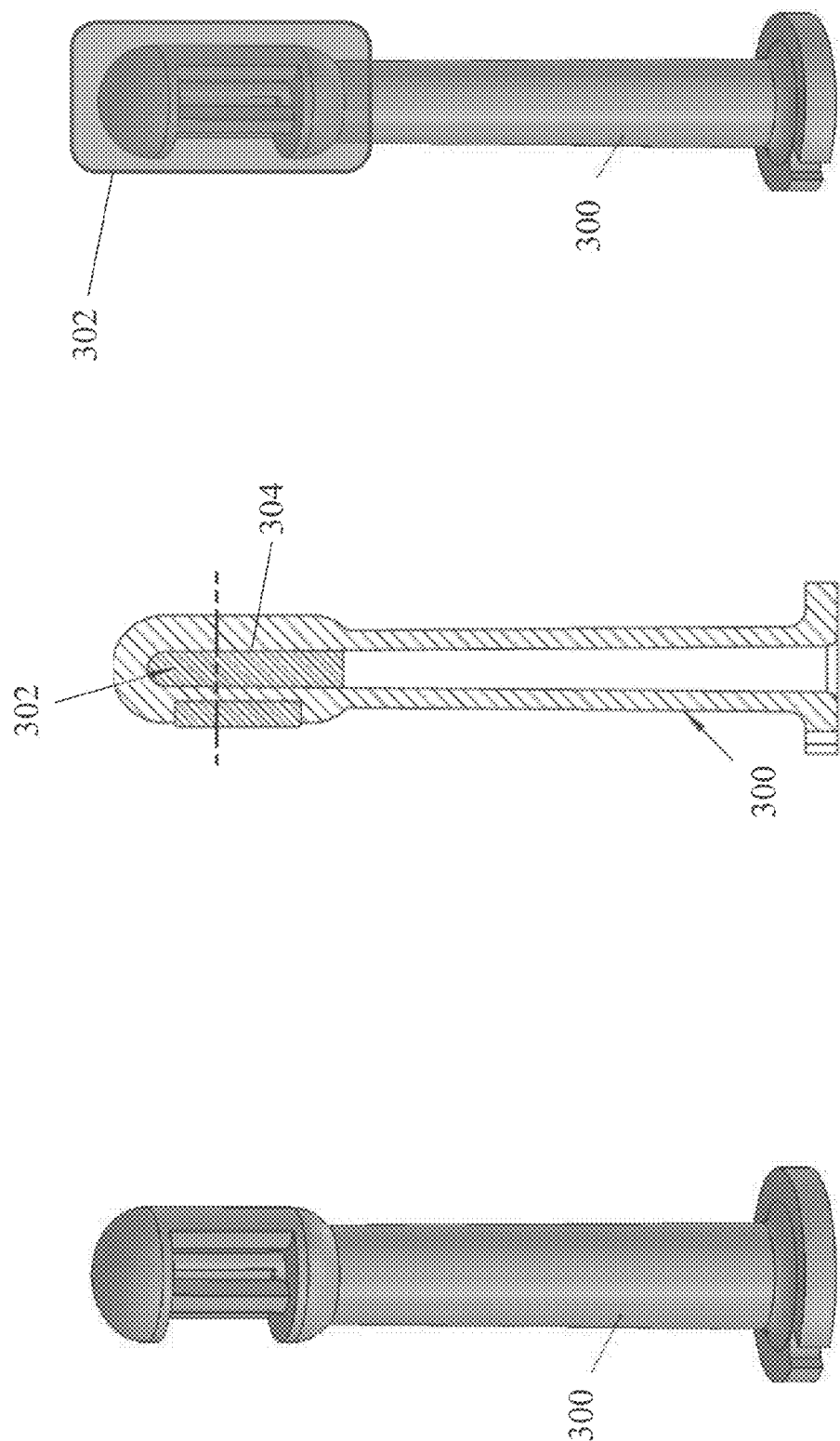
FIGS. 3A-3C depict exemplary configurations of the electrically conductive polymer provided in the disposable component of a nasal stimulator device.

FIGS. 3A-3C provide exemplary configurations of the conductive hydrogel when employed with a nasal stimulation device. FIG. 3 shows the polymeric sleeve (300) as an opaque tube, which surrounds the supporting electrode inside. In this variation, the sleeve (300) ends in a slot that is filled with a conductive polymer that provides an electrical connection between the electrode and nasal or sinus tissue. As depicted in the cross-sectional view of FIG. 3B, the polymer (302) fills the slot (304) and forms a slightly protruding cylindrical surface for optimum contact with nasal tissue. It may be beneficial for this polymer to be squeezable, so that it can conform to the contours of the nasal cavity, which is lined with a mucous membrane of squamous epithelium, which tissue then transitions to become columnar respiratory epithelium. The cavity provides drainage for the sinuses and the nasolacrimal duct, and therefore presents a highly humid and moist environment. (Anatomy of the human nose, Wikipedia). In the variation shown in FIG. 3B, the conductive polymer forms a shell (306) around the end of the sleeve (300), filling the slot and extending down the sleeve to contact the electrode.

Process for Making the Electrically Conductive Hydrogels

The process for producing the electrically conductive hydrogels described herein generally comprise the steps of: mixing a first monomer, a second monomer, and a photoinitiator to prepare a formulation, wherein the first monomer is an acrylate monomer; and irradiating the formulation with UV radiation to cross-link the formulation. The monomers may be ones provided above, e.g., as listed in Table 1. In some variations, the conductive hydrogel is cross-linked by covalent bonds. In other variations, the hydrogel is cross-linked by ionic bonds. In hydrogels with hydrophilic and hydrophobic domains, the hydrophobic domains may form a shell around a hydrophilic core, forming a core-shell structure. A hydrogel with a high water content (e.g., 50-70%) with a hydrophobic shell may dry out more slowly than a hydrogel without a hydrophobic shell, and therefore may retain its electrical conductivity for a longer period when left exposed to air in between uses.

In some variations, the hydrogel may be surface modified to develop a relatively more hydrophilic surface in order to further reduce skin resistance upon contact with nasal tissue. Surface modification may be desired for hydrogels that have developed a hydrophobic shell, leading its surface to become hydrophobic. In this application, a surface is generally deemed to be hydrophobic if its water contact angle (sessile drop) exceeds 80 degrees, while it is generally deemed to be hydrophilic if the contact angle is less than 30 degrees. Surface modification may be achieved in several ways. One method is to treat the formed hydrogel with a low pressure plasma, produced by an RF discharge or a microwave discharge. Suitable plasma materials include air, oxygen, and water vapor. This method is believed to cause chemical modification of the molecules on the surface, forming hydroxyl groups that render the surface hydrophobic. Another method is to deposit a hydrophilic polymer via plasma polymerization, including plasma assisted chemical vapor deposition (PACVD), or plasma initiated chemical vapor deposition (PICVD). Suitable materials to be deposited using the plasma polymerization method include HEMA or GMA. Yet another surface modification method, applicable to hydrogels with siloxane groups on the surface (e.g., hydrogel SB5 described in Examples 15-19 below), includes chemical activation of the surface, for example, by treating the surface with aqueous sodium hydroxide (1-10% w/w), washing it to remove unreacted alkali, then reacting it with a hydroxyl or amino terminated molecule such as polyethylene glycol. In yet another method, surface modification may consist of the addition of a surfactant into the hydrogel formulation that migrates to the surface upon polymerization. A surfactant is an amphiphilic molecule that exposes a hydrophilic end at the surface of the hydrogel. Exemplary surfactants include sodium dodecyl sulfate, salts of polyuronic acid, Triton X-80, etc. Alternatively, the hydrogel surface may be modified, e.g., to become more hydrophilic, by including a hydrating medium into the formulation. Exemplary hydrating mediums are described above.

The conductive hydrogel formulations may be prepared to cure to a zero or a low expansion solid that is formulated with diluents in the same weight fraction as the equilibrium swelling ratio of the hydrogel when fully cured. The weight ratio of diluents to the monomer and photoinitiator mix may be from about 35% to about 70%. Exemplary diluents that may be employed are listed in Table 1. These diluents are water soluble, biocompatible, and have a viscosity less than 100 CST at 25 degrees Celsius.

The curing process may be caused by any suitable wavelength of light. In some variations, the curing process is caused by irradiation with UV light in the wavelength range of about 350 nm to about 450 nm, and is catalyzed by one or more photoinitiators selected from Table 1. Other photoinitiators, also as described above may be used. For example, acylphosphine oxides and bisacylphosphine oxides that are biocompatible, and which absorb long wavelength ultraviolet radiation may be used.

Table 5 provides an exemplary list of conductive hydrogel formulations that were cured by irradiation with UV light at a wavelength range of 300 nm to 480 nm, e.g., 350 nm to 450 nm, at a temperature ranging from 10 to 65 degrees Celsius, preferably 25 to 45 degrees Celsius, and over a time period of 10 seconds to 30 minutes, e.g., 1 minute to 15 minutes, and using 2,4,6-trimethylbenzoyl-diphenylphosphine oxide (TMDPO) as the photoinitiator.

TABLE 5

Exemplary conductive hydrogel formulations.

| | Formulation* | Water Content (%)** |
|---|---|---|
| 1 | HEMA/DMA 700CL | 34 |
| 2 | GMA/DMA 700CL | NM |
| 3 | 100% MAA/DMA 700CL | 44 |
| 4 | HEMA/GMA/DMA 700 CL | 42 |
| 5 | HEMA/HEMA10/DMA 700 CL | 44 |
| 6 | HEMA/DMAC/DMA(700) Crosslinker | 50 |
| 7 | HEMA/GMA/BDDA CL | 41 |
| 8 | HEMA10/HEMA/BDDA CL | 39 |
| 9 | HEMA/DMAC/DMA(700) Crosslinker | 57 |
| 10 | NVP/DMAC/HEMA | 50 |
| 11 | NVP/DMAC/HEMA | 69 |
| 12 | NVP/DMAC/HEMA | 78 |
| 13 | NVP/DMAC/HEMA | 77 |
| 14 | NVP/DMAC/HEMA with glycerol diluent | 77 |
| 15 | NVP/DMAC/HEMA | 70 |
| 16 | NVP/DMAC/HEMA with glycerol diluent | 78 |
| 17 | HEMA/MEMA/PEG diluent | 34 |
| 18 | HEMA/MAA/DMA 700/water/PEG400 | NM |
| 19 | HEMA/MAA/DMA 700/water/PEG400 | 20 |

*HEMA = hydroxyethyl methacrylate; DMA = dimethylacrylamide; GMA = glycerol monomethacrylate; MAA = methacrylic acid; DMAC = dimethylacetamide; BDDA = 1,4-butanediol diacrylate; NVP = N-vinylpyrrolidone; MEMA = methoxyethyl methacrylate; HEMA10 = poly ethoxy (10) ethyl methacrylate.
**NM = not measured.

Other exemplary conductive hydrogel formulations are provided in Examples 1-7, and 15. Based on the data from experiments run with these hydrogel formulations, a hydrogel that exhibits high hydration with a minimal increase in mass and height (i.e., swelling/expansion) may be useful. Expansion due to swelling of the hydrogel generally produces effects that may require balancing. For example, swelling enhances electrical conductivity, makes the hydrogel more hydrophilic, and thus more comfortable when in contact with skin, and reduces contact resistance. However, more swelling also makes the hydrogel more sticky and less robust, and therefore more prone to breakage during application of current, and increases the drying out rate (although the amount of water left over after a specific period of dry-out depends both on the rate of dry out and the initial water content). Taking these effects into consideration, exemplary formulations (e.g., formulations SB4A and SB4B) may incorporate a diluent that is an inert solvent that forms a hydrogel having a substantial swelling ratio (or water uptake) but which does not expand upon hydration since the incoming water replaces the diluent leaving with less volume change upon hydration and swelling in water. For example, the hydrogel formulations provided in Example 6 (hydrogel formulation SB4A) and Example 7 (hydrogel formulation SB4B) that include acrylic terminated siloxane monomers may be useful. The SB4A and SB4B hydrogel formulations demonstrated a high level of hydration with minimal expansion, as shown in the data provided in Example 14. The silicone hydrogel formulation provided in Example 15 (hydrogel formulation SB5), which exhibited increased cross-linking due to the inclusion of trimethoylol propane trimethacrylate, demonstrated zero expansion, as shown in the data provided in Example 18. Overall, the data provided in Examples 16-19 provide that the SB5 formulation (SB5) may be useful when formed as a hydrogel tip of a nasal stimulator device. The expansion of the SB5 formulation upon hydration was shown to be significantly less than earlier formulations (e.g., SB1 and SB2), and extended less than 0.5 mm beyond the boundary of the tip when the hydrogel was fully hydrated. Additionally, resistance was less than 600 Ω, well within requirements, and it did not increase beyond 1000 Ω upon drying for up to 8 hours. The results also showed that the SB5 formulation was sufficiently extracted and hydrated so as to be ready for use after 12-24 hours of extraction in saline at 55 degrees celsius. However, the hydrophobic nature of its surface caused an increase in contact resistance, especially in contact with parts of the nasal tissue that is especially hydrated. This problem can likely be solved by a hydrophilic surface modification or addition of a hydrating medium, as previously described herein. A hydrogel that is capable of high levels of water uptake (i.e., high hydration) will typically be more electrically conductive. Parameters such as monomer extraction rate and electrical resistance can be measured and the resultant values used to indicate the hydration level of the hydrogels, as provided in Examples 8-12, 16, and 17. The addition of a diluent, as shown in Example 9 does not appear to effect hydration of the hydrogel, but may affect cure rate.

Manufacturing Methods

Various manufacturing methods are also described herein. These processes may include various ways of curing the hydrogel formulations, various ways of obtaining a suitable hydrogel shape, and various ways of assembling the hydrogel at the tip of a nasal stimulator. The manufacturing methods may be useful in forming the hydrogel contact of the disposable pronged portion of the nasal stimulator provided in FIG. 2, or hydrogel contacts of nasal stimulator prongs/tips having alternative configurations, such as the nasal stimulator prongs/tips described in U.S. application Ser. No. 14/256,915 (U.S. Publication No. 2014/0316485), entitled, "NASAL STIMULATION DEVICES AND METHODS," filed Apr. 18, 2014, the contents of which were previously incorporated by reference in their entirety (the conductive hydrogels in U.S. application Ser. No. 14/256,915 are referred to as hydrogel electrodes). In general, manufacturing methods that help with scalability and storage of the shaped hydrogel may be useful. Furthermore, manufacturing methods that increase the volume of hydrogel at the tip of the electrode of a nasal stimulator may be beneficial since this would lead to less drying out of the hydrogel. Manufacturing methods tailored so that the hydrogel forms a bulge at the distal end of the electrode of a nasal stimulator may also be useful.

Figure 4:
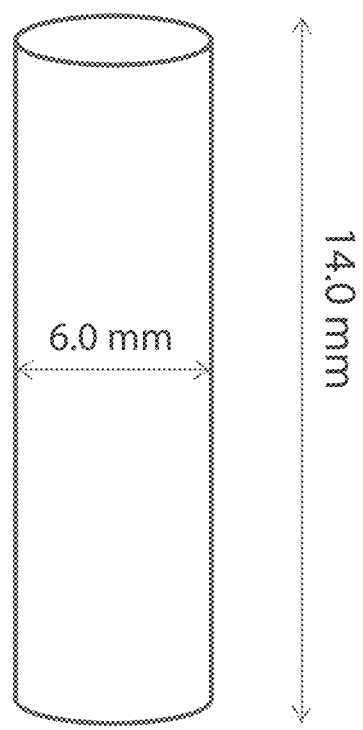
FIG. 4 depicts an exemplary disposable mold for use in forming the hydrogel component of a nasal stimulator device.

In one variation of curing the hydrogel formulation, disposable molds are used, e.g., as shown in FIG. 4. The disposable molds form a continuous shell of the conductive hydrogel formulation around the sleeve, while filling the space inside the slot and the sleeve just next to the electrode. As noted in the figure, the tube may be made from low cost biocompatible, processable material that is transparent to UV radiation, e.g., polyethylene, polyvinylidene fluoride (PVDF), polypropylene (non-UV absorbing grades), polystyrene, ABS and the like. The tube is typically open at one end and closed at the other, and may have an internal diameter of about 6.0 mm, a length of about 14 mm, and a wall thickness ranging from about 0.20 to about 1.0 mm. Other variations of the tube may have an internal diameter ranging from about 3.0 to about 10 mm, and a length ranging from about 5.0 mm to about 20 mm.

Figure 5:
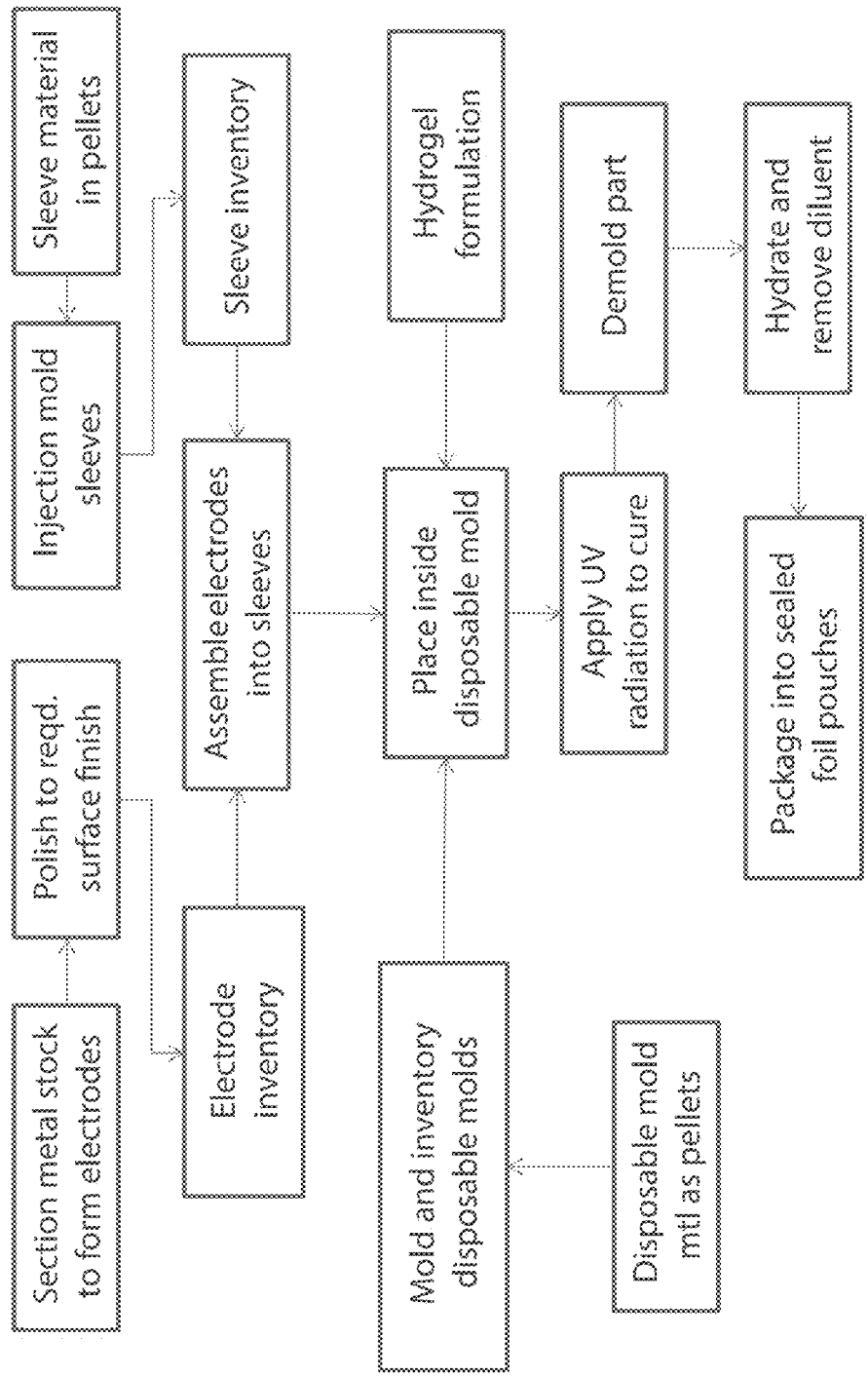
FIG. 5 illustrates an exemplary assembly process for the disposable component.

The disposable molds may be injection molded just in time for use in the curing process. An exemplary assembly and curing process, as shown in FIG. 5, may track to transport parts and subassemblies, and robot to position them. In this process, the electrodes, shaped as rods, springs or foils are assembled into the sleeves that are injection molded separately. The preassembled electrode and sleeve assembly may be inventoried and provided to the final assembly process depicted in FIG. 5, or they may be assembled on line, as shown in FIG. 5.

The conductive hydrogel formulations may be contained in sealed containers that are opaque and isolated from air. The formulations may also be de-aerated prior to being charged into the container. In some variations, the disposable molds are injection molded on line, and are stored in work in process inventory. Long term storage of disposable molds is preferably avoided, since long term storage would introduce dust particles into the molds, and would then require the disposable molds to be washed or cleaned prior to use. Next, the electrode subassembly is placed inside the disposable mold and a specified volume of hydrogel formulation is discharged into the disposable mold. The disposable mold is then moved to a station in which radiation sources are placed in order to provide uniform radiation on all sides of the disposable mold. Temperature is controlled by flowing nitrogen through the station, which also maintains the curing mixture in an oxygen free environment. In this instance, the range of temperature of cure is 30-45 degrees Celsius and the cure times range from about 1 to about 15 minutes. The subassembly is then removed from the disposable mold and the disposable mold discarded after the cure is complete.

In some variations, de-molding can be accomplished by application of a rapid cooling pulse, e.g., by a brief immersion into water at 0 degrees Celsius. The electrode subassembly comprising a hydrogel shell may then be immersed in deionized water for a period of 2-24 hours in order to remove unreacted monomers and the diluent. The temperature of the deionized water may range from about 35 to about 50 degrees Celsius or from about 10 to about 40 degrees Celsius. The electrode subassembly, also called the disposable unit, is then removed from the water, briefly dried to remove excess water, then packaged in a sealed pouch to be ready for sterilization.

Figure 8A:
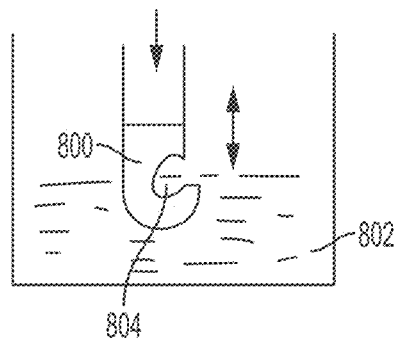
FIGS. 8A-8C depict exemplary methods for shaping the hydrogel included in the nasal stimulator device tip.
Figure 8B:
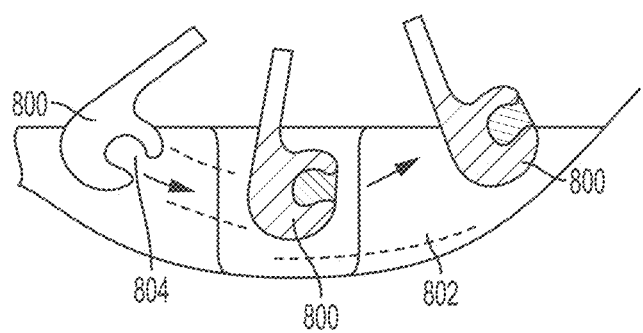
Figure 8C:
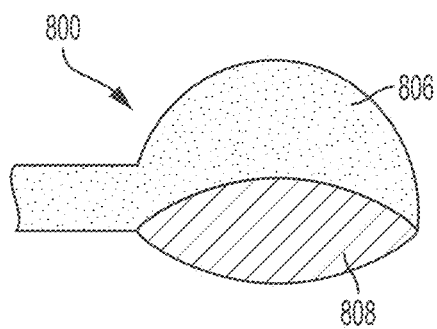

Alternative manufacturing methods for forming the hydrogel into a suitable shape for use with a nasal stimulator device are also described herein. Some variations of the method include a dip-coating and spray technique. For example, the tip of a prong(s) (800) of a nasal stimulator can be dipped up and down (in the direction of the arrows) into the hydrogel (802) repeatedly, as shown in FIG. 8A, or the prong(s) used to scoop the hydrogel (802) at an angle, as shown in FIG. 8B. Here the viscosity of the hydrogel can be adjusted so that the cavity (804) within the prong (800) is filled with the hydrogel after dipping or scooping. Additionally, a primer can be included in the hydrogel formulation to help adhere the hydrogel to the prong when dipping or scooping. The thickness of the hydrogel can be controlled by such factors as the rate of ascent/descent of the prong during dipping or scooping, temperature, and/or viscosity of the hydrogel. The viscosity of the hydrogel may be adjusted to be high enough to allow for shape memory before final curing. After dip-coating by either dipping or scooping, curing of the hydrogel on the prong tip can be performed using UV light (as described above) or by thermal methods. It is understood that multiple dip/cure cycles can be implemented. Next, one or more portions of the hydrogel tip can be masked so that an insulation layer (806) can be applied, e.g., by spraying or adhering, on the hydrogel tip (800) to cover and insulate those portions of the tip (800) that are not intended to be conductive, as shown in FIG. 8C. The insulation layer may comprise any suitable insulator, e.g., a non-conductive polymer. After applying the insulator, e.g., by spraying or adhering, the masked portion (808) of the tip (800) would be conductive. Alternatively, when a mask is not used, the orientation of the hydrogel tip can be controlled so that only insulated areas are sprayed or exposed.

The hydrogel can also be shaped first and then placed at the end of a conductor, e.g., the tip of a nasal stimulator prong. Using such methods, the shaped hydrogel portion can be made ahead of time and then hydrated in bulk, and/or cleared of excess diluent and/or excess unreacted monomer in bulk, stored as a hydrogel/conductor subassembly prior to hydration, or stored during hydration (i.e., stored by leaving in a saline solution).

Shaping of the hydrogel can be accomplished in any suitable fashion. In one variation, the hydrogel formulation is poured into a tray and then conductors are placed in the formulation. The formulation is then cured to form a hydrogel sheet and the sheet shaped by cutting using a laser cutter, a die cutter, a blade, etc. The cut hydrogel may be referred to as a hydrogel preform. If desired, the cured hydrogel can also be shaped to include a bulge. Alternatively, the hydrogel formulation can be poured into a tray including individual molds or cavities having a desired shape, e.g., a bulge. The hydrogel shape formed by the individual molds or cavities may also be referred to as a hydrogel preform. In some instances, cutting and molding may be used in combination in a manner where the hydrogel is cut into a molded preform.

Figure 9A:
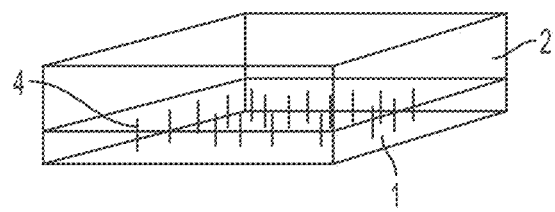
FIGS. 9A-9I depict exemplary methods for shaping the hydrogel by molding and then cutting.
Figure 9B:
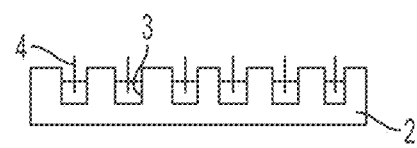
Figure 9C:
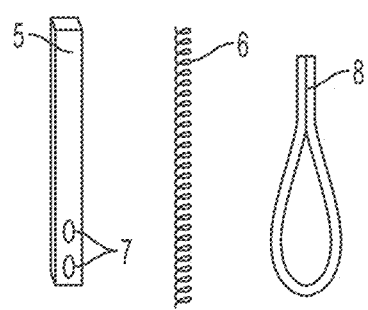

More specifically, and as shown in FIGS. 9A-9I, the hydrogel mixture (1) is first poured into a tray (2). As shown in FIG. 9B, tray (2) can be configured to include individual molds or cavities (3) into which the hydrogel (1) is poured. Conductors (4) may then be placed inside the hydrogel (1) prior to curing. The conductors may have any suitable form and be made from any suitable conductive material. For example, and as depicted in FIG. 9C, the conductors may be configured as a metallic strip (5) with holes (7), a coil spring (6), or a wire that is bent/shaped, e.g., into a loop (8), etc. These conductor configurations may be useful for creating a mechanical lock between the hydrogel and the conductor. In some instances the metallic strip (5) is configured without holes.

Figure 9D:
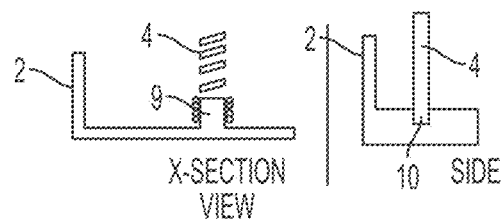
Figure 9E:
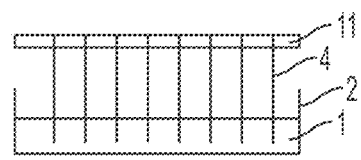
Figure 9F:
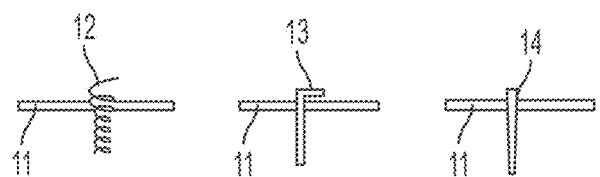

Placement of the conductors into the hydrogel formulation can include the use of locating or capturing features. The locating and capturing features can also help with insertion of the conductors to a desired depth into the hydrogel. For example, as shown in FIG. 9D, an end of conductor (4) can be placed on the tray with the help of a locating feature configured as a peg (9) or a well (10). The end of conductor (4) can also be placed with the help of a capturing feature such as plate (11), which is provided above the tray (2), as depicted in FIG. 9E. In such instances, plate (11) may be configured to capture conductors based on their geometry, e.g., the conductor may have a larger section (12) at one of its ends, have a bent/deformed section (13), or have a clamping or interference fit (14) with plate (11). After the conductors have been placed into the hydrogel, the hydrogel is cured according to any one of the methods described herein. When the hydrogel has been molded/cured into a sheet, the hydrogel can thereafter be formed into a desired shape, e.g., by a laser cutter, a die cutter, a blade, etc. The component created by shaping (element 16 in FIG. 9G), either by cutting or molding, may be referred to as a conductor-hydrogel subassembly (element 17 in FIG. 9G).

Figure 9G:
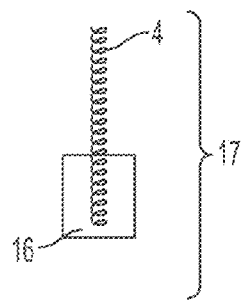
Figure 9H:
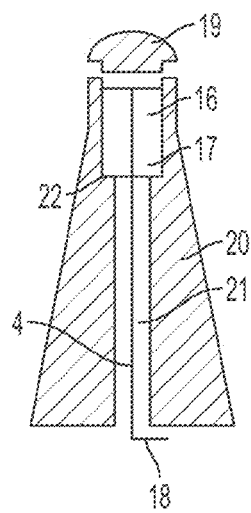
Figure 9I:
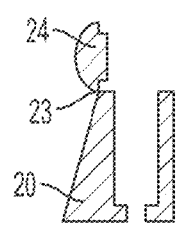

As shown in FIG. 9G, the conductor-hydrogel subassembly (17) can be subsequently hydrated and stored in an aqueous environment until used for further assembly of the tip of a nasal stimulator device, or it may be stored dry for later processing. According to one variation, as shown in FIG. 9H, assembly of the conductor-hydrogel subassembly (17) into a molded part (20) to create the desired final tip assembly can include dropping the subassembly (17) into a hollow shaft (21) of the molded part (20) such that the hydrogel (16) rests on a stepped section (22) inside the shaft (21). Here the conductor (4) may be bent/deformed at the location where it exits the shaft (21), e.g., to create a mechanical lock between the subassembly (17) and the molded part (20). Referring to FIG. 9I, a cap (24) may also be included as part of the molded part (20) by, e.g., a hinge-like mechanism (23).

The hydrogel can also be incorporated into the nasal stimulator device tip by controlled dispensing of the hydrogel formulation, e.g., by computer numerical control (CNC) or robotics, or by hand, directly into a cavity of the tip assembly. Controlled dispensing can be accomplished by tilting mechanisms to ensure vertical alignment of the window, or the use of guides, but is not limited thereto. It is understood that other suitable controlled dispensing processes can be employed. A controlled dispensing method may be useful in controlling the size of the bulge of the hydrogel tip.

Figure 10A:
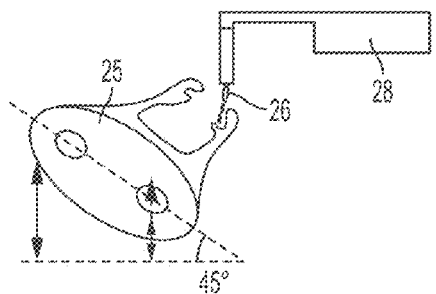
FIGS. 10A-10C depict exemplary dispensing methods and dispensing devices for shaping the hydrogel.
Figure 10B:
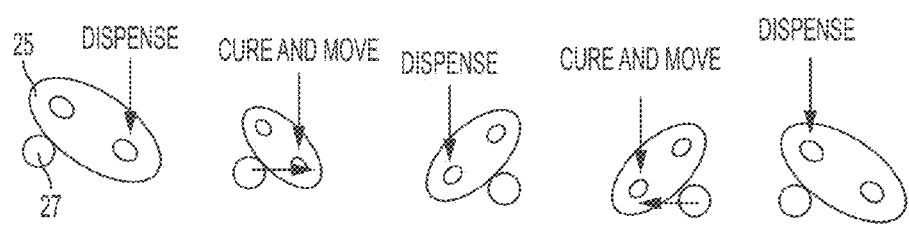

In one variation, tilting during the dispensing process may be useful in controlling the introduction of hydrogel into the device tip. For example, as shown in FIG. 10A, the tip portion (25) can be tilted during dispensing of the hydrogel formulation (26) from a dispenser device (28). The amount of tilting may vary, and can range from about 5 to about 45 degrees. The amount of tilt may be dictated by the geometry of the window being filled. In general, the nasal stimulator device will be tilted so that walls of the window are equidistant about a vertical centerline of the opening, thereby allowing gravity to equally disperse the liquid hydrogel formulation. For example, if the centerline of the window being filled is 45 degrees from the centerline, the nasal stimulator device is tilted (rotated) 45 degrees. Tilting may generally be accomplished using tilting mechanisms such as pins, rollers, and/or plates, etc. FIG. 10B illustrates how a displacement roller (27) can be used to tilt tip portion (25) after the hydrogel formulation has been dispensed and cured. After dispensing the hydrogel formulation into one tip of tip portion (25), the formulation is cured and the displacement roller (27) moved to tilt the tip portion (25) in the opposite direction. The tilting mechanisms generally tilt fixtures (e.g., flat surfaces such as plates) upon which the tip portions have been placed to expose each cavity to the dispenser since the cavity faces inwards on normal orientation (when the tip portion is placed on the fixture), and for dispensing the opening in the tip portions should face the upward direction. In some instances, the fixture may also have alignment pins that complement holes provided in the base portion of the nasal stimulator.

Figure 10C:
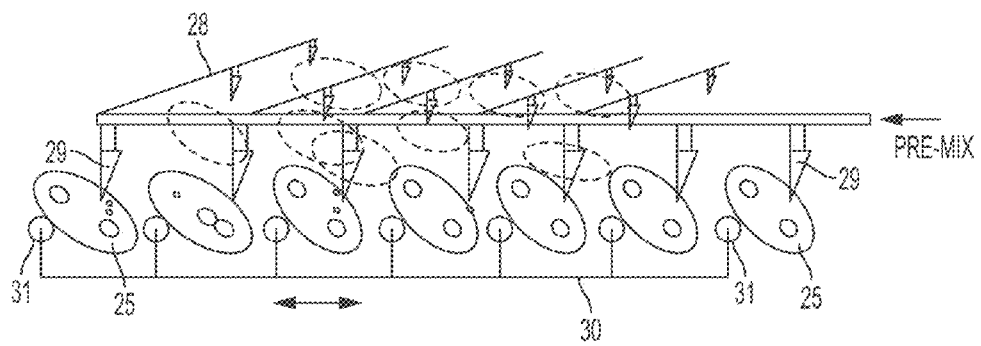

One or several of the tip portions may be tilted during the dispensing process. For example, as shown in FIG. 10C, hydrogel dispenser (28) includes multiple dispenser tips (29) and multiple tip portions (25) disposed on plate (30). Slides (not shown) coupled to multiple rollers (31) are used to tilt the multiple tip portions (25). The plate (30) can also be moved back and forth in the direction of the arrows to achieve a rocking/tilting motion.

Figure 11A:
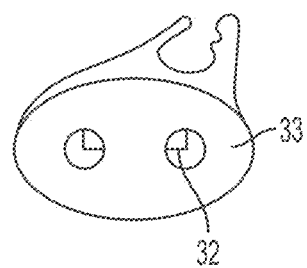
FIGS. 11A-11C depict exemplary structures and methods that may be used to help control dispensing of the hydrogel.
Figure 11B:
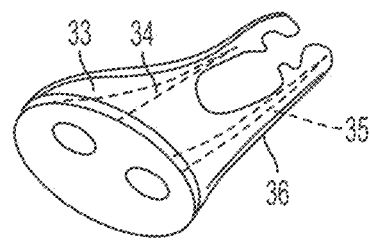
Figure 11C:

In another variation, one or more guides disposed in or on a part of the tip portion may function to control dispensing of the hydrogel by enabling tilting or flexing of the tip portion such that the cavity is substantially perpendicular to the hydrogel dispenser. The guides may be rails and/or slots/slits that interface with a corresponding structure or geometry on a fixture to reversibly attach the tip portion to the fixture and tilt or flex the tip portion so that the cavity can be filled. For example, as shown in FIGS. 11A-11C, an inner slot (32) may be provided in the tip portion (33) (FIG. 11A), a rail or slit (34) may be provided within a lumen (35) of the tip portion (33) or on the outside surface (36) of the tip portion (33) (FIG. 11B), or a slot (37) may be provided in the tip (38) of the tip portion (33) similar to a lock and key combination (FIG. 11C).

Figure 12B:
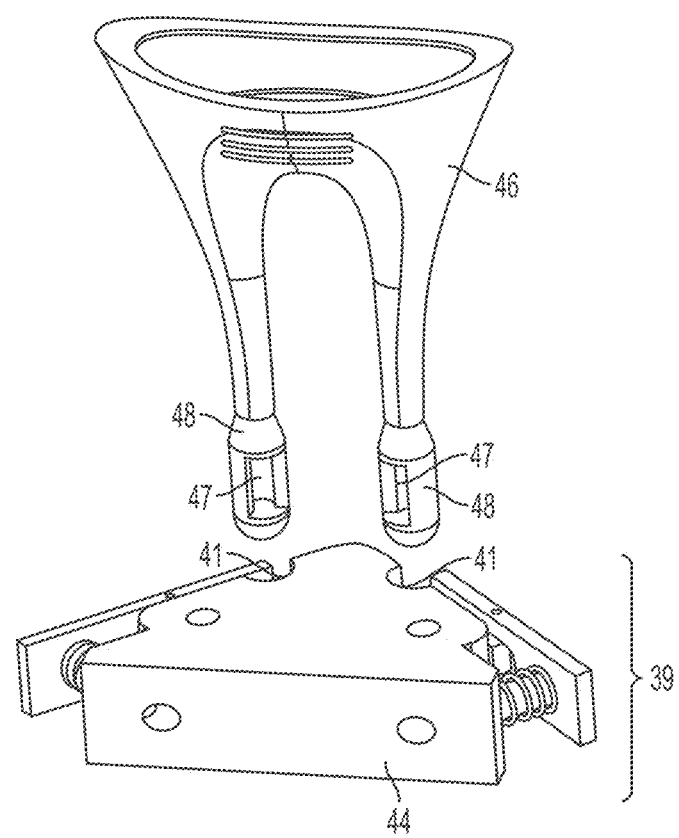
Figure 12C:
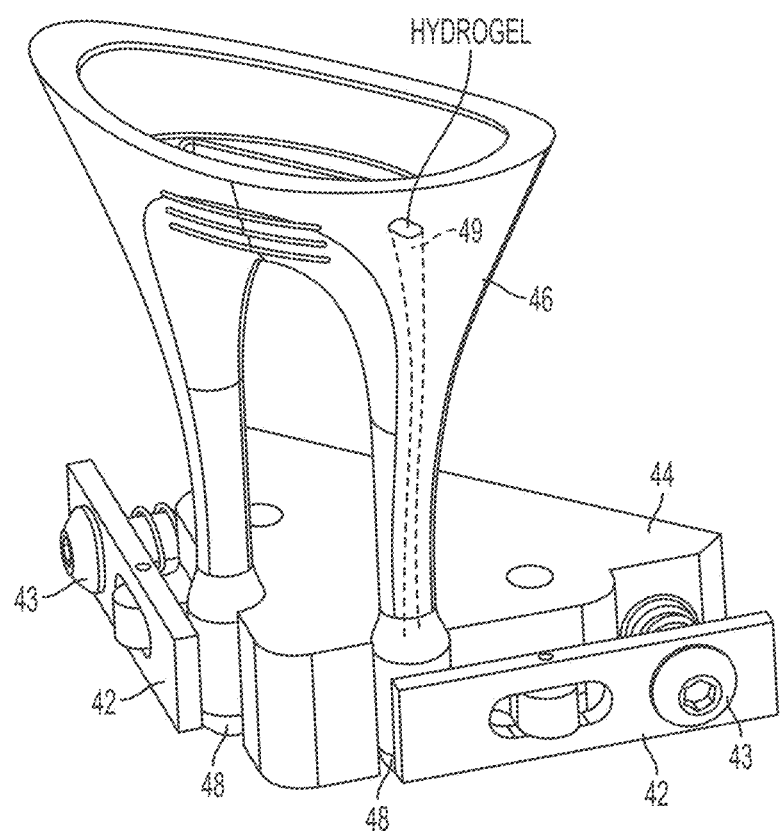
Figure 12D:
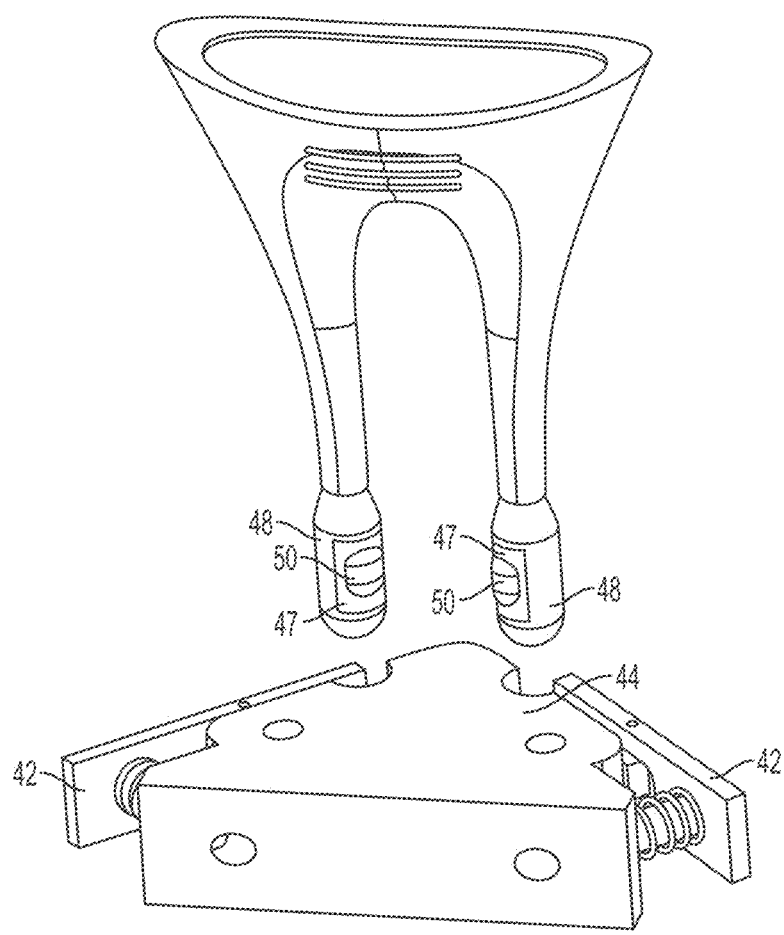

In yet a further variation, the hydrogel of the tip portion can be shaped using a casting process. Here the hydrogel formulation is poured into a mold containing a hollow cavity of the desired shape, and then allowed to solidify. Some variations of the mold may be configured as shown in FIG. 12A. Referring to the figure, mold (39) includes a base block (44), rocker plates (42), screws (43), and compression springs (45). The base block (44) includes one or more casting surfaces (41) configured to form a bulge in the hydrogel tip (i.e., a bulge casting surface). The bulge casting surface will typically have the same radius as a distal end of the tip portion (see element 48 in FIG. 12B), and includes a recess such as recess (40) for creating a bulge during casting. Rocker plates (42) compress and secure the tip portions (see FIG. 12 C) to the base block (44) using screws (43) and compression springs (45). The rocker plates may be made from a material that transmits UV light, e.g., an acrylic material. The height of the screws (43) may be adjusted to control the amount of compression imparted by plate (42). More specifically, as shown in FIGS. 12B-12D, the manufacture of a hydrogel tip by casting may include providing a pronged disposable tip (46) with windows (47), and orienting the distal ends (48) such that the windows (47) face the casting surface (41) of the base block (44) of mold (39) (FIG. 12B). The distal ends (48) of the pronged tip (46) are then secured to the base block (44) by tightening of screws (43) so that rocker plates (42) are compressed against the base block (44) (FIG. 12 C). Again, the tips (46) are loaded into the mold with the windows facing the casting surface. A UV curable hydrogel formulation as described herein can then be injected through a channel (49) in the disposable tip (46) that is fluidly connected to the distal ends (48) in a manner that delivers hydrogel to the windows and the casting surface (FIG. 12C). As stated above, the casting surface includes a recess for forming a bulge in the hydrogel. After the hydrogel formulation is injected into the tip portion (46), UV light can be applied to cure the hydrogel. Either the rocker plates or base block can be made from a material that transmits UV light. An exemplary UV transmissive material comprises glass. Here the UV light is capable of being transmitted through the base block (44) and distal end (48). The rocker plates (42) are then released so that the distal ends (48) can be removed from the base block (44). As shown in FIG. 12D, the resulting hydrogel formed by the casting process has a bulge (50) that protrudes from window (47). Although a single mold is shown in FIGS. 12A-12D, it is understood that a ganged array of molds could be configured and employed for large scale production.

Figure 13:
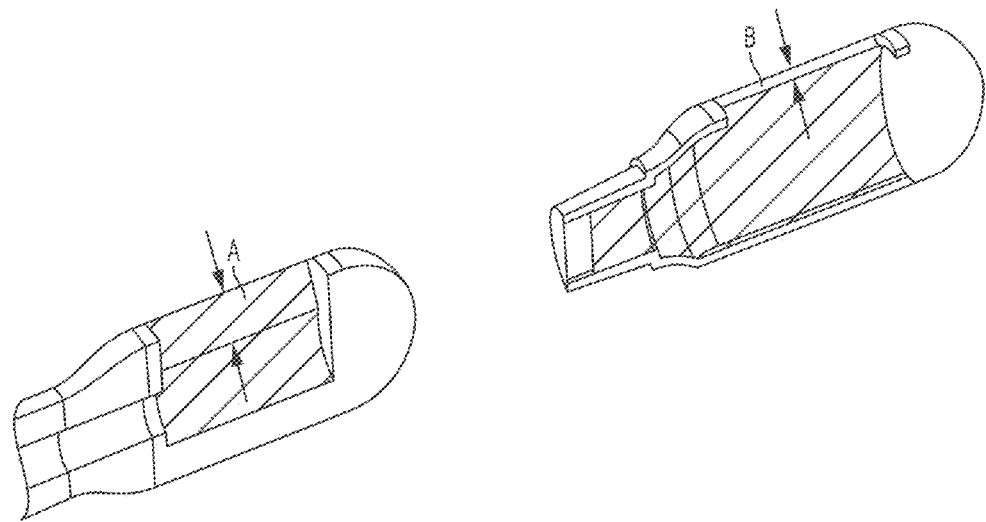
FIG. 13 shows an exemplary thin walled tip capable holding larger volumes of hydrogel.

Some methods of manufacturing include decreasing the wall thickness at the end of the tip portions so that the volume of hydrogel can be increased in the tip portions. In one variation, this is accomplished by molding the tip from a single component and using a micro-molding process and material. Using this process, for example, the wall thickness of the tip portion can be decreased from thickness A (shown between the arrows on the left) to thickness B (shown between the arrows on the right) in FIG. 13 to thereby increase the volume within the tip end. Other methods may include steps that create a high volume to surface area ratio to maintain the desired level of hydration of the hydrogel.

Tip Assembly Methods

Methods for assembling the tip portion of a nasal stimulator device are further described herein. These assembly methods may be mixed and matched with the various ways of shaping the hydrogel, as described above. The methods may also be used to assemble the disposable tip portion shown in FIG. 2, or tip portions having other configurations. Some variations of the tip portion may require only partial assembly before the hydrogel is added to them. In general, the assembly methods include steps that fix the hydrogel within the tip portion, either mechanically (e.g., by hydrating after placing the hydrogel into the tip, interference fit, screw fit, etc.), or chemically (e.g., by epoxy, bioadhesives, ultrasound, etc.).

Figure 14A:
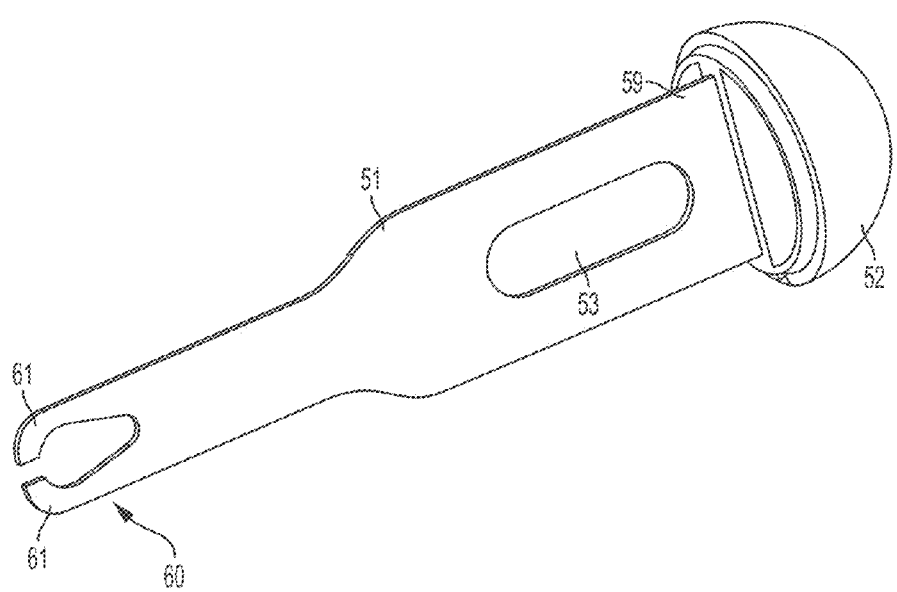
FIGS. 14A-14D show an exemplary tip assembly structure and method of attaching the structure to a prong of a nasal stimulator device.
Figure 14B:
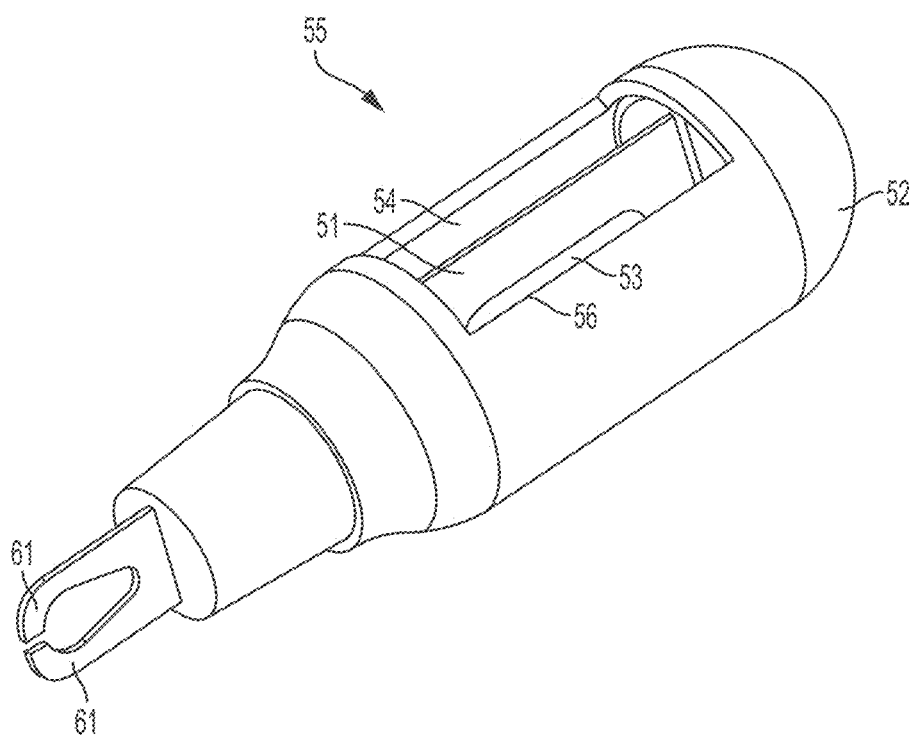

In variations where the hydrogel formulation is dispensed into the window of the tip portion, the tip may include an electrode (51) having a distal end (59) that is insert molded into a cap (52) and a flexible, frangible, or spring-like proximal end (60) comprising arms (61), as shown in FIG. 14A. The electrode (51) may include a slot (53) that functions to provide mechanical retention of the hydrogel within the cavity (element 54 in FIG. 14B) of a tip assembly (element 55 in FIG. 14B). In its partially assembled state, as provided in FIG. 14B, the hydrogel can be injected using a dispensing system and method as described above, into cavity (54) through window (56). Here formation of the hydrogel bulge may be controlled by the surface tension and/or the viscosity of the uncured hydrogel.

Figure 14C:
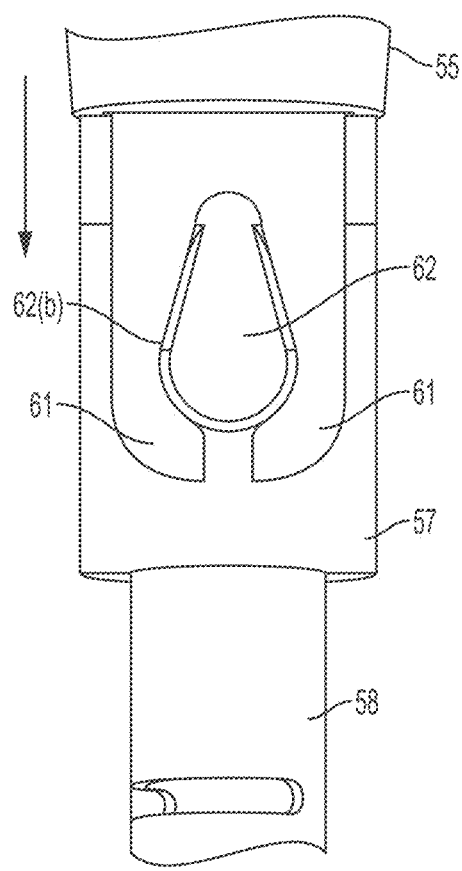
Figure 14D:
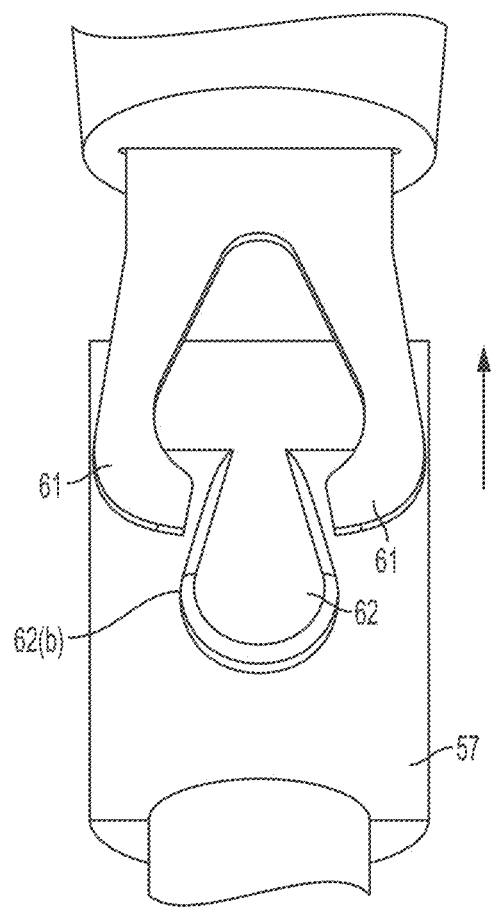

After curing of the hydrogel, the tip assembly may be attached to a nasal stimulator device as depicted in FIG. 14C. Referring to FIG. 14C, the tip assembly (55) is attached to the rest of the disposable tip portion via a retainer block (57) at the distal end of a flex tube (58) (within the prong of a stimulator device) that has a tip retainer (62b) with a ramp surface (62). The electrode (51) of the tip assembly (55) is pushed in the direction of the arrow so that it is forced to follow the ramp surface (62). The flexible/frangible nature of the electrode arms (61) allow them to snap back to their original configuration when fully inserted to substantially surround the tip retainer (62b). The electrode arms (61) may be configured to permanently deform when pulled upward in the direction of the arrow and detached from the tip retainer (62b) so that the tip assembly cannot be reused, as shown in FIG. 14D.

Figure 15A:
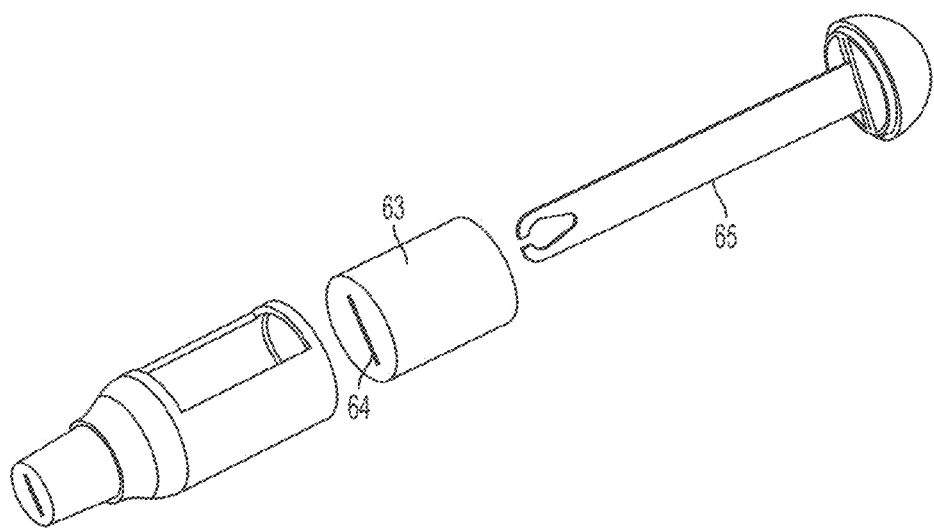
FIGS. 15A-15C show an exemplary method where a hydrogel preform is included in the tip assembly and then hydrated.
Figure 15B:
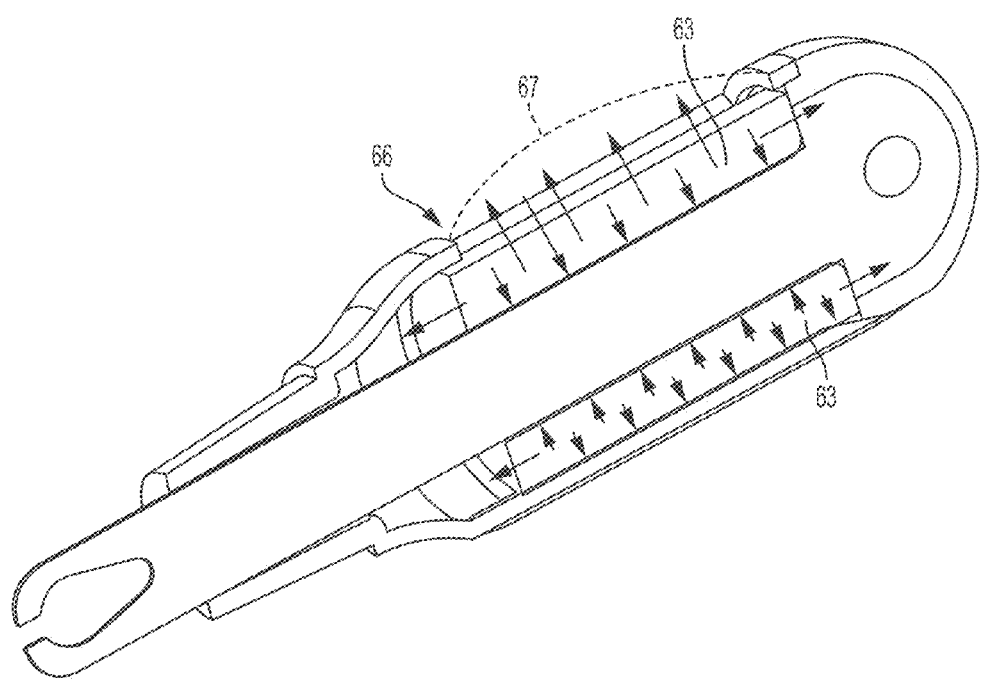
Figure 15C:
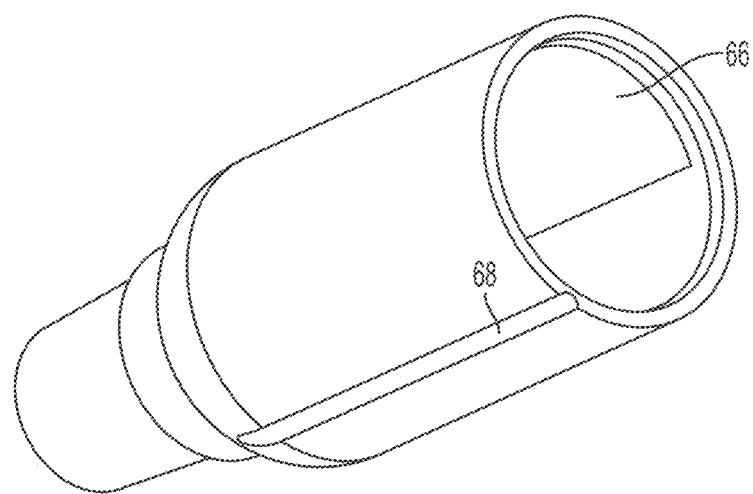

In variations where the hydrogel is preformed using, e.g., any of the methods described above, the hydrogel may be preformed as a cylinder (63) having a slot (64) for accepting an electrode (65), as shown in FIG. 15A. Here the hydrogel is an unhydrated preform that is hydrated after the tip assembly is fully assembled. It is understood that the hydrogel preform may or may not be washed of excess unreacted monomer prior to integration into the tip assembly. During the hydration process, the hydrogel preform (63) will generally swell in the direction of the arrows, fill open spaces, and expand through window (66) to create a stimulation (contact) surface (67). Furthermore, given that the clearance between the electrode (65) and slot (64) is small, the electrode is typically fully contacted by the hydrogel in the initial phase of hydration (e.g., upon 20% hydration). This is a beneficial safety feature since it ensures that when a patient uses the nasal stimulator device, the full surface of the electrode is carrying the electrical current. An angular slot (68) on the exterior of the tip assembly opposite the window (66) can be used to align and mate the tip assembly to a corresponding structure in a dispensing cassette during the manufacturing process, as further described below.

Figure 16A:
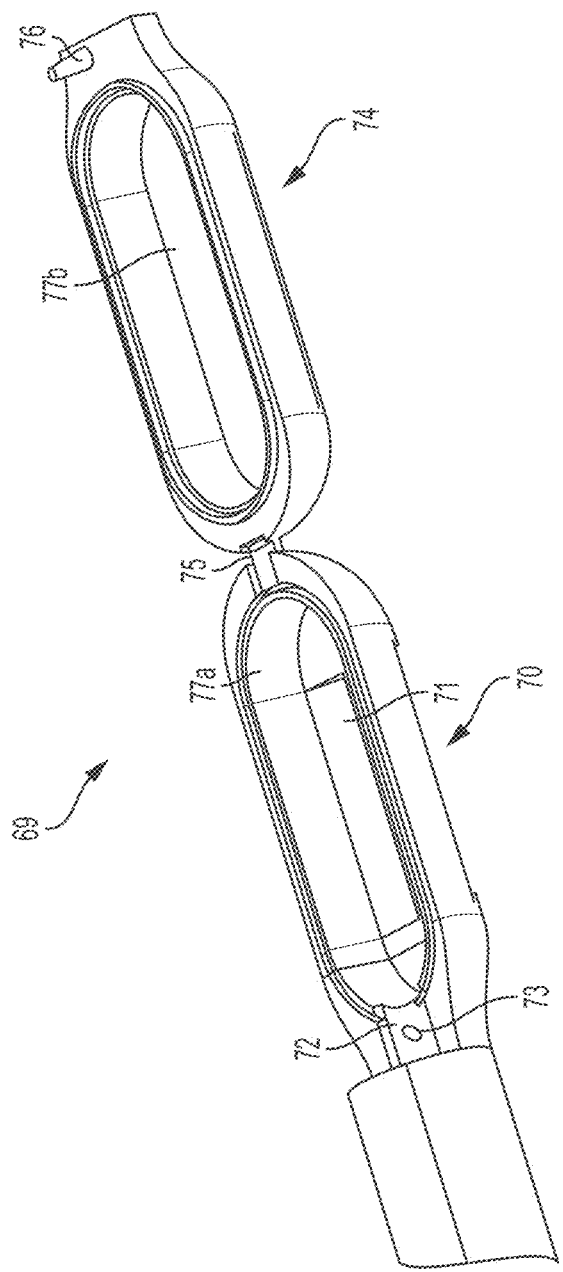
Figure 16D:
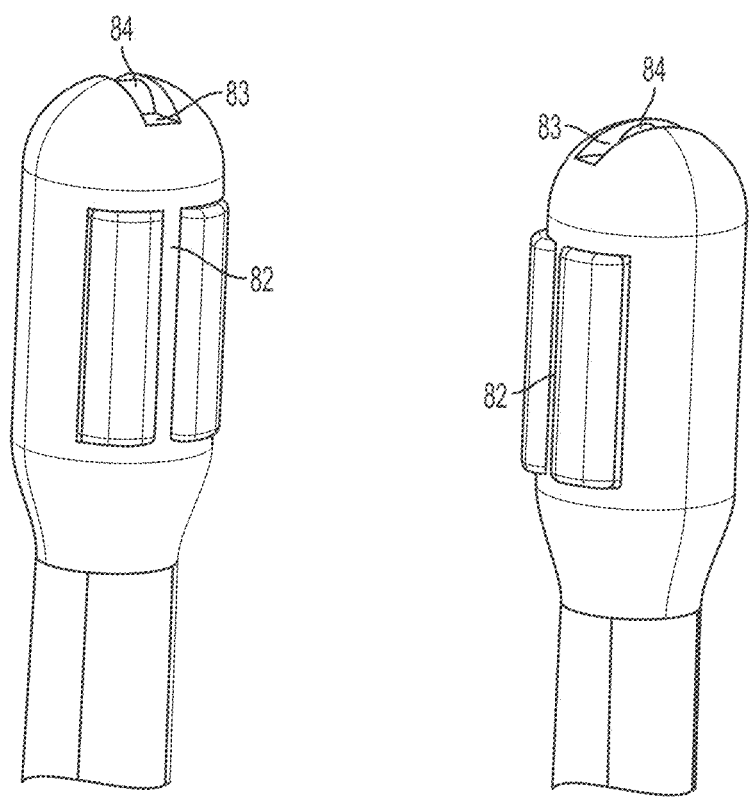

In other variations, a hydrogel preform may be placed into a tip assembly that includes a hinge, e.g., a living hinge. For example, as shown in FIG. 16A, the tip assembly (69) may be configured to include a first side (70) having a cavity (77a) for placement of the hydrogel preform (not shown), a window (71) that allows the hydrogel preform to expand, a channel (72) for slidable engagement of an electrode (not shown), and a hole (73). First side (70) is coupled to a second side (74) via a living hinge (75). The second side (74) includes a cavity (77b), a tapered boss (76) that is accepted by the hole (73) when the second side (74) is folded over to contact the first side (70) at living hinge (75). The tapered boss (76) and hole (73) have an interference fit and may be welded together prior to hydration of the hydrogel preform. In another example, the tip assembly may include a deflectable electrode (78) capable of being deflected in the direction of the arrow to allow a hydrogel preform (79) to be installed in the tip assembly, as shown in FIG. 16B. Here the electrode includes a hole (73) for acceptance of the tapered boss (76) when the first (70) and second (74) sides are rotated at the living hinge (75) to close the sides together. Instead of a tapered boss and hole, the sides may also be secured together using a tongue and groove configuration. For example, as shown in FIG. 16C, a female tapered groove (80) can be configured to have an interference fit with a male tapered tongue (81). Other variations of the tip assembly are shown in FIG. 16D, and include a hydrogel retention bar (82) to help secure the hydrogel within the tip and/or a living hinge (84) recessed within a slot (83) provided in the surface of the tip to help prevent abrasion of nasal tissue.

Figure 17A:
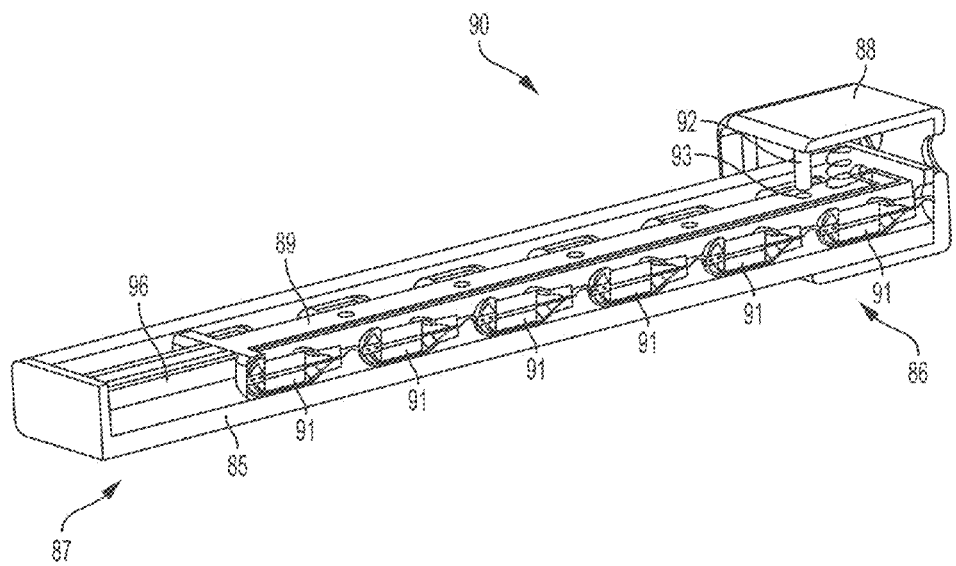

The manufacturing methods may also employ the use of a dispensing cassette to assemble the tip assemblies in bulk. Bulk packaging may reduce the amount of packaging materials and volume, which is convenient for the end user. An exemplary dispensing cassette is provided in FIGS. 17A-17F. Referring to FIG. 17A, the dispensing cassette (90) may include a cassette housing (85) having a proximal end (86) and a distal end (87), and an alignment block (88) coupled to the proximal end (86), and a constant force spring (89). A plurality of tip assemblies (91) can be stored in the cassette housing (85) and held in place by the constant force spring (89), which pushes the tips (91) against the alignment block (88). A plurality of holes (93) are provided in the constant force spring (89), which are spaced apart a distance equal to the length of one tip assembly (91). When the dispensing cassette (90) is at rest, a pin (92) of the alignment block (88) is not engaged with a hole (93) in the constant force spring (89). As provided in more detail in FIG. 17B, when the dispensing cassette is at rest, a spring (94) in its unrestrained state pushes pin (92) out of hole (93) in the constant force spring (89), and the constant force spring (89) pushes the tips (91) (see FIG. 17A) back toward surface (95) of alignment block (88). When the dispensing cassette is activated by the user for the attachment of the tips (91) to the rest of the nasal stimulator device (not shown) as depicted in FIG. 17C, the alignment block (88) is depressed to compress spring (94) and allow engagement of pin (92) with constant force spring hole (93) to release the load provided by constant force spring (89) against the tips (91) while a tip is being attached. A wick (96) can also be provided to keep a supply of moisture in the dispensing cassette so that the hydrogel in the tips (91) do not dry out prematurely. The wick (96) may be saturated with a fluid such as saline. As previously described, the tip assemblies may include a slot (97) (as shown in FIG. 17D) configured to engage a complementary structure of the cassette housing (99) so that angular alignment of the electrodes can be controlled. For example, as depicted in FIG. 17E, the slots (97) in the tips (91) engage ribs (98) of the cassette housing (99).

Figure 17B:
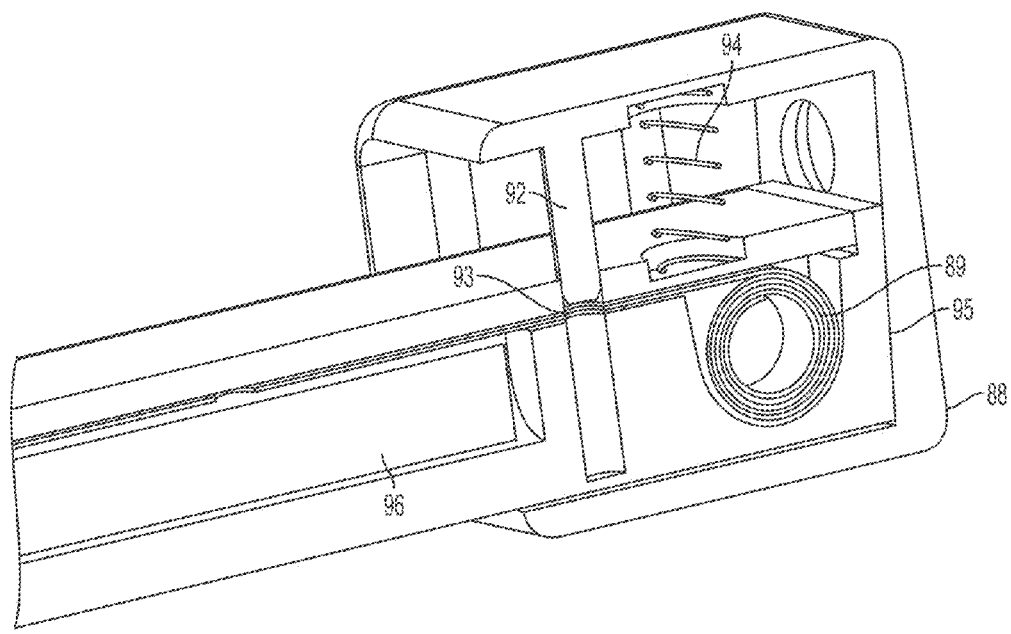
Figure 17C:
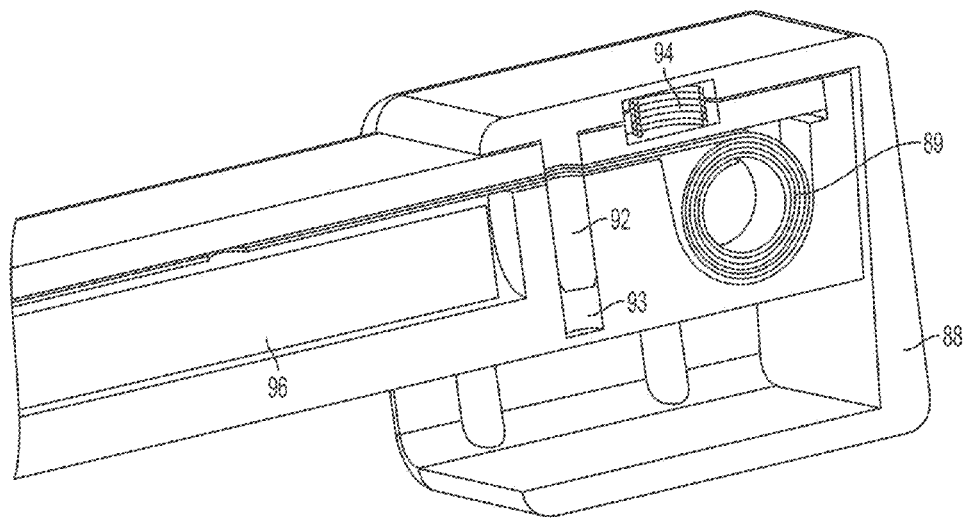
Figure 17E:
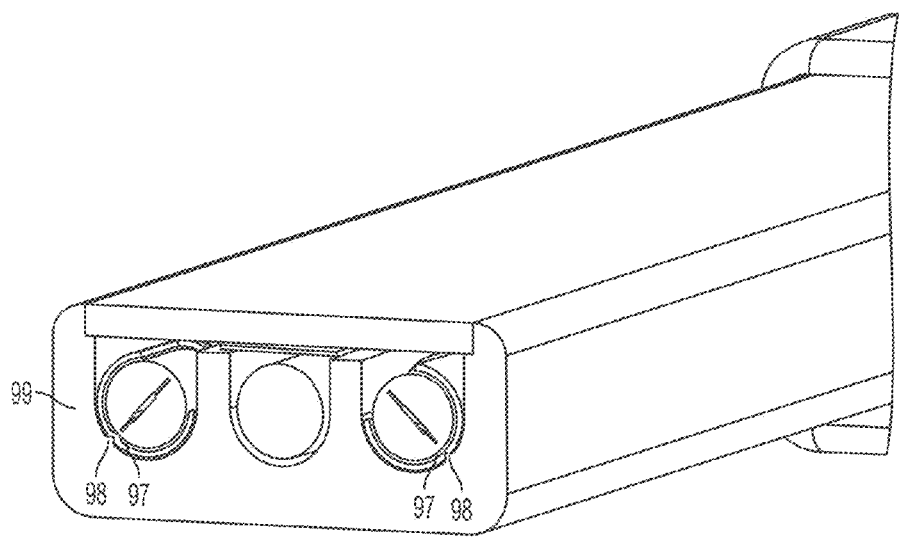
Figure 18B:
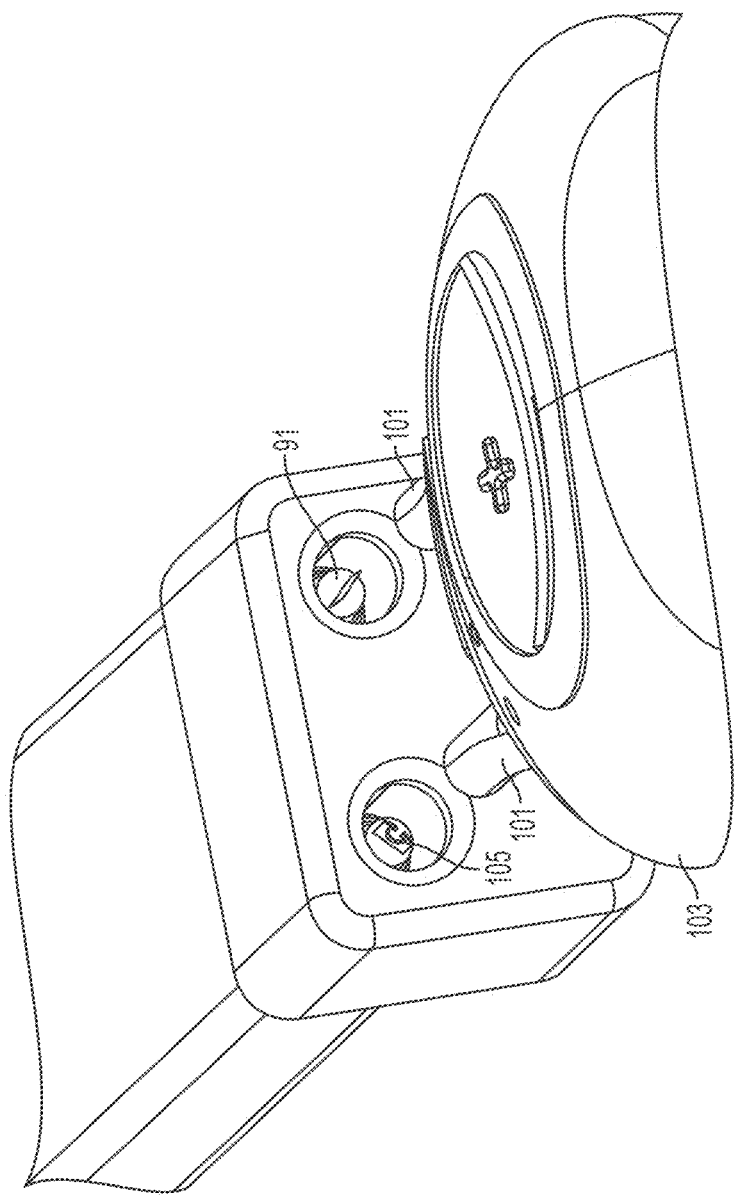
Figure 18C:
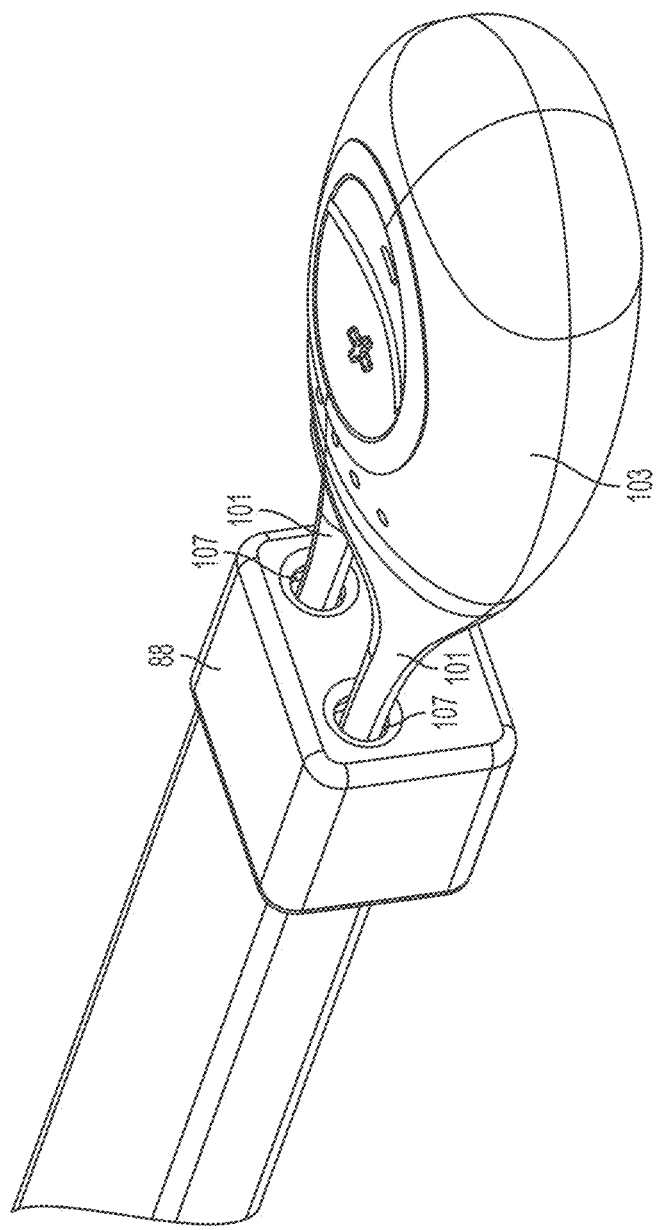
Figure 18D:
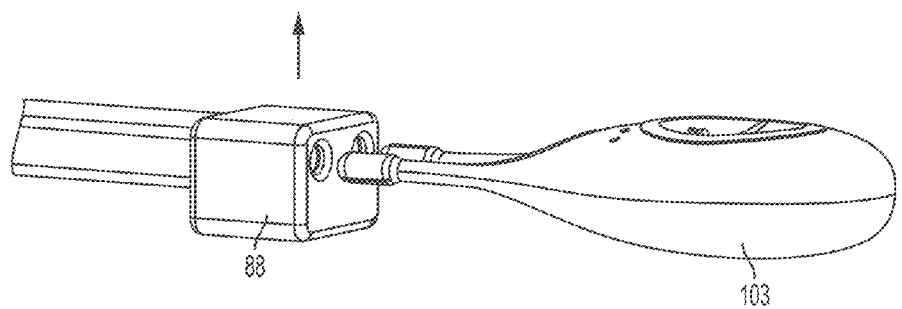

Some variations of the manufacturing method combine the electrode and tip retainer shown in FIG. 14C with the dispensing cassette described in FIGS. 17A-17C, as illustrated in FIGS. 18A-18D. First, the alignment block (88) is depressed in the direction of the arrow (FIG. 18A) to expose a new tip assembly (91) that can be accessed by the pronged portion (101) of the nasal stimulator device (103) (FIG. 18B). The electrode (105) is aligned to attach to a connector (not shown) in the prong (101). Next, the device (103) and prongs (101) are advanced through the access holes (107) in the alignment block (88) until a tip (not shown) is attached as described in FIG. 14C. After attachment, the device (103) may be withdrawn from the alignment block (88) and compression force on the alignment block (88) may be released in the direction of the arrow, as shown in FIG. 18D.

Figure 19A:
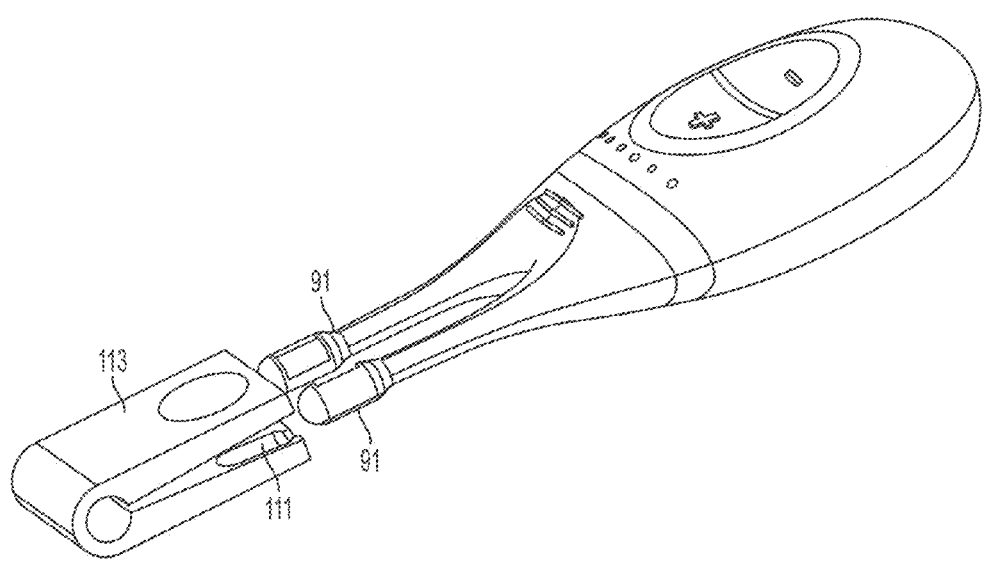
FIGS. 19A-19C show an exemplary tool and method for removing tip assemblies from the base unit.
Figure 19B:
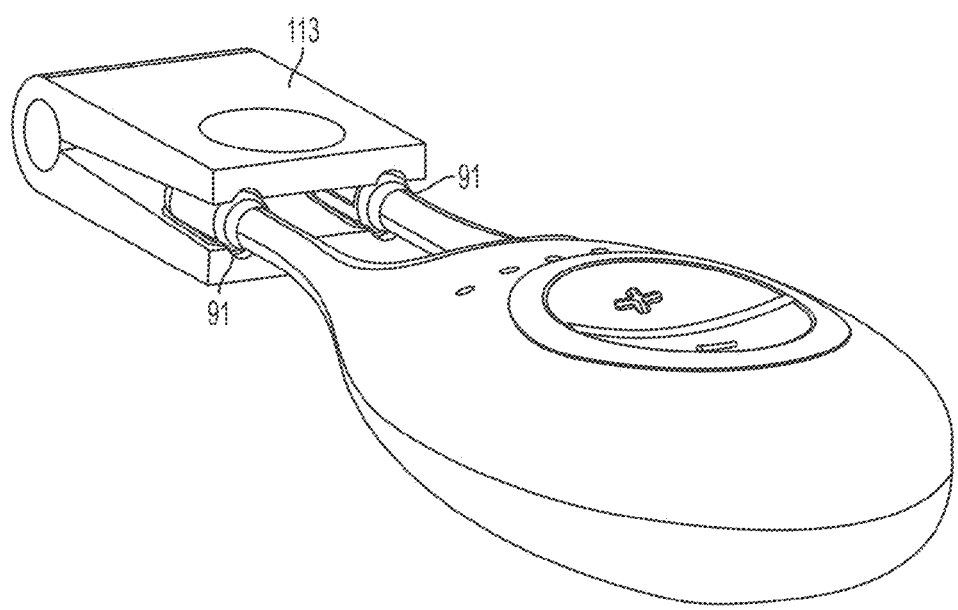
Figure 19C:
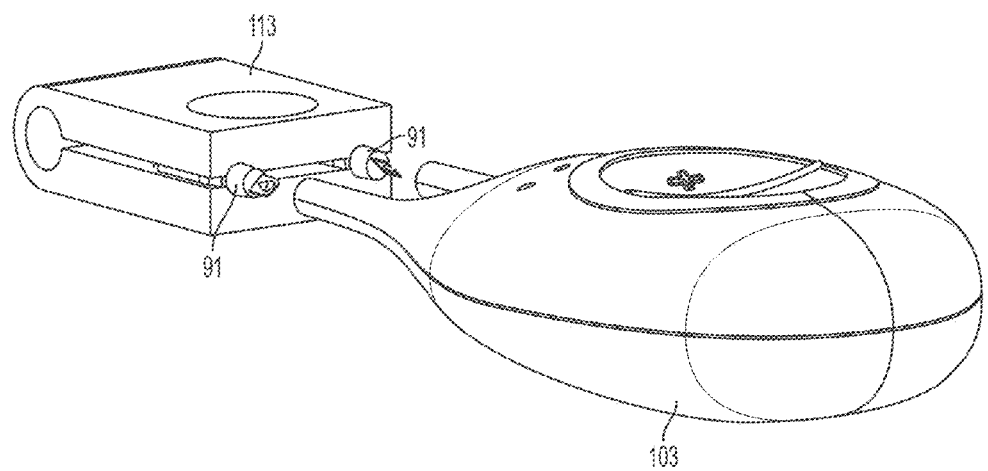

If tip detachment is desired, a tip removal tool may be employed, as depicted in FIGS. 19A-19C. Referring to FIG. 19A, tip assemblies (91) can be inserted into a cavity (111) of tip removal tool (113) that resembles a clasp. The removal tool (113) can then be pinched to compress the tip assemblies (91) within the removal tool (113), as shown in FIG. 19B. While maintaining the compression force, the device (103) can be pulled away from the tip removal tool (113) to detach the device (103) from the tip assemblies (91), as shown in FIG. 19C.

Figure 20A:
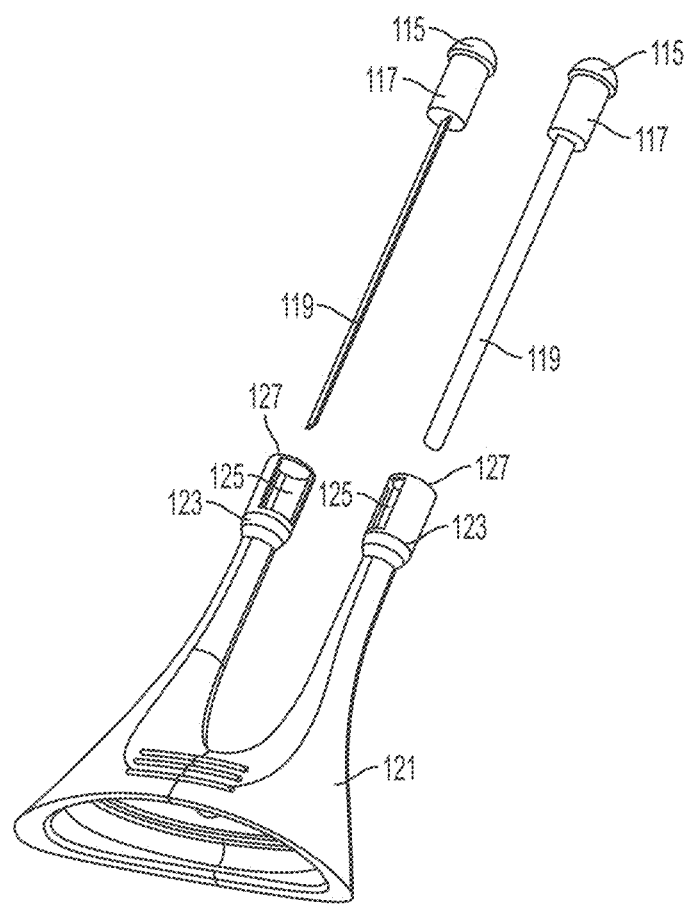
FIGS. 20A-20B show additional exemplary tip assembly structures and assembly methods thereof.
Figure 20B:
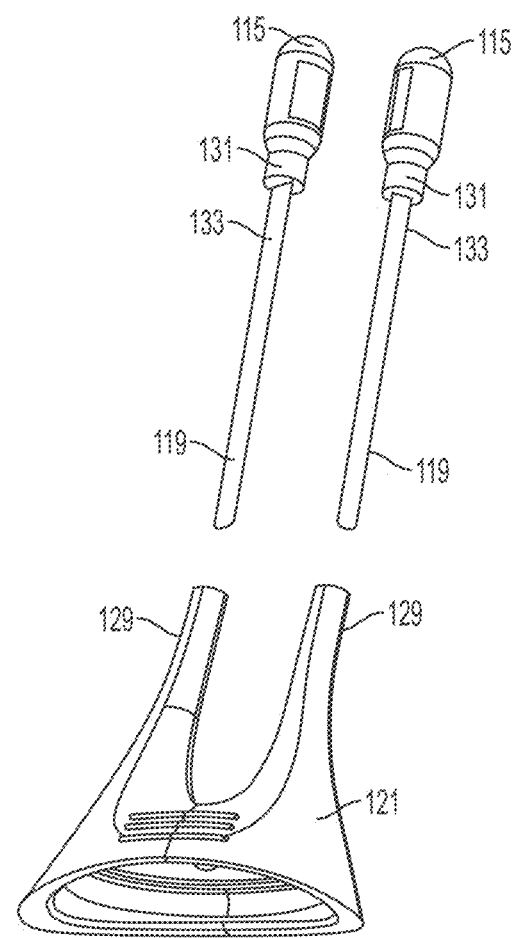

In yet further variations, the manufacturing methods include steps that attach a flexible base unit to a rigid tip assembly. For example, as shown in FIG. 20A, caps (115) on hydrogel preforms (117) may be provided. Rigid, elongate electrodes (119) may extend from the caps (115) for advancement through a flexible base (121). Segments (123) including windows (125) are attached to the flexible base (121). As shown in the figure, segments (123) have an open top (127) so that the hydrogel preforms (117) can be loaded therein. After the electrodes (119) are advanced into the flexible base (121) the caps (115) can be fixed to the flexible base, e.g., by welding. In another example, as shown in FIG. 20B, the flexible base (121) is configured to include tapered ends (129) that accept complementary structures (131) near the distal end (133) of elongate electrodes (119).

Methods of Use

Methods for stimulating nasal or sinus tissue (and the lacrimal gland) are also described herein. In one variation, the method includes placing an arm of a nasal stimulator device against a nasal or a sinus tissue, the arm having a distal end and an electrically conductive hydrogel disposed at the distal end; and activating the nasal stimulator device to provide electrical stimulation to the nasal or the sinus tissue, where the electrically conductive hydrogel is used to facilitate an electrical connection between the nasal stimulator device and the nasal or the sinus tissue. As stated above, the conductive hydrogel may comprise a first monomer; a second monomer; and a photoinitiator, where the first monomer is an acrylate monomer and the electrically conductive hydrogel has one or more characteristics that adapt it for use with a nasal stimulator device. The conductive hydrogel may include monomers, diluents, photoinitiators, and other components as described herein, e.g., the components provided in Table 1 and Table 3. Again, the formulations are subjected to UV radiation to form a cross-linked, conductive hydrogel. The conductive hydrogels used in these methods may include those listed in Tables 2 and 5.

Generally, when one or more nasal or sinus afferents (trigeminal afferents as opposed to olfactory afferents) are stimulated, a lacrimation response is activated via a nasolacrimal reflex. This stimulation may be used to treat various forms of dry eye, including (but not limited to), chronic dry eye, episodic dry eye, seasonal dry eye. To provide continuous relief of dry eye symptoms, nasolacrimal stimulation from one to five times a day may be needed. In some instances, the stimulation may be used as a prophylactic measure to treat users which may be at an increased risk of developing dry eye, such as patients who have undergone ocular surgery such as laser vision correction and cataract surgery. In other instances, the stimulation may be used to treat ocular allergies. For example, an increase in tear production may flush out allergens and other inflammatory mediators from the eyes. In some instances, the stimulation may be configured to cause habitation of the neural pathways that are activated during an allergic response (e.g., by delivering a stimulation signal continuously over an extended period of time). This may result in reflex habitation which may suppress the response that a user would normally have to allergens.

EXAMPLES

The following examples further illustrate the conductive hydrogel formulations as disclosed herein, and should not be construed in any way as limiting their scope.

Example 1

Method of Making an Electrically Conductive Hydrogel For Use With a Nasal Stimulator Device In a round bottom flask wrapped in aluminum foil and provided with a magnetic stirrer, introduce a first monomer, a second monomer, and a photoinitiator. Additional monomers (e.g., a third or fourth type of monomer, etc.) and/or a diluent may also be added. Clamp the flask on top of a magnetic stirrer/heater that is fitted with a nitrogen purge line. After turning on the magnetic stirrer and nitrogen purge, mix the contents of the flask for five minutes to form a monomer mixture. While the monomers are being mixed, insert sleeves of a nasal device (e.g., sleeve (300) shown in FIGS. 3A-3C) into disposable molds (e.g., as shown in FIG. 4) having windows or louvers that open to let in UV light. The sleeves should be oriented vertically within the molds. Next, draw the monomer mixture from the flask into a syringe and cover the syringe with foil. Attach a needle, e.g., a 30 gauge blunt needle, to the syringe. Insert the needle into the sleeve and fill the sleeve with the monomer mixture.

Next, open the louvers and irradiate the molds for about three minutes with UV light. Thereafter, turn the molds horizontally with the louvers facing upward and irradiate the molds for about seven minutes with UV light. Cool the molds before removing the sleeves from them.

Example 2

Preparation of a Silicone Hydrogel Including Methacryloxypropyl Tris (Trimethoxysiloxy) Silane and Methanol Diluent In a round bottom flask wrapped in aluminum foil and provided with a magnetic stirrer, the following was added:
EGMDA (Ethylene glycol dimethacyrlate) (0.081 g)
NVP (N-vinyl pyrollidone) (2.179 g)
GMA (Glyceryl monomethacrylate) (1.112 g)
DMA (Dimethyl acrylamide) (3.917 g)
Methacryloxypropyl tris (trimethyoxysiloxy) silane (2.712 g)
Lucirin (TPO) (0.081 g)
Methanol (2.88 g)

The flask was clamped on top of a magnetic stirrer/heater that was fitted with a nitrogen purge line. The contents of the flask were then mixed for five minutes to form a monomer mixture. While the monomers were being mixed, the nasal device sleeves and disposable molds were prepared as described in Example 1. The monomer mixture was then drawn into a syringe, injected into the sleeves, and irradiated as described in Example 1. The molds were cooled before removing the sleeves from them.

Example 3

Silicone Hydrogel SB1

Silicone hydrogel formulation SB1 was prepared and molded into sleeves as described in Example 1. The components of the SB1 hydrogel are provided below. A diluent was not included in the SB1 hydrogel formulation.

| Monomers | molecular weight (g/gmole) | mole | mass (g) | mole fraction | 10 gram batch (g) | molar ratio to major monomer | wt % |
|---|---|---|---|---|---|---|---|
| | SB1 14020 (for kinetic study (formulated on Mar. 13, 2014) | | | | | | |
| HEMA | 130.14 | 0.0768 | 10.0000 | 0.0964 | 0.9606 | 0.2152 | 9.5299 |
| EGDMA | 198.00 | 0.0018 | 0.3500 | 0.0022 | 0.0336 | 0.0049 | 0.3335 |
| NVP | 111.14 | 0.2969 | 33.0000 | 0.3726 | 3.1700 | 0.8315 | 31.4487 |
| DMA | 99.13 | 0.3571 | 35.4000 | 0.4481 | 3.4006 | 1.0000 | 33.7359 |
| allyl methacrylate | 126.16 | 0.0028 | 0.3500 | 0.0035 | 0.0336 | 0.0078 | 0.3335 |
| methacryloxypropyl trisTrimethoxysiloxy silane | 422.82 | 0.0591 | 25.0000 | 0.0742 | 2.4015 | 0.1656 | 23.8248 |
| lucerin | 348.00 | 0.0024 | 0.8320 | 0.0030 | 0.0800 | 0.0067 | 0.7937 |
| Total | | 0.7969 | 104.9320 | 1.0000 | 10.0800 | | 100.0000 |

Example 4

Silicone Hydrogel SB2

Silicone hydrogel SB2 was prepared as in Example 1. The components of the SB2 hydrogel are provided below. A methanol diluent was included in the SB2 hydrogel formulation.

| Monomers | molecular weight (g/gmole) | mole | mass (g) | mole fraction | 10 gram batch (g) | molar ratio to major monomer | wt % |
|---|---|---|---|---|---|---|---|
| | SB2 14021 (for kinetic study (formulated on Mar. 13, 2014) | | | | | | |
| HEMA | 130.14 | 0.0768 | 10.0000 | 0.0443 | 0.9606 | 0.2152 | 7.4582 |
| EGDMA | 198.00 | 0.0018 | 0.3500 | 0.0010 | 0.0336 | 0.0049 | 0.2610 |
| NVP | 111.14 | 0.2969 | 33.0000 | 0.1714 | 3.1700 | 0.8315 | 24.6120 |
| DMA | 99.13 | 0.3571 | 35.4000 | 0.2061 | 3.4006 | 1.0000 | 26.4020 |
| allyl methacrylate | 126.16 | 0.0028 | 0.3500 | 0.0016 | 0.0336 | 0.0078 | 0.2610 |
| methacryloxypropyl trisTrimethoxysiloxy silane | 422.82 | 0.0591 | 25.0000 | 0.0341 | 2.4015 | 0.1656 | 18.6455 |
| lucerin | 348.00 | 0.0024 | 0.8320 | 0.0014 | 0.0800 | 0.0067 | 0.6211 |
| diluent methanol | 32.04 | 0.9357 | 29.9808 | 0.5401 | 2.88 | 2.6203 | 22.3602 |
| Total diluent & hydrogel | | 1.7327 | 134.9128 | 1.0000 | 12.88 | | 100.0000 |

Example 5

Silicone Hydrogel SB3

Silicone hydrogel SB3 was prepared and molded into sleeves as in Example 1. The components of the SB3 hydrogel are provided below. The SB3 hydrogel formulation included a methanol diluent and the HEMA monomers were replaced with EGDMA monomers, which are more hydrophilic than the HEMA monomers.

| Mononmers | SB3 (Kinetic Study 3) | | | | |
|---|---|---|---|---|---|
| | molecular weight (g/gmole) | mole fraction | 10 gram hydrogel batch (g) | molar ratio to major monomer | Wt Fraction |
| EGDMA | 198.00 | 0.0025 | 0.081 | 0.0103 | 0.0062 |
| NVP | 111.14 | 0.1203 | 2.179 | 0.4963 | 0.1681 |
| GMA | 160.00 | 0.0426 | 1.112 | 0.1759 | 0.0858 |
| DMA | 99.13 | 0.2424 | 3.917 | 1.0000 | 0.3022 |
| (3-methacryloyl-oxypropyl) tris(trimethyl-siloxy) silane | 422.82 | 0.0393 | 2.712 | 0.1623 | 0.2092 |
| lucerin | 348.00 | 0.0014 | 0.080 | 0.0058 | 0.0062 |
| Diluent methanol | 32.04 | 0.5514 | 2.88 | 2.2751 | 0.2222 |
| Total | | 1.0000 | 12.9600 | | 1.0000 |

Example 6

Silicone Hydrogel SB4A

Silicone hydrogel SB4A was prepared and molded into sleeves as in Example 1. The components of the SB4A hydrogel are provided below. The SB4A hydrogel formulation included a methanol diluent and two different acrylic terminated siloxane monomers.

| Monomers | SB4A (Kinetic Study 3) | | | | |
|---|---|---|---|---|---|
| | molecular weight (g/gmole) | mole fraction | 10 gram hydrogel batch (g) | molar ratio to major monomer | wt fraction |
| Trimethylol propane trimethacrylate | 338.00 | 0.0019 | 0.131 | 0.0103 | 0.0091 |
| NVP | 111.14 | 0.0908 | 2.074 | 0.4963 | 0.1440 |
| GMA | 160.00 | 0.0322 | 1.058 | 0.1759 | 0.0735 |
| DMA | 99.13 | 0.1830 | 3.727 | 1.0000 | 0.2588 |
| (3-methacryloyl-oxypropyl) tris(trimethyl-siloxy) silane | 422.82 | 0.0347 | 3.010 | 0.1894 | 0.2091 |
| lucerin | 348.00 | 0.0011 | 0.080 | 0.0061 | 0.0056 |
| diluent methanol | 32.04 | 0.6563 | 4.32 | 3.5863 | 0.3000 |
| Total Diluent + hydrogel | | 1.0000 | 14.400 | | 1.0000 |

Example 7

Silicone Hydrogel SB4B

Silicone hydrogel SB4B was prepared and molded into sleeves as in Example 1. The components of the SB4B hydrogel are provided below. The SB4 hydrogel formulation also included a methanol diluent and two different acrylic terminated siloxane monomers.

| Monomers | SB4B (Kinetic Study 3) | | | | |
|---|---|---|---|---|---|
| | molecular weight (g/gmole) | mole fraction | 10 gram hydrogel batch (g) | molar ratio to major monomer | wt. fraction |
| Trimethylol propane trimethacrylate | 338.00 | 0.0019 | 0.137 | 0.0103 | 0.0095 |
| NVP | 111.14 | 0.0939 | 2.167 | 0.4963 | 0.1505 |
| GMA | 160.00 | 0.0333 | 1.106 | 0.1759 | 0.0768 |
| DMA | 99.13 | 0.1893 | 3.894 | 1.0000 | 0.2704 |
| (3-methacryloyl-oxypropyl) tris(trimethyl-siloxy) silane | 422.82 | 0.0307 | 2.696 | 0.1623 | 0.1872 |
| lucerin | 348.00 | 0.0011 | 0.080 | 0.0059 | 0.0056 |
| Diluent methanol | 32.04 | 0.6497 | 4.32 | 3.4321 | 0.3000 |
| Total | | 1.0000 | 14.4000 | | 1.0000 |

Example 8

Measurement of Hydration of the SB1 Hydrogel as a Function of Monomer Extraction Rate After curing, the hydration of the SB1 hydrogel formulation was measured as a function of the extraction rate of unreacted DMA and NVP monomers, as shown below. The formulation was immersed in saline (NaCl in deionized water, 0.9% w/w) using 3.5 mL of saline per sleeve containing approximately 60 mg of polymer per sleeve. The temperature was held constant at 55° C., and the solution was shaken in the incubated shaker at 100 rpm. Extraction was carried out for 1, 2, 3, 4, 6, 8, 12 and 24 hours, with the saline extractant being replaced with fresh saline solution after each period. The extraction process removes unreacted impurities from the polymer and also allows it to undergo hydration. Electrical resistance is believed to be dependent on the level of hydration of the polymer.

The extracts were analyzed by GC-MS chromatography, on an Agilent 7890A GC with Agilent 5975C mass selective quadrupole detector, monitoring N-vinyl pyrrolidone (NVP), Dimethyl acrylamide (DMA). Total ion chromatograms were recorded on each elute, and peaks identified using pure NVP, DMA and methanol as references.

Figure 21A:
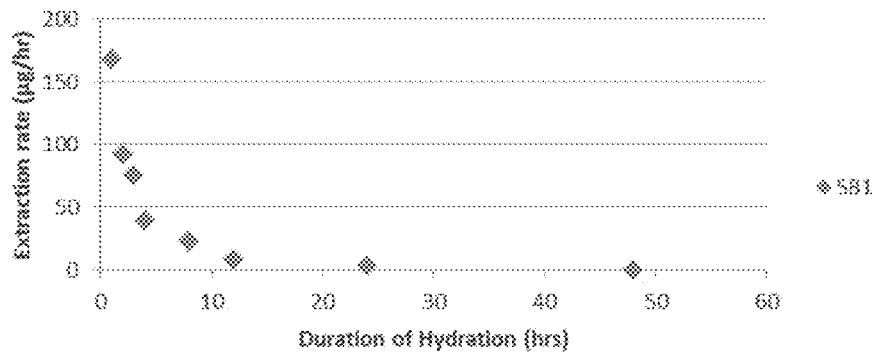
FIGS. 21A-21B show DMA and NVP monomer extraction rates for the SB1 hydrogel.
Figure 21B:
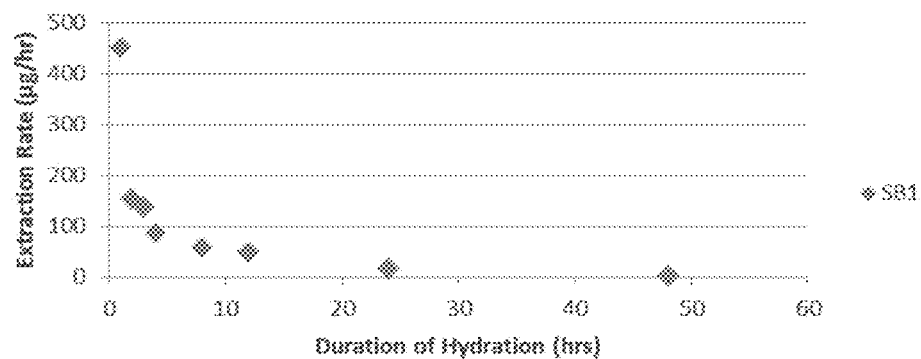

After about one hour of extraction (the terms extraction and hydration are used interchanageably in this application), the extraction rate for the SB1 hydrogel formulation was about 170 μg/hr for DMA (shown in FIG. 21A) and about 450 μg/hr for NVP (shown in FIG. 21B).

Example 9

Figure 22A:
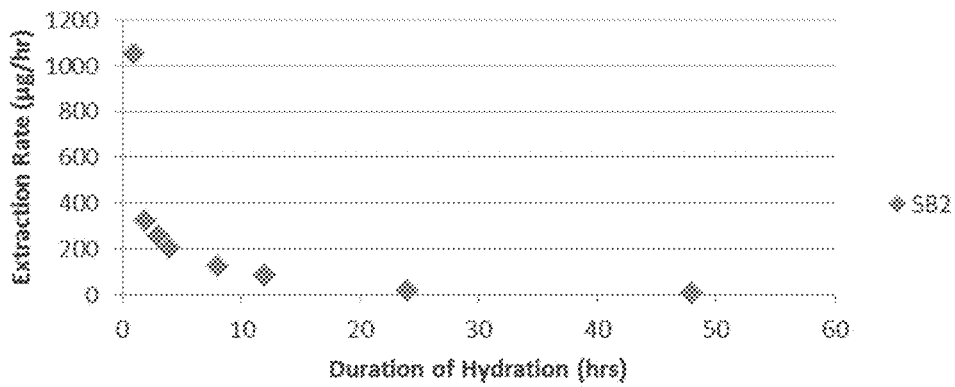
FIGS. 22A-22B show NVP monomer and methanol extraction rates for the SB2 hydrogel.
Figure 22B:
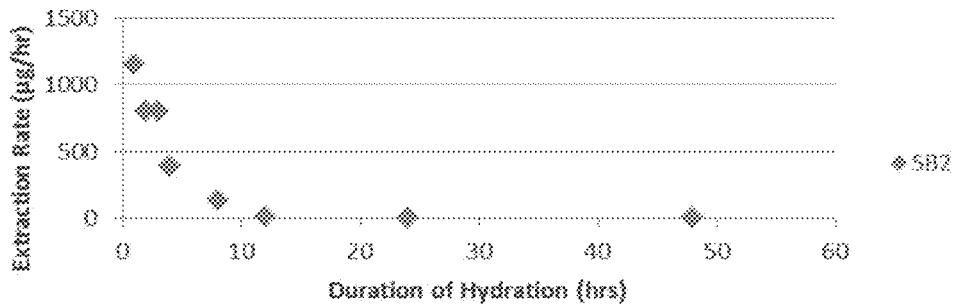

Measurement of Hydration of the SB2 Hydrogel as a Function of Monomer Extraction Rate After curing, the hydration of the SB2 hydrogel formulation was measured as a function of the extraction rate of unreacted NVP monomers, as shown in FIG. 22A and as described in Example 8, and as a function of the extraction rate of methanol, as shown in FIG. 22B. About one hour after curing, the extraction rate for the SB2 hydrogel formulation was about 1,150 µg/hr for NVP, which was much higher than that obtained with the SB1 hydrogel formulation. As noted above, a difference between the SB1 and SB2 formulations is that SB2 contained a methanol diluent. The presence of the diluent substantially accelerated the extraction of unreacted monomers from SB2, as shown by the relative rates of extraction of NVP from SB2 and SB1 (1,150 µg/hr vs. 450 µg/hr. However, the presence of the diluent also lowered the cure rate of SB2 relative to SB1, by reducing the effective mole fractions of each of the monomers (data not shown).

Example 10

Measurement of Hydration of the SB1 and SB2 Hydrogels as a Function of Electrical Resistance After curing, the hydration of the SB1 and SB2 hydrogel formulations were measured as a function of electrical resistance over a 72 hour extraction period (monomer extraction is a process that helps complete hydration of the hydrogel). Electrical resistance was measured by a multimeter set to read in serial resistance mode. One multimeter lead makes contact with the spring of the reference sleeve and the other with the spring of the test sleeve. The resistance measurement was read within 30 seconds. The resistance of the circuit, i.e., resistance other than the test sleeve, was estimated to be 2 kΩ. "Sleeve resistance," as referred to in the Examples, means resistance values specific to the sleeve, i.e., with the 2 kΩ removed.

Figures 23A, 23B:
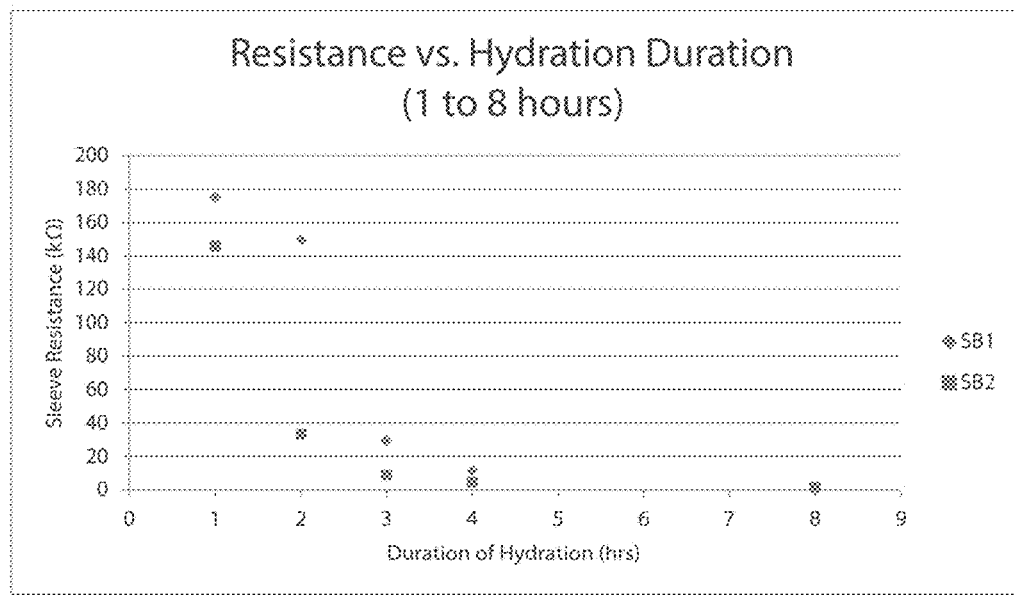
FIGS. 23A-23B provide data relating to hydration of the SB1 and SB2 hydrogels as a function of electrical resistance.

From the data provided in FIGS. 23A and 23B, it is shown that for both hydrogel formulations, the electrical resistance is high (approximately 145 to 175 kΩ) after the first hour of hydration/extraction, but as the hydrogel becomes more hydrated, the resistance drops (i.e., they become more conductive). The data is not plotted after 8 hours of hydration given the very low values.

Example 11

Figure 24A:
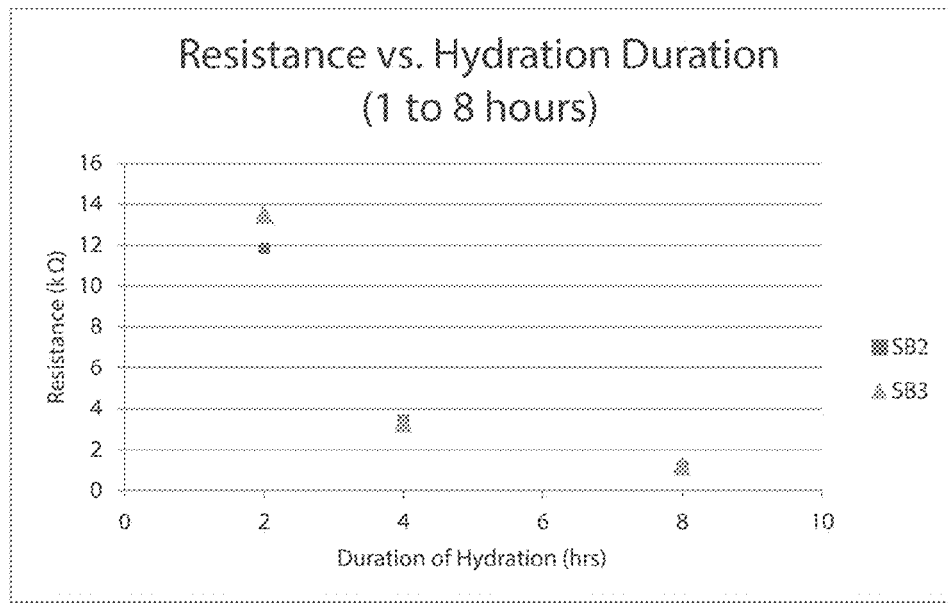
FIGS. 24A-24B provide data relating to the hydration of the SB2 and SB3 hydrogels as a function of electrical resistance.
Figure 24B:
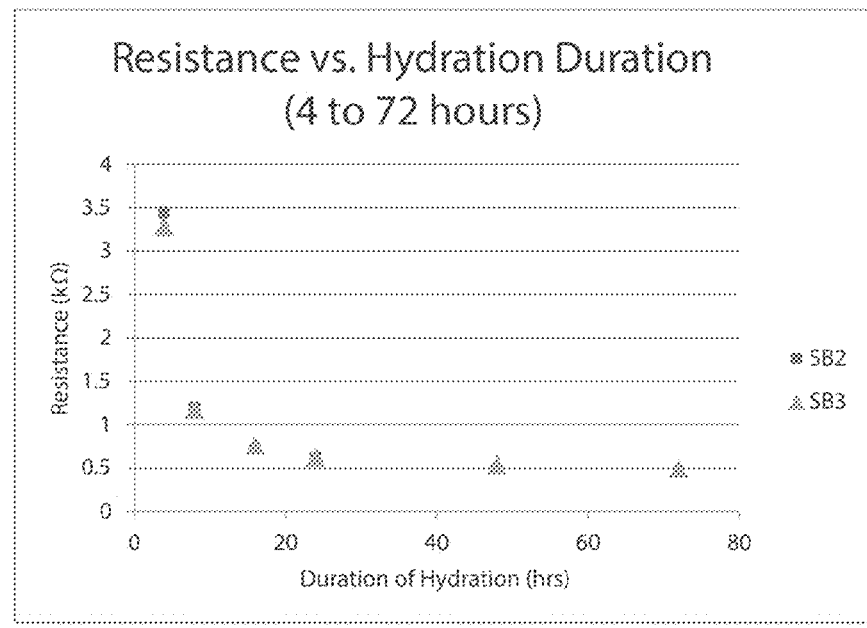

Measurement of Hydration of the SB2 and SB3 Hydrogels as a Function of Electrical Resistance After curing, the hydration of the SB2 and SB3 hydrogel formulations were measured as a function of electrical resistance over a period of one to 8 hours and a period of four to 72 hours, as described in Example 10. The data provided in FIGS. 24A and 24B show that hydration continues over a long period (here 72 hours). These hydrogels were still usable after 8 hours of hydration (they were still conductive). Furthermore, the gel mass of SB3 is significantly higher than that of SB2 after hydration. It should be noted that although the gel mass of SB3 is higher than that of SB2, gel height is lower for SB3. This is due to the presence of the diluent.

Example 12

Figure 25:
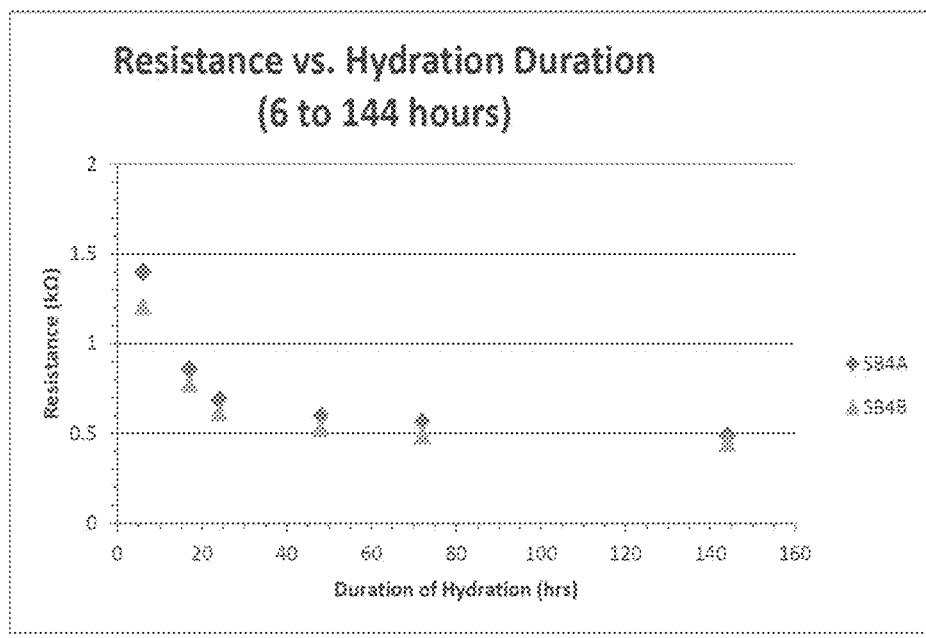
FIG. 25 provides data relating to the hydration of the SB4A and SB4B hydrogels as a function of electrical resistance.

Measurement of Hydration of the SB4A and SB4B Hydrogels as a Function of Electrical Resistance After curing, the hydration of the SB4A and SB4B hydrogel formulations were measured as a function of electrical resistance over a period of 144 hours. The data provided in FIG. 25 also shows that the hydrogels remain hydrated over a long period of time, and become more conductive as hydration increases.

Example 13

SB2 and SB3 Hydrogel Expansion Due to Hydration

Figure 26A:
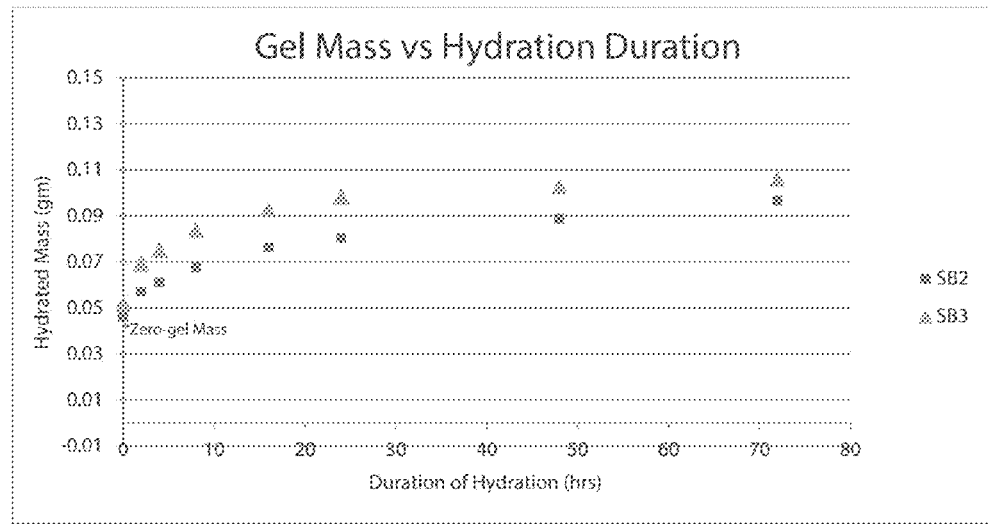
FIGS. 26A-26B provide data relating to expansion of the SB2 and SB3 hydrogels due to hydration.
Figure 26B:
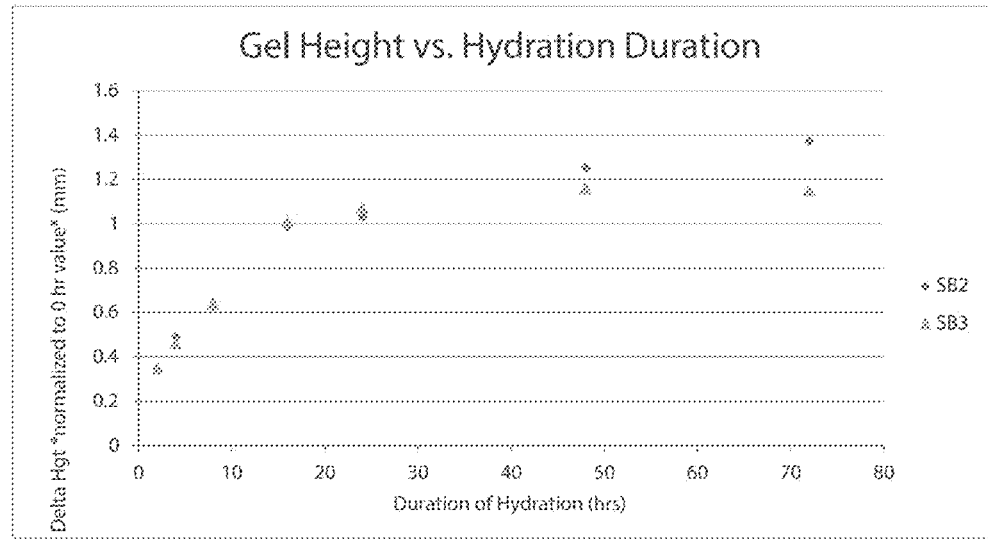

Mass and height for the SB2 and SB3 hydrogel casts were measured to determine swelling of the hydrogels as a function of hydration. The measurements are provided in FIGS. 26A and 26B.

Replacement of HEMA monomers with EGDMA monomers in SB3 rendered it more hydrophilic, which resulted in an increase in water uptake relative to SB2, and thus, a larger mass.

Example 14

SB4A and SB4B Hydrogel Expansion Due to Hydration

Figure 27A:
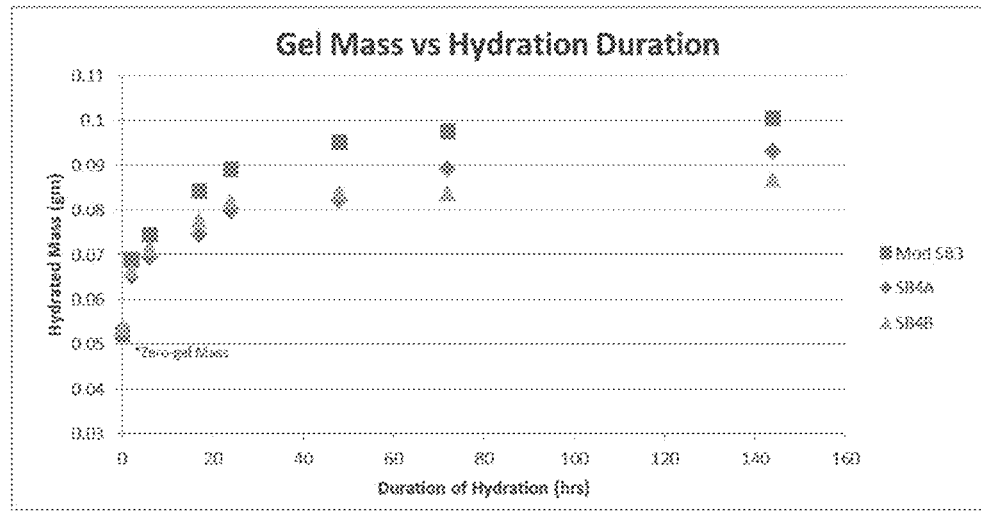
FIGS. 27A-27B provide data relating to expansion of the SB4A and SB4B hydrogels due to hydration.
Figure 27B:
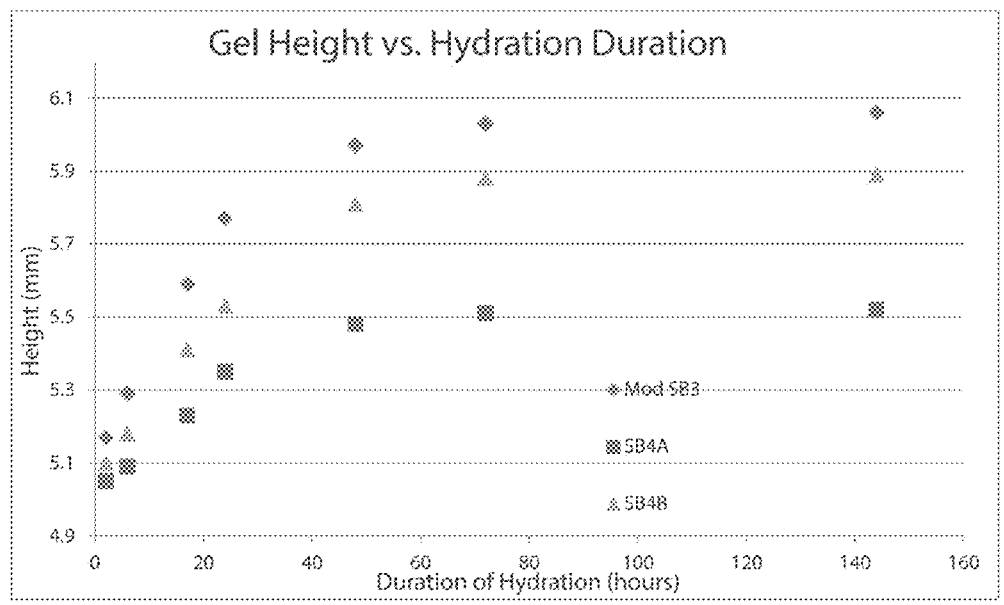

Mass and height for the SB4A and SB4B hydrogels were measured and compared to that of the SB3 hydrogel to determine swelling of the hydrogels as a function of hydration, as shown in FIGS. 27A and 27B. The SB4A and SB4B hydrogels, which exhibited high hydration (see Example 12) expanded less than the more hydrophilic SB3 hydrogel. Thus, with the SB4A and SB4B hydrogels, higher conductance was achieved with less swelling/expansion.

Example 15

Silicone Hydrogel SB5

Silicone hydrogel formulation SB5 was prepared and molded into sleeves as described in Example 1. The components of the SB5 hydrogel are provided below. A methanol diluent was included in the SB5 hydrogel formulation.

| SB5 | | | | | |
|---|---|---|---|---|---|
| Monomers | molecular weight (g/gmole) | mole fraction | 10 gram hydrogel batch (g) | molar ratio to major monomer | wt. fraction |
| Trimethylol propane trimethacrylate | 338.00 | 0.0021 | 0.119 | 0.0151 | 0.01186 |
| NVP | 111.14 | 0.0686 | 1.278 | 0.4957 | 0.12779 |
| GMA | 160.00 | 0.0243 | 0.653 | 0.1760 | 0.06530 |
| DMA | 99.13 | 0.1383 | 2.299 | 1.0000 | 0.22992 |
| (3-methacryloyl-oxypropyl) tris(trimethyl-siloxy) silane | 422.82 | 0.0224 | 1.591 | 0.1623 | 0.15914 |
| lucerin | 348.00 | 0.0011 | 0.067 | 0.0082 | 0.00666 |
| Diluent methanol | 32.04 | 0.7431 | 3.993 | 5.3738 | 0.39934 |
| Total | | 1.0000 | 10.0000 | | 1.0000 |

In the SB5 formulation, the UV initiator, diphenyl (2,4, 6-trimethylbenzoyl)phosphine oxide (CAS # 75980 60-8, Lucirin TPO), was selected since it is capable of being activated by UV radiation in the wavelength range of 400-450 nm, a band that is transmitted by the sleeve material (Versaflex OM3060-1, a styrene-ethylene/butylene-styrene copolymer). Addition of trimethylol propane trimethacrylate enhanced cross-link density and rendered the mixture more resistant to dry out.

Example 16

Figure 28A:
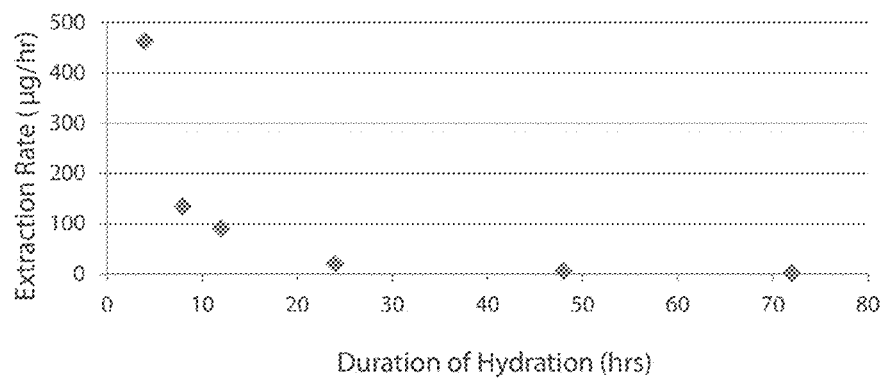
FIGS. 28A-28C show DMA and NVP monomer, and methanol extraction rates for the SB5 hydrogel.
Figure 28B:
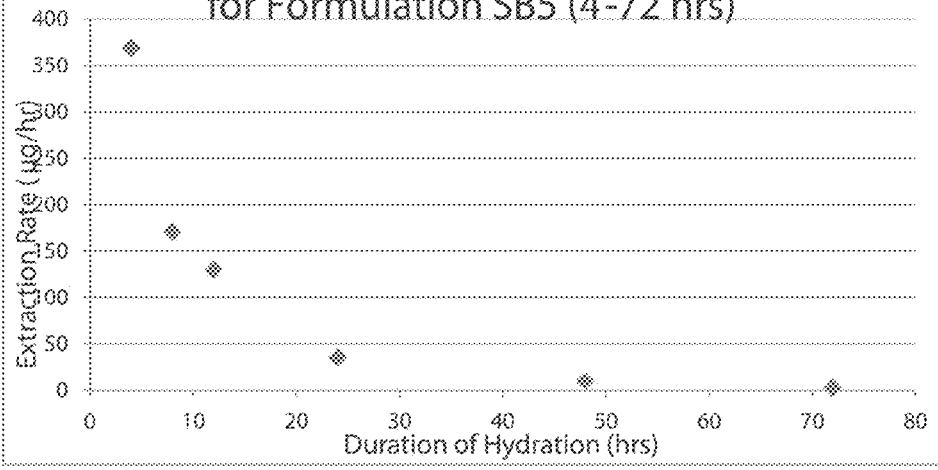
Figure 28C:
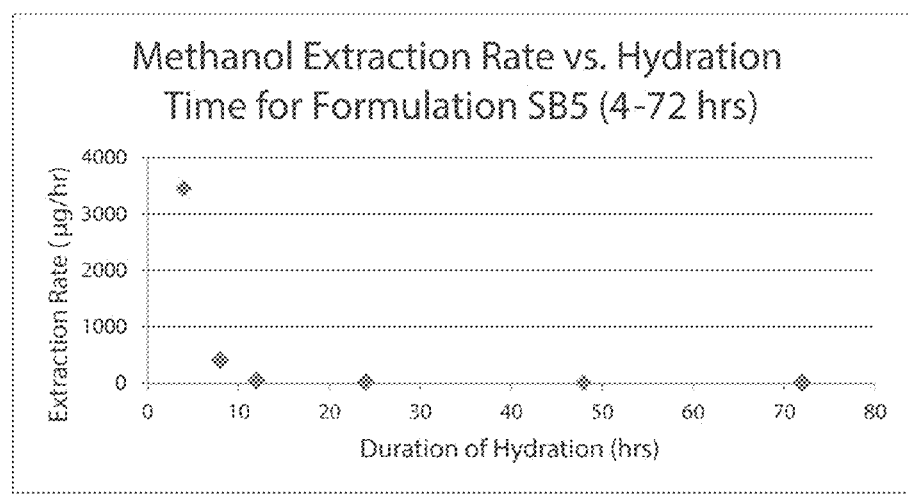

Measurement of Hydration of the SB5 Hydrogel as a Function of Monomer Extraction After curing, the hydration of the SB5 hydrogel was measured as a function of the extraction rate of unreacted DMA and NVP monomers, and methanol, as shown in FIGS. 28A-28C, and as similarly described in Example 8. Briefly, the extracts were analyzed by GC-MS chromatography, on an Agilent 7890A GC with Agilent 5975C mass selective quadrupole detector, monitoring N-vinyl pyrrolidone (NVP), Dimethyl acrylamide (DMA), and methanol (MeOH). Total ion chromatograms were recorded on each elute, and peaks identified using pure NVP, DMA, and methanol as references. The data in the graphs provided in FIGS. 28A-28C show that the rate of extraction of methanol is fastest followed by that of DMA. Extraction of NVP is the slowest. The extraction rate depends solely on the solubility of each species in saline at the temperature of hydration (55 degrees celsius), since the swelling of the hydrogel network is the same in all cases. As provided in the graphs, the extraction rates of all species appear to reach a low plateau after 24 hours of hydration. Based on these results, it was concluded that the SB5 hydrogel was ready to use after 24 hours of hydration.

Example 17

Figure 29:
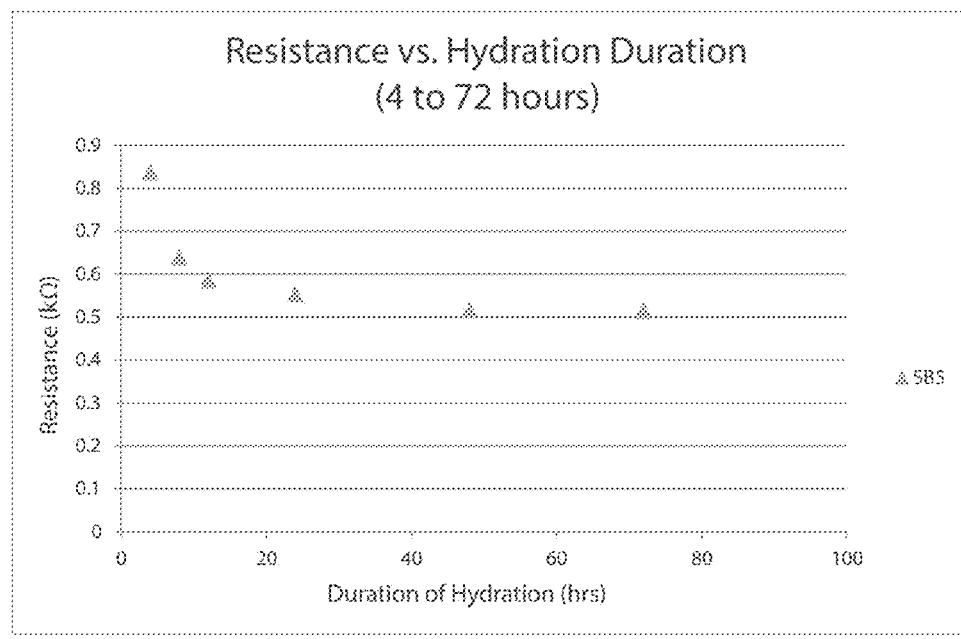
FIG. 29 provides data relating to the hydration of the SB5 hydrogel as a function of electrical resistance.

Measurement of Hydration of the SB5 Hydrogel as a Function of Electrical Resistance After curing, the hydration of the SB5 hydrogel formulation was measured as a function of electrical resistance over different periods of extraction, similar to that described in Examples 10-12. As shown in FIG. 29, the electrical resistance dropped significantly upon hydration caused by extraction with saline. The electrical resistance of the SB5 hydrogel reached a level of greater than 0.6 kΩ after 12 hours of extraction, and a lower plateau after approximately 24 hours of extraction.

Example 18

SB5 Hydrogel Expansion Due to Hydration

Mass and height (expansion) for the SB5 hydrogel casts were measured to determine swelling of the hydrogels as a function of hydration (and extraction period). Referring to the data table in FIG. 30A, at 48 hours, the hydration percentage (defined as $100*(M_{48\ hours}-M_{0\ hours})/M48$ hours, where M is mass in grams) of SB5 (42-05) is calculated to be about 35.5%, which was significantly less than that of SB1 (42-01) and SB2 (42-02). The reduced hydration percentage may be attributed to the increased crosslink density and increased hydrophobicity of SB5 relative to SB1 and SB2. Thus, benefits of the SB5 hydrogel may be that it is capable of achieving a level of electrical conductivity sufficient to perform its electrical function while also having a relatively low level of hydration, and that its processability is improved. The increased cross-link density also appeared to raise the glass transition temperature of the unhydrated hydrogel network (data not shown). These changes in the composition of the SB5 hydrogel relative to the SB1 and SB2 hydrogels may improve its drying out time and its robustness to shear forces induced by rubbing against nasal tissue.

Figures 30A, 30B:
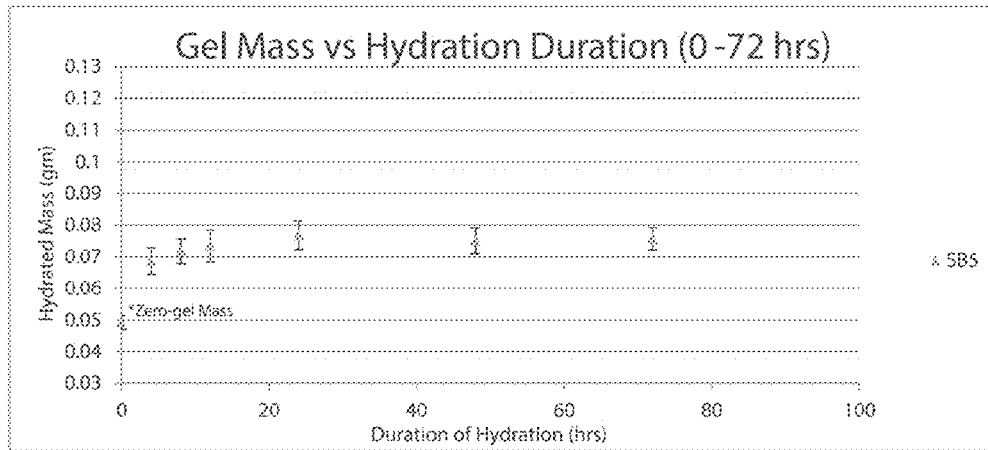
FIGS. 30A-30C provide data relating to expansion of the SB5 hydrogel due to hydration.

Referring to the Gel Mass vs. Hydration Duration graph provided in FIG. 30B, the SB5 hydrogel reached a threshold of hydration at about 24 hours of extraction, in contrast to the SB1 and SB2 hydrogels in which hydration continued to increase gel mass until about 72 hours (see, e.g., SB2 data in Example 13). This is consistent with the lower hydration percentage of SB5.

Figure 30C:
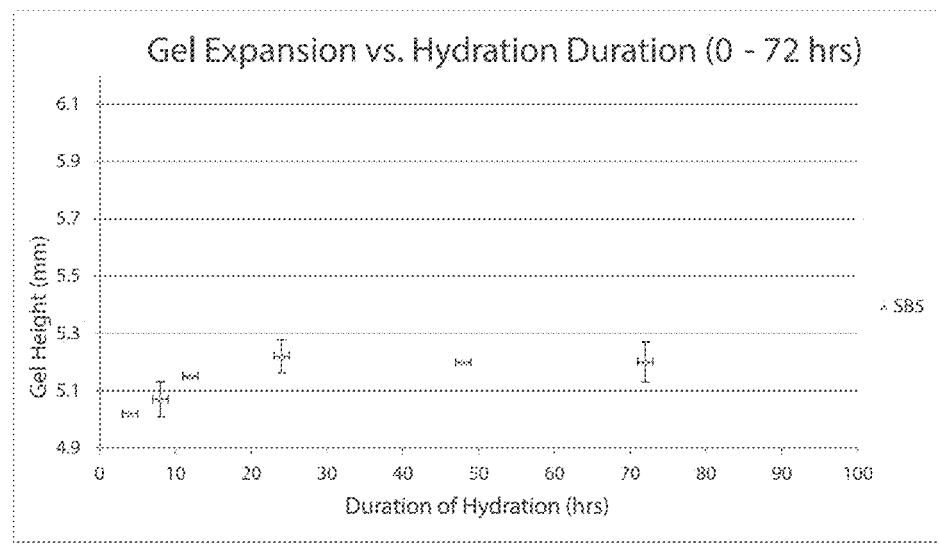

Provided in FIG. 30C is a Gel Expansion vs. Hydration Duration graph, which shows the data obtained from recording the increase in height of the SB5 hydrogel obtained from optical photos of hydrated sleeves. The data indicated that gel height reached a plateau after about 24 hours of extraction, in contrast to the SB1 and SB2 hydrogels, which continued to show increases in gel height up to and beyond 72 hours of extraction by saline under identical conditions (see, e.g., SB2 data in Example 13).

Overall, the data for the SB5 hydrogel showed that its equilibrium water content was about 35%. Referring to Example 15, the amount of methanol (diluent) used in this formulation is about 39.9%. These values indicate that the SB5 hydrogel is a zero expansion hydrogel. The data provided on gel height expansion showed an increase from 5.0 mm (measured prior to hydration) to 5.2 mm (after completion of hydration at about 24 hours), which indicates that an increase in about 4% is attributable to additional complexation of water molecules by the polymeric network relative to methanol.

Example 19

Contact Angle of the Silicone SB5 Hydrogel Formulation

The contact angle of the SB5 hydrogel used as an electrical contact at the tip of a nasal stimulator device was measured by placing 1 µl of deionized water on its surface, then photographing the drop using a Leica M-80 microscope having a L80nmnm digital camera, and having the LAS version 4.3.0 optical capture software. The contact angle was estimated from the photograph. The measurement was repeated using an electrical contact tip that had been hydrated by immersion into deionized water for 30 minutes just prior to measurement. The contact angle was measured to be 90 degrees in both cases. These results indicate that the surface of SB5 is hydrophobic, even though the overall gel mass is highly hydrophilic. Thus, the SB5 hydrogel appears to have a complex polymer morphology comprised of a hydrophilic core and a hydrophobic surface, e.g., as shown in FIG. 7. cl Example 20

Biocompatibility of the SB5 Hydrogel Formulation

MEM studies were performed on SB5 hydrogel samples hydrated in saline for 12 and 24 hours at 55 degrees celsius to determine the biocompatibility of the hydrogel, as shown below. The studies were completed by Acta Laboratories, Inc., in accordance with USP 36/NF 31 Supplement 2, (87) Biological Activity Tests, InVitro, Elution Test.

KS5 14043 12 hrs Elution Results

| Culture | % Intracyto-plasmic Granules | Confluent Monolayer | % Round and Loosely Attached | % Cell Lysis | Grade | Reac-tivity |
|---|---|---|---|---|---|---|
| Sample # 1 | 100 | (+) | 0 | 0 | 0 | None |
| Sample # 2 | 100 | (+) | 0 | 0 | 0 | None |
| Reagent Control # 1 | 100 | (+) | 0 | 0 | 0 | None |
| Reagent Control # 2 | 100 | (+) | 0 | 0 | 0 | None |
| Negative Control # 1 | 100 | (+) | 0 | 0 | 0 | None |
| Negative Control # 2 | 100 | (+) | 0 | 0 | 0 | None |
| Positive Control # 1 | 0 | (−) | 0 | 100 | 4 | Severe |
| Positive Control # 2 | 0 | (−) | 0 | 100 | 4 | Severe |

KS5 14043 24 hrs Elution Results

| Culture | % Intracyto-plasmic Granules | Confluent Monolayer | % Round and Loosely Attached | % Cell Lysis | Grade | Reac-tivity |
|---|---|---|---|---|---|---|
| Sample # 1 | 100 | (+) | 0 | 0 | 0 | None |
| Sample # 2 | 100 | (+) | 0 | 0 | 0 | None |
| Reagent Control # 1 | 100 | (+) | 0 | 0 | 0 | None |
| Reagent Control # 2 | 100 | (+) | 0 | 0 | 0 | None |
| Negative Control # 1 | 100 | (+) | 0 | 0 | 0 | None |
| Negative Control # 2 | 100 | (+) | 0 | 0 | 0 | None |
| Positive Control # 1 | 0 | (−) | 0 | 100 | 4 | Severe |
| Positive Control # 2 | 0 | (−) | 0 | 100 | 4 | Severe |

The invention claimed is:

1. A method for stimulating a lacrimal gland comprising:

placing an arm of a nasal stimulator device against a nasal or a sinus tissue, the arm having a distal end and a hydrogel electrode disposed at the distal end;

activating the nasal stimulator device to provide electrical stimulation to the nasal or the sinus tissue using the hydrogel electrode, wherein the hydrogel electrode comprises a mixture of:

glycerol monomethacrylate;

trimethylol propane trimethacrylate;

dimethylacrylamide;

N-vinylpyrrolidone;

2,4,6-trimethylbenzoyl-diphenylphosphine oxide; and methanol.

2. The method of claim 1, wherein the electrical stimulation is used to treat a type of dry eye.

3. The method of claim 2, wherein the type of dry eye is chronic dry eye, episodic dry eye, or seasonal dry eye.

4. The method of claim 1, wherein the electrical stimulation is used to treat dry eye due to age, a hormonal imbalance, an ocular allergy, a side effect of medication, Sjogren's syndrome, lupus, scleroderma, or a thyroid disorder.

5. The method of claim 1, wherein the electrical stimulation is used as a prophylactic measure after laser vision correction or cataract surgery.

6. The method of claim 1, wherein the electrical stimulation is provided one to five times a day.

7. The method of claim 1, wherein the hydrogel electrode further comprises a hydrating medium.

8. The method of claim 7, wherein the hydrating medium comprises propylene glycol.

9. The method of claim 1, wherein the hydrogel electrode further comprises 3-[tris(trimethylsiloxy)silyl]propyl methacrylate.

\* \* \* \* \*